(12) United States Patent
Tittiger et al.

(10) Patent No.: US 8,445,248 B2
(45) Date of Patent: May 21, 2013

(54) HYDROCARBON-FORMING OXIDATIVE DECARBONYLASE ENZYME, HYDROCARBONS PRODUCED THEREBY, AND METHOD OF USE

(75) Inventors: Claus Tittiger, Reno, NV (US); Gary Blomquist, Sparks, NV (US)

(73) Assignee: Board of Regents of the Nevada System of Higher Education on behalf of the University of Nevada, Reno, Reno, NV (US)

( * ) Notice: Subject to any disclaimer, the term of this patent is extended or adjusted under 35 U.S.C. 154(b) by 556 days.

(21) Appl. No.: 12/620,328

(22) Filed: Nov. 17, 2009

(65) Prior Publication Data
US 2010/0136595 A1 Jun. 3, 2010

Related U.S. Application Data

(60) Provisional application No. 61/115,382, filed on Nov. 17, 2008.

(51) Int. Cl.
*C12N 9/02* (2006.01)
*C12N 9/00* (2006.01)
*C12P 5/00* (2006.01)
*C12Q 1/26* (2006.01)
*C07H 21/04* (2006.01)

(52) U.S. Cl.
USPC ............ 435/189; 435/166; 435/183; 435/25; 536/23.2

(58) Field of Classification Search
None
See application file for complete search history.

(56) References Cited

U.S. PATENT DOCUMENTS 7,785,861 B2  8/2010  Devroe et al.
7,794,969 B1  9/2010  Reppas et al.

OTHER PUBLICATIONS

Whisstock et al. Quaterly Reviews of Biophysics, 2003, "Prediciton of protein function from protein sequence and structure", 36(3): 307-340.*
Witkowski et al. Conversion of a beta-ketoacyl synthase to a malonyl decarboxylase by replacement of the active-site cysteine with glutamine, Biochemistry. Sep. 7, 1999;38(36):11643-50.*
UniProt Accession No. A8DY23 (created on Nov. 13, 2007).*
Zhu et al. (Co-up Co-up-regulation of three P450 genes in response to permethrin exposure in permethrin resistant house flies, *Musca domestica*, BMC Physiology (2008), 8(18): 1-13).*

* cited by examiner

*Primary Examiner* — Anand Desai
*Assistant Examiner* — Iqbal H Chowdhury
(74) *Attorney, Agent, or Firm* — Klarquist Sparkman, LLP

(57) ABSTRACT

The present disclosure relates to oxidative decarbonylase enzymes, methods of making hydrocarbons with such enzymes, hydrocarbons produced therefrom and uses thereof. More particularly, the present disclosure relates to isolated polypeptide sequences that are cytochrome P450 enzymes with oxidative decarbonylase activity and methods of their use to generate hydrocarbon products, such as biofuels.

4 Claims, 11 Drawing Sheets

FIG. 8

```
CP3A4    --------------------MALIPDLAMETWLLLAVSLVLLYLYGTHSHGLFKKLGIPG  40
CYP4G2   MTADTLVLETMDSAKNSTAGPATVLNPIWTALLGIAVVVSLYEIWLRNTRKYKLTANMPN  60
CP51     -----------------------------------MSAVALPRVSGGHDEHGHLEEFRTD  25
                                            :  *     :    :.       ..

CP3A4    PTPLPFLGN--ILSYHKGFCMFD--MECHKKYG-KVWGFYDGQQPVLAITDPDMIKTVLV  95
CYP4G2   PPMLPLIGNGHLVAHLTNAEILARGIGYMQTYGGAMRGFLGPMLVVFLWNAPDIELILST 120
CP51     P----------------IGLMQRVRDECGDVG--TFQLAGKQVVLLSGSHANEFFFRAG   66
         *                  ::          *       :  .     ::    . .:

CP3A4    KECYSVFTNRRPFGPVGFMKSAISIAEDEEWKRLRSLLSPTFTSGKLKEMVPIIAQYGDV 155
CYP4G2   HTHLEKSIEYRFFKP--WFGDGLLISNGHHWQHHRKMIAPTFHQSILKSFVPAFVQHSKK 178
CP51     DDDLDQAKAYPFMTP--IFGEGVVFDASPERRKE-MLHNAALRGEQMKGHAATIEDQVRR 123
          .   .          : *    :  ..:  .  .::    :   .::     :*  .. : :

CP3A4    LVRNLRREAETGKPVTLKDVFGAYSMDVITSTSFGVNIDSLNNPQDPFVEN--------T 207
CYP4G2   VVE--RMAKELGKEFDVHDYMSQTTVEILLSTAMGVKKVPEDNKSLEYAKAVVDMCDIIH 236
CP51     MIA----DWGEAGEIDLLDFFAELTIYTSSACLIGKKFRDQLDG---------------- 163
         ::         .  .:*  :.  ::           :   :*                :

CP3A4    KKLLRFDFLDPFFLSITVFP----FLIPILEVLNICVFPREVTNFLRKS----------V 253
CYP4G2   KRQLKFFYRMDALYNLSSMSEKGKKMMDIILGMTRKVVTERQQNFNAESRAIVEEDDEIS 296
CP51     -RFAKLYHELERGTDPLAYVDP---YLPIESFRRRDEARNGLVALVADIMN--------- 210
          : ::  .   .           : *                .        :      .
                                                          _____
CP3A4    KRMKESRLEDTQKHRVDFLQ----------LMIDSQNSKETES-HKALSDLELVAQSIIF 302
CYP4G2   KQKQQAKKKEGLRDDLDDIDENDVGAKKRLALLDAMMAMSKNP-DVEWTDKDVMDEVNTI 355
CP51     GRIANPPTDKSDRD----------------MLDVLIAVKAETGTPRFSADEITGMFISM 253
            :  :. .. :.                 ::*  :  . :.    :  ::     :
         _____

CP3A4    IFAGYETTSSVLSFIMYELATHPDVQQKLQEEIDAVLPN--KAPPTYDTVLQMEYLDMVV 360
CYP4G2   MFEGHDTTSAGSSFVLCMLGIYKDIQEKVLAEQKAIFGDNFLRDCTFADTMEMKYLERVI 415
CP51     MFAGHHTSSGTASWTLIELMRHRDAYAAVIDELDELYGD--GRSVSFHALRQIPQLENVL 311
         :* *:.*:*.  *:   :  *  :  *. : :    :       ::     ::    *: *:

CP3A4    NETLRLFPIAMRLERVCKKDVEING--MFIPKGVVVMIPSYALHRDPKYWTEPEKFIPER 418
CYP4G2   METLRLYPPVPLIARRAEFDVKLASGPYTIPKGTTVVIAQFAVHRNPQYFPNPEKFDPDN 475
CP51     KETLRLHPPLIILMRVAKGEFEVQG--HRIHEGDLVAASPAISNRIPEDFPLPHDFVPAR 369
          *****.*   :  * .:  : .: .   * :*     *   .:     :* *:  :.:*..* .

CP3A4    FS-KKNDNIDPYIYTPFGSGPRNCIGMRFALMNMKLALIRVLQNFSFKPCKETQIPLKL 477
CYP4G2   FL-PERMANRHYYSFIPFSAGPRSCVGRKYAMLKLKVLLSTIIRNYSVQ-SNQQEKDFKL 533
CP51     YEQPRQEDLLNRWTWIPFGAGRHRCVGAAFAIMQIKAIFSVLLREYEFEMAQPPESYRND 429
          :   ..     .: : **.:* ::*   :* :  :  *    :*:::::..:   *  .
         _____

CP3A4    SLGGLLQPEKPVVLKVESRDGTVSGA 503
CYP4G2   QADTTLKTENGFNTMLNRRPEAMKAM 559
CP51     HSKMVVQLAQPACVRYRRRTGV---- 451
         :::   :   :    : . *   .
```

HYDROCARBON-FORMING OXIDATIVE DECARBONYLASE ENZYME, HYDROCARBONS PRODUCED THEREBY, AND METHOD OF USE

CROSS-REFERENCE TO RELATED APPLICATION

This application claims the benefit of U.S. Provisional Application No. 61/115,382 filed Nov. 17, 2008, which is herein incorporated by reference in its entirety.

ACKNOWLEDGMENT OF GOVERNMENT SUPPORT

This invention was made with government support under IBN-9630916 awarded by the National Science Foundation and United States Department of Agriculture-National Research Initiative, Grant/Contract Nos. 94-37302-0612 and 96-35302-3416. The United States Government has certain rights in the invention.

FIELD

The present disclosure generally relates to a hydrocarbon-forming oxidative decarbonylase enzyme, hydrocarbons produced thereby and uses thereof.

BACKGROUND

Hydrocarbons are ubiquitous compounds in nature. The surface waxes of plants and insects contain very-long chain, non-isoprenoid hydrocarbons of 21 to over 50 carbons. Plant cuticular hydrocarbons are generally straight-chain, n-alkanes whereas insect cuticular hydrocarbons also often contain methyl-branched and unsaturated components. Long-chain hydrocarbons are also present in algae, uropygial glands of water birds, and in small amounts in many other organisms. Long-chain hydrocarbons of insects play central roles in waterproofing the insect cuticle and function extensively in chemical communication where relatively non-volatile chemicals are required. The recognition of the roles that hydrocarbons serve as sex pheromones, kairomones, species and gender recognition cues, nestmate recognition, dominance and fertility cues, chemical mimicry, primer pheromones, task specific cues and even as cues for maternal care of offspring has resulted in an explosion of new information in this area.

The ability of insects to withstand desiccation was recognized in the 1930s to be due to the epicuticular wax layer on the cuticle. The development and application of combined gas-liquid chromatography and mass spectrometry allowed rapid and efficient analyses of insect hydrocarbons. In the late 1960s and during the next few decades, it was recognized that for many insect species, very complex mixtures of normal (straight-chain), methyl-branched and unsaturated components existed, with chain lengths ranging from 21 to 50+ carbons. It was also recognized that the variety of chain lengths, the number and positions of the methyl branches and double bonds provided insects with the chemical equivalent of the visually variable colored plumage of birds.

Insects synthesize hydrocarbons by elongating fatty acyl-CoAs to produce the very long-chain fatty acids that are then converted to hydrocarbons by loss of the carboxyl group. Methyl-branched hydrocarbons (with the exception of 2-methylalkanes) arise from the incorporation of a propionyl-CoA group (as methylmalonyl-CoA derived from valine, isoleucine or methionine) in place of an acetyl-CoA group at specific points during chain elongation. 2-Methylalkanes arise from the elongation of the carbon skeleton of either valine (even number of carbons in the chain) or isoleucine (odd number of carbons in the chain). Insect hydrocarbon biosynthesis occurs in oenocytes (large secretory cells found in clusters underlying the epidermis of larval abdominal segments).

Although it is now clear that fatty acyl-CoAs are reduced to aldehydes and then converted to hydrocarbons by the loss of the carbonyl carbon, the mechanism by which the latter step occurs remains to be identified.

SUMMARY

Disclosed is the surprising identification of the mechanism by which fatty aldehydes are converted into hydrocarbons. Isolated polypeptides that are cytochrome P450 enzymes that have hydrocarbon-forming oxidative decarbonylase activity are disclosed. Cells, for instance fungal or bacterial cells, transformed with one or more nucleic acid sequences that encode one or more of the disclosed polypeptides, can be used as a source for hydrocarbons. As such, this discovery provides methods of producing hydrocarbons that can be used for the production of a wide range of products, such as hydrocarbon sex-pheromone components for *Musca domestica* control, biofuels, lubricants, or solvents.

One embodiment of the disclosure is an isolated polypeptide with an amino acid sequence set forth by SEQ ID NO: 1 or 2 or a sequence having at least 95% sequence identity, such as 99% sequence identity with SEQ ID NO: 1 or 2. Another embodiment is a polynucleotide that encodes an isolated polypeptide with an amino acid sequence set forth by SEQ ID NO: 1 or 2 or a sequence having at least 95% sequence identity, such as 99% sequence identify with SEQ ID NO: 1 or 2.

Another embodiment is a method of producing a hydrocarbon. In one example, the method includes transforming a cell with a recombinant construct containing a promoter operably linked to a nucleic acid sequence, wherein the nucleic acid sequence encodes a protein comprising SEQ ID NO: 1 or 2 or a sequence having at least 95% sequence identity with SEQ ID NO: 1 or 2 and culturing the cell under conditions wherein the cell expresses the protein, thereby producing the hydrocarbon.

In another example, the method of producing a hydrocarbon includes methods of making hydrocarbons in vitro, or partially in vitro. For example, one or more of the peptides described herein can be isolated and then allowed to react with a substrate in vitro to make an intermediate. That intermediate can then be added to a cell culture wherein the cells convert the intermediate to the desired product. In instances where the desired product is made entirely in vitro all of the necessary enzymes are reacted in vitro. However, the enzymes can be added sequentially or simultaneously and at various stages in the reaction, for example after intermediate purification or partial purification.

Also disclosed are embodiments of a method for using the disclosed enzymes and hydrocarbons produced therefrom. One use of the disclosed enzymes is the production of synthetic hydrocarbon sex-pheromone components for *Musca domestica* control. Another use is the production of hydrocarbons as biofuels, either in vitro, or by inserting the isolated disclosed sequences, such as SEQ ID NO: 1 or 2 (or related sequences, see Table A) into an organism (e.g., plant, bacteria, algae, etc.) in order to alter the hydrocarbon content, such as increasing the content, for production of fuel, lubricant, solvent, etc. For example, biofuel produced by a provided method is disclosed.

The foregoing and other features will become more apparent from the following detailed description of several embodiments, which proceeds with reference to the accompanying figures and sequence listing.

BRIEF DESCRIPTION OF THE DRAWINGS

FIG. 8 is a ClustalW 2.0 multiple sequence alignment of *Homo sapiens* cytochrome CYP3A4 (SEQ ID NO: 48, GenBank Accession No. P08684, PDB 1TQN, top), *Musca domestica* CYP4G2 (SEQ ID NO: 1, middle), and *Mycobacterium tuberculosis* P450 51 (SEQ ID NO: 49, GenBank Accession No. P08512, PDB 2CIB, bottom). Invariant glycines and prolines (designated by a "G" and "P", respectively) that are conserved in all three sequences are boxed; conserved cysteines are double-underlined and a C; and the highly conserved region is overlined and the less conserved region is in not.

SEQUENCE LISTING

Figure 1A:
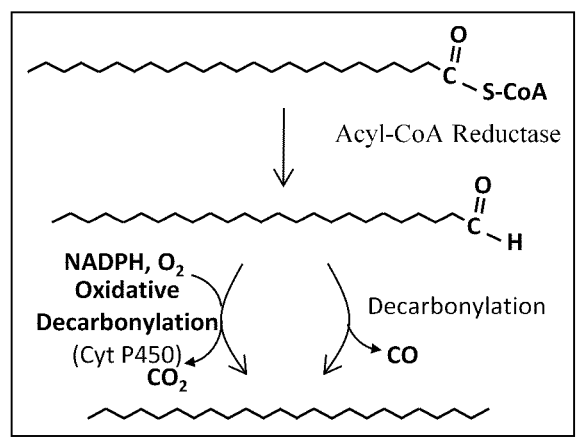
FIG. 1A is a schematic diagram illustrating an exemplary pathway of hydrocarbon biosynthesis in accordance with the present disclosure in which the oxidative decarbonylation pathway uses cytochrome P450 and produces carbon dioxide while the decarbonylation pathway produces carbon monoxide.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

SEQ ID NO: 1 is the amino acid sequence of cytochrome P450 4g2 (CYP4G2).

SEQ ID NO: 2 is the amino acid sequence of cytochrome P450 4g1 (CYP4G1).

SEQ ID NO: 3 is the amino acid sequence of GG12761 from *Drosophila erecta*.

SEQ ID NO: 4 is the amino acid sequence of GD24639 from *Drosophila simulans*.

SEQ ID NO: 5 is the amino acid sequence of GE16587 from *Drosophila yakuba*.

SEQ ID NO: 6 is the amino acid sequence of GA17813 from *Drosophila pseudoobscura*.

SEQ ID NO: 7 is the amino acid sequence of GI11123 from *Drosophila mojavensis*.

SEQ ID NO: 8 is the amino acid sequence of GJ15981 from *Drosophila virilis*.

SEQ ID NO: 9 is the amino acid sequence of GF20812 from *Drosophila ananassae*.

SEQ ID NO: 10 is the amino acid sequence of GH24346 from *Drosophila grimshawi*.

SEQ ID NO: 11 is the amino acid sequence of GK25658 from *Drosophila willistoni*.

SEQ ID NO: 12 is the amino acid sequence of cytochrome P450 4g15 from *Culex quinquefasciatus*.

SEQ ID NO: 13 is an amino acid sequence of cytochrome P450 from *Aedes aegypti*.

SEQ ID NO: 14 is the amino acid sequence of cytochrome P450 from *Aedes aegypti*.

SEQ ID NO: 15 is an amino acid sequence similar to cytochrome P450 from *Nasonia vitripennis*.

SEQ ID NO: 16 is an amino acid sequence similar to cytochrome P450 monooxygenase from *Nasonia vitripennis*.

SEQ ID NO: 17 is the amino acid sequence of cytochrome P450 family 4 from *Chironomus tentans*.

SEQ ID NO: 18 is the amino acid sequence of AGAP000877-PA from *Anopheles gambiae* str. PEST.

SEQ ID NO: 19 is the amino acid sequence of AGAP001076-PA from *Anopheles gambiae* str. PEST.

SEQ ID NO: 20 is the amino acid sequence of cytochrome P450 monooxygenase CYP4G7 from *Tribolium castaneum*.

SEQ ID NO: 21 is the amino acid sequence of cytochrome P450 monooxygenase *Tribolium castaneum*.

SEQ ID NO: 22 is the amino acid sequence of cytochrome P450 from *Bombyx mori*.

SEQ ID NO: 23 is the amino acid sequence of cytochrome P450 4G25 (CYP4G25) *Bombyx mori*.

SEQ ID NO: 24 is the amino acid sequence of cytochrome P450 from *Leptinotarsa decemlineata*.

SEQ ID NO: 25 is the amino acid sequence of GM13084 from *Drosophila sechellia*.

SEQ ID NO: 26 is the amino acid sequence of cytochrome P450 monooxygenase from *Apis mellifera*.

SEQ ID NO: 27 is the amino acid sequence of cytochrome P450 4G19 monooxygenase (CYP4G19) from *Blattella germanica*.

SEQ ID NO: 28 is the amino acid sequence of CYP4G27 from Ips paraconfusus.

SEQ ID NO: 29 is the amino acid sequence of cytochrome P450 4G25 (CYP4G25) from *Antheraea yamamai*.

SEQ ID NO: 30 is the amino acid sequence of antennal cytochrome P450 4 (CYP4) from *Mamestra brassicae*.

SEQ ID NO: 31 is an amino acid sequence similar to cytochrome P450 from *Acyrthosiphon pisum*.

SEQ ID NO: 32 is the amino acid sequence of GL20168 from *Drosophila persimilis*.

SEQ ID NO: 33 is the amino acid sequence of cytochrome P450 4C1 (CYPIVC1) from *Blaberus discoidalis* (roaches).

SEQ ID NO: 34 is the amino acid sequence of cytochrome P450 4C39 (CYP4C39) from green crab, common shore crab.

SEQ ID NO: 35 is the amino acid sequence of hypothetical protein BRAFLDRAFT_57954 from *Branchiostoma floridae*.

SEQ ID NO: 36 is the amino acid sequence of cytochrome 4V6 from *Balaenoptera acutorostrata*.

SEQ ID NO: 37 is the amino acid sequence of cytochrome P450 4M6 monooxygenase (CYP4M6) from *Helicoverpa zea*.

SEQ ID NO: 38 is the amino acid sequence of cytochrome P450 4 family from *Daphnia magna*.

SEQ ID NO: 39 is the amino acid sequence of cytochrome P450 from *Nilaparvata lugens*.

SEQ ID NO: 40 is the amino acid sequence of hypothetical protein L00562008 *Danio rerio*.

SEQ ID NO: 41 is the amino acid sequence of cytochrome P450, family 735, subfamily A, polypeptide 1 (CYP735A1) oxygen binding protein from *Arabidopsis thaliana*.

SEQ ID NO: 42 is the amino acid sequence of cytochrome P450 like protein from *Arabidopsis thaliana*.

SEQ ID NO: 43 is the amino acid sequence of hypothetical protein OsI_028301 from *Oryza sativa* (indica cultivar-group).

SEQ ID NO: 44 is the amino acid sequence of hypothetical protein OsI_003357 from *Oryza sativa* (indica cultivar-group).

SEQ ID NO: 45 is the amino acid sequence of hypothetical protein OsI_005901 from *Oryza sativa* (indica cultivar-group).

SEQ ID NO: 46 is a nucleic acid sequence of cytochrome P450 4g2 (CYP4G2).

SEQ ID NO: 47 is the nucleic acid sequence of cytochrome P450 4g2 (CYP4G2).

SEQ ID NO: 48 is the nucleic acid sequence of cytochrome P450 4g1 (CYP4G1).

SEQ ID NO: 49 is the amino acid sequence of cytochrome CYP3A4 from *Homo sapiens*.

SEQ ID NO: 50 is the amino acid sequence of cytochrome P450 51 from *Mycobacterium tuberculosis*.

SEQ ID NO: 51 is a nucleic acid sequence of cytochrome P450 chimera 9T2/4G2.

SEQ ID NO: 52 is an amino acid sequence of cytochrome P450 chimera 9T2/4G2.

DETAILED DESCRIPTION

I. Overview of Several Embodiments

Figure 1B:
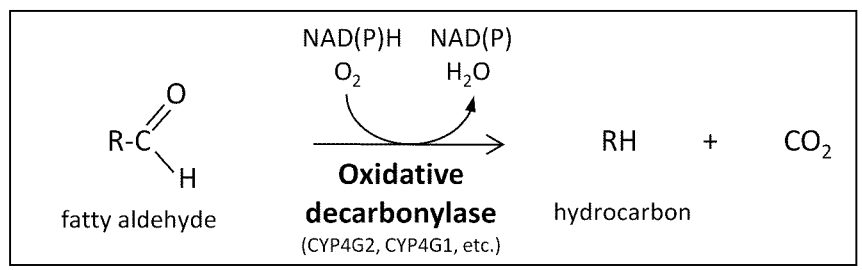
FIG. 1B is a schematic diagram illustrating the function of a hydrocarbon-forming oxidative decarbonylase according to the present disclosure, which converts fatty aldehydes to linear hydrocarbons.

Fatty acyl-CoAs are reduced to aldehydes (FIG. 1A) and then converted to hydrocarbons by the loss of the carbonyl carbon. However, prior to the present disclosure the mechanism of the last step in this process, the conversion of aldehyde to hydrocarbon, was unclear. Previously it had been suggested that in plants, algae, vertebrates and insects, the aldehyde is decarbonylated to hydrocarbon and carbon monoxide (FIG. 1A) in a process that does not require cofactors. In contrast to these previous findings, it disclosed herein that the conversion of the aldehyde to hydrocarbon and carbon dioxide involves a cytochrome P450 enzyme with hydrocarbon-forming oxidative decarbonylase activity, molecular oxygen and NADPH (FIG. 1B).

Figure 2:
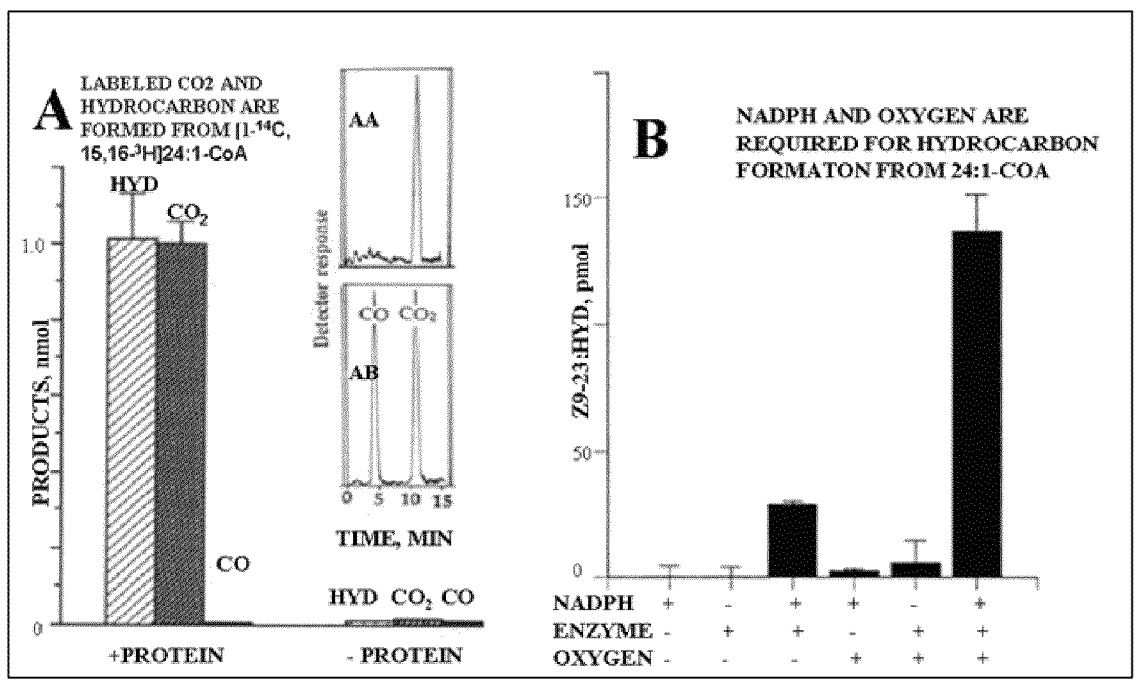
FIG. 2A is a bar graph and a pair of tracings illustrating that in housefly microsomes, incubation of (Z)-15-[1-$^{14}$C]- and (Z)-15-[15,16-$^{3}$H$_2$]tetracosenoyl-CoA and the corresponding aldehydes in the presence of NADPH gave equal amounts of $^{14}CO_2$ and [$^3$H]—(Z)-9-tricosene.
FIG. 2B is a bar graph demonstrating that NADPH and oxygen are required for hydrocarbon formation from 24:1-CoA.

For example, in housefly microsomes, incubation of (Z)-15-[1-$^{14}$C]— and (Z)-15-[15,16-$^3$H$_2$]tetracosenoyl-CoA and the corresponding aldehydes in the presence of NADPH gave equal amounts of $^{14}$CO$_2$ and [$^3$H]—(Z)-9-tricosene (FIG. 2A). The formation of labeled carbon dioxide and not carbon monoxide was verified by both radio-GLC (FIG. 2B) and trapping agents.

The demonstration of a requirement for NADPH and O$_2$ and inhibition by CO and antibody to cytochrome P450 reductase implicated a cytochrome P450 in the reaction. However, to resolve the controversy of whether hydrocarbon formation involved decarboxylation or decarbonylation, the enzyme(s) involved in such process needed to not only be identified, but characterized both molecularly and biologically.

Figure 3:
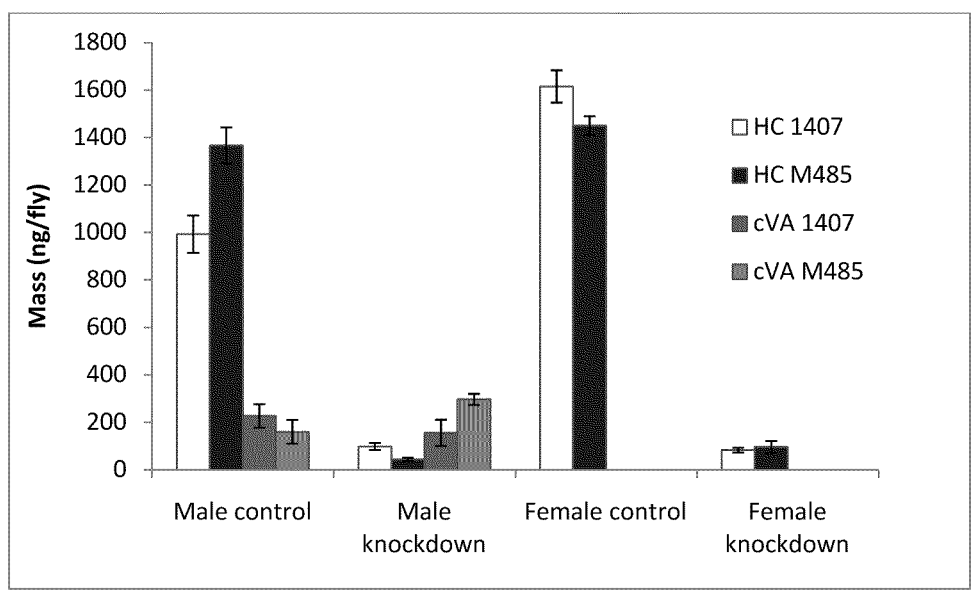
FIG. 3 is a bar graph illustrating the amount of hydrocarbon production for control and knocked down (1405Cyp and M485Cyp) flies.

Herein, the inventors have identified several integument enriched cytochrome P450 cDNAs in the housefly, *Musca domestica*. One of these, CPY4G2 was found to have 71.7% amino acid identity and 81.8% similarity to its ortholog, CYP4G1, in *Drosophila melanogaster*. Two transgenic *D. melanogaster* lines (3972-R1 and 3972-R2) bearing CYP4G1 hairpin sequences under control of the yeast UAS promoter were crossed individually with a transgenic line carrying the Gal4 transcription factor gene under control of an oenocyte-specific promoter. Offspring from these crosses expressed CYP4G1 hairpin RNAs specifically in their oenocytes, thus triggering RNAi-mediated post-transcriptional gene silencing of CYP4G1 in oenocytes. The amount of hydrocarbon produced by these flies was less than 100 ng/fly, as compared to about 1500 ng/fly in parental insects (FIG. 3). The amount of cis-valeryl acetate was constant in test samples and control samples, indicating that fatty acid synthesis was not affected (FIG. 3).

These studies demonstrate that CYP4G2 and CYP4G1 are cytochrome P450 enzymes with oxidative decarbonylase activity involved in hydrocarbon biosynthesis and can be utilized to produce hydrocarbons, such as those used for biofuel production. For example, cells, for instance fungal, plant, or bacterial cells, that have been transformed with one or more of genes that encode these enzymes can be used as a source for hydrocarbons, such as a source for hydrocarbons that can be used as fuel in place of limited, non-renewable hydrocarbon resources. By controlling the host organism and/or the reaction substrates (for instance, controlling for chain length, branching and saturation and/or location of double bonds), microorganisms can be created that produce a wide range of hydrocarbons, including those having particular branches or unsaturated points.

One aspect of the disclosure provides isolated polypeptides that have oxidative decarbonylase activity. In one particular aspect, isolated recombinant nucleic acid sequences that encode proteins having oxidative decarbonylase activity are provided, such as isolated recombinant nucleic acid sequences that encode proteins having oxidative decarbonylase activity and share at least 95% sequence identity with amino sequence set forth by SEQ ID NO: 1 or 2. In one example, an isolated recombinant nucleic acid includes a promoter operably linked to a nucleic acid sequence encoding: (a) SEQ ID NO: 1 or 2 or (b) a sequence having at least 95% sequence identity with SEQ ID NO: 1 or 2. In some examples, the isolated recombinant nucleic acid includes a vector, and in certain examples, the vector is a plasmid, for instance pET-21b(+), pCOLADuet-1, pcDNA3.1(+), pCMV SPORT6.1, pCDFDuet-1, pENTR4 (Invitrogen), pBluescript SK− (Staratgene), pOT2 (Berkely *Drosophila* Resource Center), pMT-DEST48 (Invitrogen) or the vector is a virus, for instance BaculoDirect (Invitrogen).

In some examples, the isolated recombinant nucleic acid also includes at least one additional sequence, such as one or more of (a) a regulatory sequence operatively coupled to the nucleic acid; (b) a selection marker operatively coupled to the nucleic acid; (c) a purification moiety operatively coupled to the nucleic acid; (d) a secretion sequence operatively coupled to the nucleic acid; and (e) a targeting sequence operatively coupled to the nucleic acid. In certain examples, the selection marker is ampicillin/carbenicillin resistance, kanamycin resistance, chloramphenicol resistance, tetracycline resistance or bancyclovir resistance.

Also provided are cells transformed with any of the isolated recombinant nucleic acid sequences described herein, for example a bacterial cell, a yeast cell, a fungal cell, an animal cell, or a plant cell. In specific examples, the cell is an *Escherichia coli* cell, an *Stenotrohomonas. maltophilia* cell, a *Kineococcus radiotolerans* cell, a cell from an organism belonging to the *Rhodococcus* genus, a cell from an organism belonging to the *Clostridium* genus, a cell from an organism belonging to the *Zymomonas* genus, a cell from an organism belonging to the *Klebsiella* genus, a cell from an organism belonging to the *Acinetobacter* genus, a cell from an organism belonging to the *Corynebacterium* genus, a cell from an organism belonging to the *Geobacillus* genus, a cell from an organism belonging to the *Proteus* genus, a cell from an organism belonging to the *Rhodobacter* genus, a cell from an organism belonging to the *Streptomyces* genus, a *Saccharomyces cerevisiae* cell, an *Aspergillus* cell, a *Trichoderma* cell, a *Neurospora* cell, a *Fusarium* cell, a *Chrysosporium* cell, a *Pichia* cell, a *Yarrowia* cell, a *Kluyveromyces* cell, a *Hansenula* cell, a *Schizosaccharomyces* cell, or a *Debaromyces* cell.

Also disclosed is a bacterial cell that includes a recombinant nucleic acid encoding one or more of (a) SEQ ID NO: 1 or 2 or (b) a sequence having at least 95% sequence identity with SEQ ID NO: 1 or 2. In certain examples, the cell expresses the protein sequence of: (a) SEQ ID NO: 1 or 2 or (b) a sequence having at least 95% sequence identity with SEQ ID NO: 1 or 2. In particular examples, the expressed protein is secreted by the cell, and in even more particular examples the expressed protein has oxidative decarbonylase activity.

Other embodiments of the disclosure include a method for producing a hydrocarbon. In one example, a method for producing a hydrocarbon includes culturing a transformed cell described herein under conditions permitting expression of a protein having oxidative decarbonylase activity. In some examples of the method, the protein having oxidative decarbonylase activity includes: (a) an amino acid sequence as set forth in SEQ ID NO: 1 or 2 or (b) a sequence having at least 95% sequence identity with SEQ ID NO: 1 or 2; or (c) a combination thereof. For instance, in certain examples, the cell expresses: SEQ ID NO: 1 and SEQ ID NO: 2. In certain examples, the method also includes isolating the hydrocarbon from the cell or from the medium in which the cell is cultured, and in other examples, the method includes culturing the cell in the presence of at least one substrate of oxidative decarbonylase activity, for instance in the presence of a fatty acid, a fatty acylCoA, NADPH, NADP and/or $O_2$.

In some examples, a method of producing a hydrocarbon includes culturing a cell that expresses a recombinant construct containing a promoter operably linked to a nucleic acid sequence, wherein the nucleic acid sequence encodes a protein comprising SEQ ID NO: 1 or 2 or a sequence having at least 95% sequence identity with SEQ ID NO: 1 or 2; under conditions wherein the cell expresses the protein, thereby producing the hydrocarbon. In particular examples, the protein has oxidative decarbonylase activity. In some examples, the promoter is a constitutive promoter or an inducible promoter, for instance an oenocyte-specific promoter or a T7 promoter. In some examples, the cell is a bacterial cell, for instance an *E. coli* cell, an *S. maltophilia* cell, a *K. radiotolerans* cell, a cell from an organism belonging to the *Rhodococcus* genus, a *Saccharomyces cerevisiae* cell, an *Aspergillus* cell, a *Trichoderma* cell, a *Neurospora* cell, a *Fusarium* cell, or a *Chrysosporium* cell. In still other examples, the method also includes isolating the hydrocarbon from the cell or from the medium in which the cell is cultured.

In another example, the method of producing a hydrocarbon includes methods of making hydrocarbons in vitro, or partially in vitro. For example, one or more of the peptides described herein can be isolated and then allowed to react with a substrate in vitro to make an intermediate that intermediate can then be added to a cell culture wherein the cells convert the intermediate to the desired product. In instances where the desired product is made entirely in vitro all of the necessary enzymes are reacted in vitro. However, the enzymes can be added sequentially or simultaneously and at various stages in the reaction, for example after intermediate purification or partial purification.

The present disclosure also provides for the use of the disclosed enzymes and hydrocarbons produced therefrom. One use of the disclosed enzymes is the production of synthetic hydrocarbon sex-pheromone components for *Musca domestica* control. Another use is the production of hydrocarbons as biofuels, either in vitro, or by inserting the isolated disclosed sequences, such as CYP4G2 (or related sequences, see Table A) into an organism (e.g., plant, bacteria, algae, etc.) in order to alter the hydrocarbon content, such as increasing the content, for production of fuel, lubricant, solvent, etc.

II. Abbreviations and Terms
CO: carbon monoxide
CYP4G1: cytochrome P450 4G1
CYP4G2: cytochrome P450 4G2
GC: gas chromatography
HC: hydrocarbon content
MS: mass spectrometry In order to facilitate review of the various embodiments of the disclosure, the following explanations of specific terms are provided:

Aldehyde: An organic compound containing a terminal carbonyl group including a carbon atom bonded to a hydrogen atom and double-bonded to an oxygen atom (chemical formula O═CH—).

Antibody: A protein (or protein complex) that includes one or more polypeptides substantially encoded by immunoglobulin genes or fragments of immunoglobulin genes. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The basic immunoglobulin (antibody) structural unit is generally a tetramer. Each tetramer is composed of two identical pairs of polypeptide chains, each pair having one "light" (about 25 kDa) and one "heavy" (about 50-70 kDa) chain. The N-terminus of each chain defines a variable region of about 100 to 110 or more amino acids primarily responsible for antigen recognition. The terms "variable light chain" ($V_L$) and "variable heavy chain" ($V_H$) refer, respectively, to these light and heavy chains.

As used herein, the term "antibody" includes intact immunoglobulins as well as a number of well-characterized fragments. For instance, Fabs, Fvs, and single-chain Fvs (SCFvs) that bind to target protein (or epitope within a protein or fusion protein) would also be specific binding agents for that protein (or epitope). These antibody fragments are as follows: (1) Fab, the fragment which contains a monovalent antigen-binding fragment of an antibody molecule produced by digestion of whole antibody with the enzyme papain to yield an intact light chain and a portion of one heavy chain; (2) Fab', the fragment of an antibody molecule obtained by treating whole antibody with pepsin, followed by reduction, to yield an intact light chain and a portion of the heavy chain; two Fab' fragments are obtained per antibody molecule; (3) (Fab')$_2$, the fragment of the antibody obtained by treating whole antibody with the enzyme pepsin without subsequent reduction; (4) F(ab')$_2$, a dimer of two Fab' fragments held together by two disulfide bonds; (5) Fv, a genetically engineered fragment containing the variable region of the light chain and the variable region of the heavy chain expressed as two chains; and (6) single chain antibody, a genetically engineered molecule containing the variable region of the light chain, the variable region of the heavy chain, linked by a suitable polypeptide linker as a genetically fused single chain molecule. Methods of making these fragments are routine (see, e.g., Harlow and Lane, *Using Antibodies: A Laboratory Manual*, CSHL, New York, 1999).

Antibodies for use in the methods and compositions of this disclosure can be monoclonal or polyclonal. These antibodies can be prepared by methods known to those of skill in the art, including as described herein (see Example Section below). Merely by way of example, monoclonal antibodies can be prepared from murine hybridomas according to the classical method of Kohler and Milstein (*Nature* 256:495-97, 1975) or derivative methods thereof. Detailed procedures for monoclonal antibody production are described in Harlow and Lane, *Using Antibodies: A Laboratory Manual*, CSHL, New York, 1999.

Bacteria: As used herein, both Archaea and Eubacteria are encompassed by the term "bacteria." The term "Eubacteria" refers to prokaryotic organisms that are distinguishable from Archaea. Similarly, "Archaea" refers to prokaryotes that are distinguishable from Eubacteria. Eubacteria and Archaea can be distinguished by a number morphological and biochemical criteria known in the art. For example, differences in ribosomal RNA sequences, RNA polymerase structure, the presence or absence of introns, antibiotic sensitivity, the presence or absence of cell wall peptidoglycans and other cell wall components, the branched versus unbranched structures of membrane lipids, and the presence/absence of histones and histone-like proteins are used to assign an organism to Eubacteria or Archaea.

Examples of Eubacteria include, but are not limited to, members of the phyla Acidobacteria, Actinobacteria, Aquificae, Bacteroidetes, Chlamydiae, Chlorobi, Chloroflexi Chrysiogenetes, Cyanobacteria, Deferribacteres, Deinococcus, Thermus, Dictyoglomi, Fibrobacteres, Firmicutes, Fusobacteria, Gemmatimonadetes, Lentisphaerae, Nitrospira, Planctomycetes, Proteobacteria, Spirochaetes, Tenericutes, Thermodesulfobacteria, Thermomicrobia, Thermotogae, and Verrucomicrobia. Specific, non-limiting examples of Eubacteria include *Escherichia coli, Thermus thermophilus, Stenotrophomonas maltophilia, Kineococcus radiotolerans* and *Bacillus stearothermophilus*. Example of Archaea include *Methanococcusjannaschii, Methanosarcina mazei, Methanobacterium thermoautotrophicum, Methanococcus maripaludis, Methanopyrus kandleri, Halobacterium* such as *Haloferax volcanii* and *Halobacterium* species NRC-i, *Archaeoglobusfulgidus, Pyrococcus fit riosus, Pyrococcus horikoshii, Pyrobaculum aerophilum, Pyrococcus abyssi, Sulfolobus solfataricus, Sulfolobus tokodaii, Aeuropyrum pernix, Thermoplasma acidophilum,* and *Thermoplasma volcanium*. Other specific examples of Eubacteria can be found at world wide web address bacterio.cict.fr/classifphyla.html (last accessed on Nov. 17, 2009).

Biodiesel fuels: A diesel-equivalent processed fuel derived from biological sources which can be used in unmodified diesel-engine vehicles. Biodiesels are attractive for fuels, and some other uses, because they have a low vapor pressure, are non-toxic and are stable, as per HMIS regulation, and do not deteriorate or detonate upon mild heating. Chemically, biodiesels are generally defined as the mono alkyl esters of long chain fatty acids derived from renewable lipid sources.

Biofuel: Any fuel that derives from biomass—recently living organisms or their metabolic byproducts, such as manure from cows. A biofuel may be further defined as a fuel derived from a metabolic product of a living organism. It is a renewable energy source, unlike other natural resources such as petroleum, coal and nuclear fuels.

Conditions that permit production: Any fermentation or culturing conditions that allow a microorganism to produce a desired product, such as a hydrocarbon or hydrocarbon intermediate. Such conditions usually include temperature ranges, levels of aeration, and media selection that, when combined, allow the microorganism to grow. Exemplary mediums include broths or gels. Generally, the medium includes a carbon source (such as glucose, fructose, cellulose, or the like) that can be metabolized by the microorganism directly, or enzymes can be used in the medium to facilitate metabolizing the carbon source. To determine if culture conditions permit product production, the microorganism can be cultured for 2, 4, 6, 8, 12, 24, 36, 48 or 72 hours and a sample can be obtained and analyzed. For example, the cells in the sample or the medium in which the cells were grown can be tested for the presence of the desired product. When testing for the presence of a product, assays can be used, such as those provided herein, including those presented in the Examples below.

Contacting: Placement in direct physical association; includes both in solid and liquid form. Contacting includes contact between one molecule and another molecule. Contacting can occur in vitro with isolated cells or tissue or in vivo by administering it to an organism.

Cytochrome P450: A very large and diverse superfamily of hemoproteins found in all domains of life. Cytochromes P450 use a plethora of both exogenous and endogenous compounds as substrates in enzymatic reactions. Usually they form part of multi-component electron transfer chains, called P450-containing systems. The most common reaction catalysed by cytochrome P450 is a monooxygenase reaction, e.g. insertion of one atom of oxygen into an organic substrate (RH) while the other oxygen atom is reduced to water: $RH+O_2+2H++2e^- \rightarrow ROH+H_2O$.

Cytochrome P450 enzymes have been identified from all lineages of life, including mammals, birds, fish, insects, worms, sea squirts, sea urchins, plants, fungi, slime molds, bacteria and archaea. More than 8100 distinct cytochrome P450 sequences are known. Exemplary cytochrome P450s are described herein and provided in the attached Sequence listings. In particular examples, exemplary cytochrome P450s include CYP4G1 (SEQ ID NO: 2) and CYP4G2 (SEQ ID NO: 1).

Decarbonylase: An enzyme that catalyses the decarboxylation of aldehydes to form carbon monoxide and hydrocarbons. Differs from an oxidative decarbonylase in that an oxidative decarbonylase catalyses the conversion of aldehydes to carbon dioxide and hydrocarbons.

Decarboxylase: An enzyme that hydrolyzes a carboxyl radical.

Deoxyribonucleic acid (DNA): A long chain polymer that includes the genetic material of most living organisms (some viruses have genes including ribonucleic acid, RNA). The repeating units in DNA polymers are four different nucleotides, each of which includes one of the four bases, adenine, guanine, cytosine and thymine bound to a deoxyribose sugar to which a phosphate group is attached. Triplets of nucleotides, referred to as codons, in DNA molecules code for amino acid in a peptide. The term codon is also used for the corresponding (and complementary) sequences of three nucleotides in the mRNA into which the DNA sequence is transcribed.

Encode: As used herein, the term "encode" refers to any process whereby the information in a polymeric macromolecule or sequence is used to direct the production of a second molecule or sequence that is different from the first molecule or sequence. As used herein, the term is construed broadly, and can have a variety of applications. In some aspects, the term "encode" describes the process of semi-conservative DNA replication, where one strand of a double-stranded DNA molecule is used as a template to encode a newly synthesized complementary sister strand by a DNA-dependent DNA polymerase.

In another aspect, the term "encode" refers to any process whereby the information in one molecule is used to direct the production of a second molecule that has a different chemical nature from the first molecule. For example, a DNA molecule can encode an RNA molecule (for instance, by the process of transcription incorporating a DNA-dependent RNA polymerase enzyme). Also, an RNA molecule can encode a peptide, as in the process of translation. When used to describe the process of translation, the term "encode" also extends to the triplet codon that encodes an amino acid. In some aspects, an RNA molecule can encode a DNA molecule, for instance, by the process of reverse transcription incorporating an RNA-dependent DNA polymerase. In another aspect, a DNA molecule can encode a peptide, where it is understood that "encode" as used in that case incorporates both the processes of transcription and translation.

Endogenous: As used herein with reference to a nucleic acid molecule and a particular cell or microorganism, the term endogenous refers to a nucleic acid sequence or peptide that is in the cell and was not introduced into the cell using recombinant engineering techniques. For example, a gene that was present in the cell when the cell was originally isolated from nature.

Exogenous: As used herein with reference to a nucleic acid molecule and a particular cell, the term exogenous refers to any nucleic acid molecule that does not originate from that particular cell as found in nature. Thus, a non-naturally-occurring nucleic acid molecule is considered to be exogenous to a cell once introduced into the cell. A nucleic acid molecule that is naturally-occurring also can be exogenous to a particular cell.

Fermentation Broth: Any medium that supports microorganism life (for instance, a microorganism that is actively metabolizing carbon). A fermentation medium usually contains a carbon source. The carbon source can be anything that can be utilized, with or without additional enzymes, by the microorganism for energy.

Fungi: A kingdom of eukaryotic organisms. They are heterotrophic and digest their food externally, absorbing nutrient molecules into their cells. Yeasts, molds, and mushrooms are examples of fungi. The major phyla of fungi include Chytridiomycota, Zygomycota, Glomeromycota, Ascomycota, and Basidiomycota.

The Chytridiomycota are commonly known as chytrids. These fungi produce zoospores that are capable of moving on their own through liquid menstrua by simple flagella. The Zygomycota are known as zygomycetes and reproduce sexually with meiospores called zygospores and asexually with sporangiospores. *Rhizopus stolonifer, Pilobolus, Mucor, Rhizomucor*, and *Rhizopus* are Zygomycota.

Specific, non-limiting examples of fungi that are useful in the disclosed methods include *Saccharomyces cerevisiae, Aspergillus, Trichoderma, Neurospora, Fusarium*, and *Chrysosporium*.

Gene expression: The process by which the coded information of a nucleic acid transcriptional unit (including, for example, genomic DNA or cDNA) is converted into an operational, non-operational, or structural part of a cell, often including the synthesis of a protein. Gene expression can be influenced by external signals; for instance, exposure of a cell, tissue or subject to an agent that increases or decreases gene expression. Expression of a gene also can be regulated anywhere in the pathway from DNA to RNA to protein. Regulation of gene expression occurs, for instance, through controls acting on transcription, translation, RNA transport and processing, degradation of intermediary molecules such as mRNA, or through activation, inactivation, compartmentalization or degradation of specific protein molecules after they have been made, or by combinations thereof. Gene expression can be measured at the RNA level or the protein level and by any method known in the art, including, without limitation, Northern blot, RT-PCR, Western blot, or in vitro, in situ, or in vivo protein activity assay(s).

Hydrocarbon: A chemical compound that contains the elements carbon (C) and hydrogen (H). All hydrocarbons have a carbon backbone and hydrogen atoms attached to that backbone. Sometimes, the term is used as a shortened form of the term "aliphatic hydrocarbon." There are essentially three types of hydrocarbons: (1) aromatic hydrocarbons, which have at least one aromatic ring; (2) saturated hydrocarbons, also known as alkanes, which lack double, triple or aromatic bonds; and (3) unsaturated hydrocarbons, which have one or more double or triple bonds between carbon atoms, are divided into: alkenes, alkynes, and dienes. Liquid geologically-extracted hydrocarbons are referred to as petroleum (literally "rock oil") or mineral oil, while gaseous geologic hydrocarbons are referred to as natural gas. All are significant sources of fuel and raw materials as a feedstock for the production of organic chemicals and are commonly found in the earth's subsurface using the tools of petroleum geology. Oil reserves in sedimentary rocks are the principal source of hydrocarbons for the energy and chemicals industries. Hydrocarbons are of interest because they encompass the constituents of the major fossil fuels (coal, petroleum, natural gas, for instance, and biofuels, as well as plastics, waxes, solvents and oils).

Hydrocarbon-forming oxidative decarbonylase activity: The activity of one or more peptides that causes the conversion of an aldehyde to a hydrocarbon, with the release of $CO_2$. Examples of enzymes having oxidative decarbonylase activity include those with an amino acid sequence provided by SEQ ID NO: 1 or 2 or having at least 70% sequence identity to SEQ ID NO: 1 or 2, such as at least 80%, at least 90%, at least 95% sequence identity to SEQ ID NO: 1 or 2. Other examples of enzymes with oxidative decarbonylase activities are provided in Table A or peptides known to have cytochrome P450 activity. The term "oxidative decarbonylase activity" is used interchangeably herein with the term "hydrocarbon-forming oxidative-decarbonylase activity." Oxidative decarbonylase activity can be tested methods known to those of ordinary skill in the art including, but not limited to those, provided in the Examples below.

Isolated: An "isolated" biological component (such as a nucleic acid molecule, peptide, or cell) has been substantially purified away from other biological components in a mixed sample (such as a cell extract). For example, an "isolated" peptide or nucleic acid molecule is a peptide or nucleic acid molecule that has been separated from the other components of a cell in which the peptide or nucleic acid molecule was present (such as an expression host cell for a recombinant peptide or nucleic acid molecule). The term "isolated nucleic acid" thus encompasses nucleic acids purified by standard nucleic acid purification methods. The term also embraces nucleic acids prepared by recombinant expression in a host cell, as well as chemically synthesized nucleic acids.

Label: A detectable compound or composition that is conjugated directly or indirectly to another molecule to facilitate detection of that molecule. Specific, non-limiting examples of labels include fluorescent tags, enzymatic linkages, and radioactive isotopes. In some examples, a disclosed polypeptide is labeled with a detectable label.

Microorganism: A member of the prokaryotic or eukaryotic microbial species from the domains Archaea, Bacteria, and Eucarya, the latter including yeast and filamentous fungi, protozoa, algae, or higher Protista. The terms "microbial cells" and "microbes" are used interchangeably with the term microorganism.

Nucleic acid molecule: A polymeric form of nucleotides, which can include both sense and anti-sense strands of RNA, cDNA, genomic DNA, and synthetic forms and mixed polymers of the above. A nucleotide refers to a ribonucleotide, deoxynucleotide or a modified form of either type of nucleotide. A "nucleic acid molecule" as used herein is synonymous with "nucleic acid" and "polynucleotide." A nucleic acid molecule is usually at least 10 bases in length, unless otherwise specified. The term includes single- and double-stranded forms of DNA. A nucleic acid molecule can include either or both naturally occurring and modified nucleotides linked together by naturally occurring and/or non-naturally occurring nucleotide linkages.

Nucleic acid molecules can be modified chemically or biochemically or can contain non-natural or derivatized nucleotide bases, as will be readily appreciated. Such modifications include, for example, labels, methylation, substitution of one or more of the naturally occurring nucleotides with an analog, internucleotide modifications, such as uncharged linkages (for example, methyl phosphonates, phosphotriesters, phosphoramidates, carbamates, etc.), charged linkages (for example, phosphorothioates, phosphorodithioates, etc.), pendent moieties (for example, peptides), intercalators (for example, acridine, psoralen, etc.), chelators, alkylators, and modified linkages (for example, alpha anomeric nucleic acids, etc.). The term "nucleic acid molecule" also includes any topological conformation, including single-stranded, double-stranded, partially duplexed, triplexed, hairpinned, circular and padlocked conformations.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame. Configurations of separate genes that are transcribed in tandem as a single messenger RNA are denoted as operons. Thus, placing genes in close proximity, for example in a plasmid vector, under the transcriptional regulation of a single promoter, constitutes a synthetic operon.

Optional or optionally: A term to describe a subsequently described event or circumstance can but need not occur, and that the description includes instances where said event or circumstance occurs and instances where it does not.

Oxidative decarbonylation: A process that involves the removal of a carbonyl carbon of a fatty aldehyde as $CO_2$. In one example, this process is catalyzed by a hydrocarbon-forming oxidative decarbonylase enzyme (referred to as oxidative decarbonylase), such as any of those disclosed herein.

Peptide: Any compound composed of amino acids, amino acid analogs, chemically bound together. Peptide as used herein includes oligomers of amino acids, amino acid analog, or small and large peptides, including polypeptides or proteins. Any chain of amino acids, regardless of length or post-translational modification (such as glycosylation or phosphorylation). In one example, a peptide is two or more amino acids joined by a peptide bond.

"Peptide" applies to amino acid polymers to naturally occurring amino acid polymers and non-naturally occurring amino acid polymer as well as in which one or more amino acid residue is a non-natural amino acid, for example a artificial chemical mimetic of a corresponding naturally occurring amino acid.

A "polypeptide" is a polymer in which the monomers are amino acid residues which are joined together through amide bonds. When the amino acids are alpha-amino acids, either the L-optical isomer or the D-optical isomer can be used. The terms "polypeptide" or "protein" as used herein are intended to encompass any amino acid sequence and include modified sequences such as glycoproteins. The term "polypeptide" is specifically intended to cover naturally occurring proteins, as well as those which are recombinantly or synthetically produced. The term "residue" or "amino acid residue" includes reference to an amino acid that is incorporated into a protein, polypeptide, or peptide.

As used herein, the term "polypeptide fragment" refers to a portion of a polypeptide which exhibits at least one useful epitope or functional domain. Polypeptide fragments contemplated herein include all fragments of a polypeptide that retain a particular desired activity of the polypeptide. Biologically functional fragments can vary in size and will depend on the polypeptide of interest.

The term "soluble" refers to a form of a polypeptide that is not inserted into a cell membrane.

Conservative amino acid substitutions are those substitutions that, when made, least interfere with the properties of the original protein, that is, the structure and especially the function of the protein is conserved and not significantly changed by such substitutions. Examples of conservative substitutions are shown below.

| Original Residue | Conservative Substitutions |
|---|---|
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Conservative substitutions generally maintain (a) the structure of the polypeptide backbone in the area of the substitution, for example, as a sheet or helical conformation, (b) the charge or hydrophobicity of the molecule at the target site, or (c) the bulk of the side chain.

The substitutions which in general are expected to produce the greatest changes in protein properties will be non-conservative, for instance changes in which (a) a hydrophilic residue, for example, seryl or threonyl, is substituted for (or by) a hydrophobic residue, for example, leucyl, isoleucyl, phenylalanyl, valyl or alanyl; (b) a cysteine or proline is substituted for (or by) any other residue; (c) a residue having an electropositive side chain, for example, lysyl, arginyl, or histadyl, is substituted for (or by) an electronegative residue, for example, glutamyl or aspartyl; or (d) a residue having a bulky side chain, for example, phenylalanine, is substituted for (or by) one not having a side chain, for example, glycine.

Plant: any living stage or form of any member of the plant kingdom including, but not limited to, eukaryotic algae, mosses, club mosses, ferns, angiosperms, gymnosperms, and lichens (which contain algae) including any parts (for instance, pollen, seeds, cells, tubers, stems) thereof.

Plasmid: A DNA molecule separate from chromosomal DNA and capable of autonomous replication. It is typically circular and double-stranded, and usually occurs in bacteria, and sometimes in eukaryotic organisms (for instance, the 2-micrometre-ring in *Saccharomyces cerevisiae*). The size of plasmids can vary from 1 to over 400 kilobase pairs. Plasmids often contain genes or gene cassettes that confer a selective advantage to the bacterium (or other cell) harboring them, such as the ability to make the bacterium (or other cell) antibiotic resistant.

Plasmids contain at least one DNA sequence that serves as an origin of replication, which enables the plasmid DNA to be duplicated independently from the chromosomal DNA. The chromosomes of most bacteria are circular, but linear plasmids are also known.

Plasmids used in genetic engineering are referred to as vectors. They can be used to transfer genes from one organism to another, and typically contain a genetic marker conferring a phenotype that can be selected for or against. Most also contain a polylinker or multiple cloning site, which is a short region containing several commonly used restriction sites allowing the easy insertion of DNA fragments at this location. Specific, non-limiting examples of plasmids include pOT2 (Berkeley *Drosophila* Resource Center, Berkeley, Calif.), pMT-DEST48 (Invitrogen, Carlsbad, Calif.).

Primers: Short nucleic acids, for example DNA oligonucleotides 10 nucleotides or more in length, which are annealed to a complementary target DNA strand by nucleic acid hybridization to form a hybrid between the primer and the target DNA strand, then extended along the target DNA strand by a DNA polymerase enzyme. Primer pairs can be used for amplification of a nucleic acid sequence, for instance using the polymerase chain reaction (PCR) or other nucleic-acid amplification methods known in the art.

Probes and primers as used herein typically include, for example, at least 12 contiguous nucleotides of a known sequence. In order to enhance specificity, longer probes and primers also can be employed, such as probes and primers that include at least 15, 20, 30, 40, 50, or more consecutive nucleotides of the disclosed nucleic acid sequences.

Methods for preparing and using probes and primers are described, for example Sambrook et al., *Molecular Cloning: A Laboratory Manual,* 3rd ed., vol. 1-3, Cold Spring Harbor, N.Y., 2000; Ausubel et al., *Current Protocols in Molecular Biology,* Greene Publ. Assoc. & Wiley-Intersciences, 1987; Innis et al., *PCR Protocols, A Guide to Methods and Applications,* 1990. PCR primer pairs can be derived from a known sequence, for example, by using computer programs intended for that purpose such as Primer (Version 0.5, 1991, Whitehead Institute for Biomedical Research, Cambridge, Mass.).

Probe: An isolated nucleic acid attached to a detectable label or reporter molecule. Typical labels include radioactive isotopes, ligands, chemiluminescent agents, fluorophores, and enzymes.

Promoter: A region of DNA that generally is located upstream (within the 5' flanking region of a gene) that is needed for transcription. Promoters permit the proper activation or repression of the gene which they control. A promoter contains specific sequences that are recognized by transcription factors. These factors bind to the promoter DNA sequences and result in the recruitment of RNA polymerase, the enzyme that synthesizes the RNA from the coding region of the gene.

Purified: The term purified does not require absolute purity; rather, it is intended as a relative term. Thus, for example, a purified hydrocarbon preparation is one in which the product is more concentrated than the product is in its environment within a cell. For example, a purified hydrocarbon is one that is substantially separated from cellular components (nucleic acids, lipids, carbohydrates, and peptides) that can accompany it. In another example, a purified hydrocarbon preparation is one in which the hydrocarbon is substantially-free from contaminants, such as those that might be present following fermentation.

In one example, a hydrocarbon is purified when at least about 50% by weight of a sample is composed of the hydrocarbon, for example when at least about 60%, 70%, 80%, 85%, 90%, 92%, 95%, 98%, or 99% or more of a sample is composed of the hydrocarbon.

Recombinant nucleic acid: A nucleic acid sequence that is not naturally occurring or has a sequence that is made by an artificial combination of two otherwise separated segments of sequence, or that is placed next to a non-native DNA sequence, for example a nucleic acid sequence that is integrated into another host's chromosome. This artificial combination is often accomplished by chemical synthesis or, more commonly, by the artificial manipulation of isolated segments of nucleic acids, for instance by genetic engineering techniques such as those described in Sambrook et al., *Molecular Cloning: A Laboratory Manual,* 3rd ed., vol. 1-3, Cold Spring Harbor, N.Y., 2000. The term recombinant includes nucleic acids that have been altered solely by addition, substitution, or deletion of a portion of the nucleic acid. Frequently, a recombinant nucleic acid can include a nucleic acid sequence operably linked to a promoter sequence. Such a recombinant nucleic acid can be part of a vector, used to transform a cell.

Reporter: An agent that can be used to identify and/or select target components of a system of interest. For example, a reporter can include a protein, for instance, an enzyme, that confers antibiotic resistance or sensitivity (for instance, 3-lactamase, chloramphenicol acetyltransferase (CAT), and the like), a fluorescent screening marker (for instance, green fluorescent protein (GFP), YFP, EGFP, RFP, etc.), a luminescent marker (for instance, a firefly luciferase protein), an affinity based screening marker, or positive or negative selectable marker genes such as lacZ, 3-gal/lacZ (13-galactosidase), ADH (alcohol dehydrogenase), his3, ura3, leu2, lys2, or the like.

A reporter gene is a nucleic acid sequence that encodes an easily assayed product (for instance firefly luciferase, CAT, and β-galactosidase), whose presence can be assayed. A reporter gene can be operably linked to a regulatory control sequence and transduced into cells. If the regulatory control sequence is transcriptionally active in a particular cell type, the reporter gene product normally will be expressed in such cells and its activity can be measured using techniques known in the art. The activity of a reporter gene product can be used, for example, to assess the transcriptional activity of an operably linked regulatory control sequence. In addition, the ability to produce hydrocarbons can be assayed for in a small scale experiment in which disclosed oxidative decarbonylase genes can be used themselves as reporters of their own activity.

Sequence identity: The similarity between two nucleic acid sequences or between two amino acid sequences is expressed in terms of the level of sequence identity shared between the sequences. Sequence identity is typically expressed in terms of percentage identity; the higher the percentage, the more similar the two sequences.

Methods for aligning sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene* 73:237-244, 1988; Higgins & Sharp, *CABIOS* 5:151-153, 1989; Corpet et al., *Nucleic Acids Research* 16:10881-10890, 1988; Huang, et al., *CABIOS* 8:155-165, 1992; and Pearson et al., *Methods in Molecular Biology* 24:307-331, 1994. Altschul et al., *J. Mol. Biol.* 215: 403-410, 1990, presents a detailed consideration of sequence alignment methods and homology calculations.

The NCBI Basic Local Alignment Search Tool (BLAST™; Altschul et al., *J. Mol. Biol.* 215:403-410, 1990) is available from several sources, including the National Center for Biotechnology Information (NBCI, Bethesda, Md.), for use in connection with the sequence analysis programs blastp, blastn, blastx, tblastn and tblastx. BLAST™ can be accessed on the internet at the NBCI website. As used herein, sequence identity is commonly determined with the BLAST™ software set to default parameters. For instance, blastn (version 2.0) software can be used to determine sequence identity between two nucleic acid sequences using default parameters (expect=10, matrix=BLOSUM62, filter=DUST (Tatusov and Lipmann, in preparation as of Dec. 1, 1999; and Hancock and Armstrong, *Comput. Appl. Biosci.* 10:67 70, 1994), gap existence cost=11, per residue gap cost=1, and lambda ratio=0.85). For comparison of two polypeptides, blastp (version 2.0) software can be used with default parameters (expect 10, filter=SEG (Wootton and Federhen, *Computers in Chemistry* 17:149-163, 1993), matrix=BLOSUM62, gap existence cost=11, per residue gap cost=1, lambda=0.85).

For comparisons of amino acid sequences of greater than about 30 amino acids, the "Blast 2 sequences" function of the BLAST™ program is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 35%, at least 45%, at least 50%, at least 60%, at least 80%, at least 85%, at least 90%, at least 95%, at least 98%, or at least 99% sequence identity to SEQ ID NO: 1 or 2.

For comparisons of nucleic acid sequences, the "Blast 2 sequences" function of the BLAST™ (Blastn) program is employed using the default BLOSUM62 matrix set to default parameters (cost to open a gap [default=11]; cost to extend a gap [default=1]; expectation value (E) [default=10.0]; word size [default=11]; number of one-line descriptions (V) [default=100]; number of alignments to show (B) [default=100]).

Substrate: As used herein, a substrate is a compound suitable to be used as the starting chemical in an enzymatic reaction. Typically the chemical formed by the enzymatic reaction is termed a product (products and substrates can also be termed intermediates). Specific, non-limiting examples of substrates that can be used with the disclosed methods include fatty acids, acyl CoAs, acyl ACPs, acyl AMP, and hydrocarbon intermediates.

Transduction: The process by which genetic material, for instance, DNA or another nucleic acid molecule, is inserted into a cell. Common transduction techniques include the use of viral vectors (including bacteriophages), electroporation, and chemical reagents that increase cell permeability. Transfection and transformation are other terms for transduction, although these sometimes imply expression of the genetic material as well. The term transformed refers to a cell into which a nucleic acid molecule has been introduced by molecular biology techniques. The term encompasses all techniques by which a nucleic acid molecule might be introduced into such a cell, including transformation with plasmid vectors (for example, by electroporation, conjugation, transduction, or natural transformation), transfection with viral vectors, and introduction of naked DNA by electroporation, natural transformation, lipofection, and particle gun acceleration.

Vector: A nucleic acid molecule capable of transporting a non-vector nucleic acid sequence that has been introduced into the vector. One type of vector is a "plasmid," which refers to a circular double-stranded DNA into which non-plasmid DNA segments can be ligated. Other vectors include cosmids, bacterial artificial chromosomes (BAC) and yeast artificial chromosomes (YAC). Another type of vector is a viral vector, wherein additional DNA segments can be ligated into all or part of the viral genome. Certain vectors are capable of autonomous replication in a host cell into which they are introduced (for example, vectors having a bacterial origin of replication replicate in bacteria hosts). Other vectors can be integrated into the genome of a host cell upon introduction into the host cell and are replicated along with the host genome. Some vectors contain expression control sequences (such as promoters) and are capable of directing the transcription of an expressible nucleic acid sequence that has been introduced into the vector. Such vectors are referred to as "expression vectors." A vector can also include one or more selectable marker genes and/or genetic elements known in the art.

Unless otherwise explained, all technical and scientific terms used herein have the same meaning as commonly understood by one of ordinary skill in the art to which this disclosure belongs. In case of conflict, the present specification, including explanations of terms, will control. The singular terms "a," "an," and "the" include plural referents unless context clearly indicates otherwise. Similarly, the word "or" is intended to include "and" unless the context clearly indicates otherwise. The term "comprising" means "including;" hence, "comprising A or B" means including A or B, as well as A and B together. All numerical ranges given herein include all values, including end points (unless specifically excluded) and any and all intermediate ranges between the endpoints.

Suitable methods and materials for the practice and testing of the disclosure are described below. However, the provided materials, methods, and examples are illustrative only and are not intended to be limiting. Accordingly, except as otherwise noted, the methods and techniques of the present disclosure can be performed according to methods and materials similar or equivalent to those described and/or according to conventional methods well known in the art and as described in various general and more specific references that are cited and discussed throughout the present specification (see, for instance, Sambrook et al., Molecular Cloning: A Laboratory Manual, 3rd ed., Cold Spring Harbor Laboratory Press, 2000; Ausubel et al., Current Protocols in Molecular Biology, Greene Publishing Associates, 1992 (and Supplements to 2000); Ausubel et al., Short Protocols in Molecular Biology: A Compendium of Methods from Current Protocols in Molecular Biology, 4th ed., Wiley & Sons, 1999).

III. Oxidative decarbonylases and Methods of Their Use to Produce Hydrocarbons

Disclosed is the surprising identification of cytochrome P450 enzymes that function as aldehyde oxidative decarbonylases and are involved in the biosynthesis of hydrocarbons. Microorganisms (for instance fungal or bacterial cells) transformed with one or more of the genes that encodes one or more of these enzymes can be used as a source for hydrocarbons. Such a novel, renewable source of hydrocarbons is desirable because it provides a supplement to the existing limited resources of non-renewable hydrocarbons. As such, this discovery provides methods of producing hydrocarbons that can be used for the production of a wide range of products, such as hydrocarbon sex-pheromone components for *Musca domestica* control, biofuels, lubricants, or solvents. In use, a cell (such as a bacterial cell or a fungal cell) is transformed with one or more of these genes or their homologs, and the cell is then cultured under conditions that permit the generation of specific hydrocarbon species.

A. Isolated Polypeptides and Polynucleotides

1. Structure

Polynucleotides and polypeptides were isolated from *Musca domestica* and identified to be involved in the biosynthesis of hydrocarbons. For example, such polypeptides were determined to be cytochrome P450 enzymes that possess oxidative decarbonylase activity. In one particular example, isolated polypeptide sequences with oxidative decarbonylase activity are provided, such as isolated polypeptide sequences with an amino acid sequence as set forth in SEQ ID NO: 1 or 2. In another particular example, isolated polynucleotides that encode sequences with oxidative decarbonylase activity are provided, such as encode a polypeptide with an amino acid sequence set forth in SEQ ID NO: 1 or 2. These polypeptide and nucleic acid sequences are listed in the accompanying Sequence Listing. One of ordinary skill in the art will appreciate that by using the information provided herein relating to the structure and function of the *M. domestica* sequences, other sequences having similar activity to the CYP4G2 and CYP4G1 can be obtained. For example, the present disclosure also relates to sequences similar to CYP4G2. For example, CYP4G2v1 is curated in GenBank as accession No. EF615002 (incorporated by reference in its entirety as available on GenBank on Nov. 17, 2009; Zhu et al., 2009, *BMC Physiol.* 8:18). Notably, Zhu et al. do not identify the CYP4G2v1 sequence as an oxidative decarbonylase. Rather, Zhu et al. imply that CYP4G2v1 is involved in permethrin metabolism. Additional related sequences include sequence 46640 (GenBank Accession No. AAU65695, incorporated by reference in its entirety as available on GenBank on Nov. 17, 2009) from U.S. Pat. No. 6,703,491, which has an E value of 6e-82 with CYP4G2, with an E value of 6e-82. Sequence 46640 encodes a portion of CYP4G15 from *Drosophila melanogaster*.

Oxidative decarbonylase activity can reasonably be expected to be found in all insects. Similar activities likely also exist in some bacteria, plants, algae, and birds that synthesize hydrocarbons. BLASTP searches comparing CYP4G2 and CYP4G1 against known sequences in GenBank returned highly significant hits to uncharacterized P450s in many insects, invertebrates, vertebrates, and plants (as provided in Table A below).

Definitively predicting oxidative decarbonylase activity for other P450s can be difficult. In some cases, minor amino acid changes can affect P450 activity. Also, P450 enzymes can show some sequence divergence. It is suggested that the more closely related the insects are taxonomically, the more common motifs they should have.

In the case of oxidative decarbonylase, sequences with the strongest "E-value" scores from BLASTP surveys of GenBank are expected to show the greatest degree of similarity. The E-value represents the probability that an observed alignment resulted by random chance; thus, the smaller the E-value, the more confident one can be that the alignment represents related sequences. The best possible E-value is 0.0. These sequences have the highest probability of encoding oxidative decarbonylase enzymes; indeed, CYP9T1 falls into this category.

In Table A, the BLASTP hits with 0.0 E-values are sequences from *Drosophila* spp. An alignment shows these sequences have 48.6% a.a. identity, and 98.6% a.a. similarity. The weakest insect hit is 8E-82 ($8 \times 10^{-82}$). This is still very high, particularly for P450 sequences. When all the insect sequences are aligned, they have 23.7% identity and 77% similarity, with identical positions pretty much scattered throughout the sequences. If plant P450s are included (by restricting a blastp search to just plants) the best hits are significantly weaker than the insect sequences, and when all insect and plant hits are aligned, identity falls to 0.6%, and similarity is 58.6%.

Assuming that all or most of the sequences in Table A represent hydrocarbon decarbonylases, the portions of each protein responsible for activity; i.e. which amino acids determine the substrate binding site(s), can be determined. For example, a molecular model of CYP4G13 can be used to locate residues in channels. Similar models can be constructed for CYP4G2. Similarly, some of the weaker blastp hits in Table A can be reasonably assumed not to be hydrocarbon decarbonylases because of their expression pattern, etc.

TABLE A

Additional examples of oxidative decarbonylase enzymes.

| | Score | E Value |
|---|---|---|
| *Musca domestica* [flies] taxid 7370 | | |
| gb|ABV48808.1|cytochrome P450 CYP4G2v1 [*Musca domestica*] | 1148 | 0.0 |
| gb|AAK40120.1|cytochrome P450 CYP4G13v2 [*Musca domestica*] | 709 | 0.0 |
| *Drosophila erecta* [flies] taxid 7220 | | |
| ref|XP_001982391.1|GG12761 [*Drosophila erecta*] | 825 | 0.0 |
| gb|EDV45360.1|GG12761 [*Drosophila erecta*] | 825 | 0.0 |
| *Drosophila melanogaster* [flies] taxid 7227 | | |
| ref|NP_525031.1|Cytochrome P450-4g1 CG3972-PA [*Drosophila* ... | 825 | 0.0 |
| sp|Q9V3S0|CP4G1_DROME Cytochrome P450 4g1 (CYPIVG1) | 825 | 0.0 |
| emb|CAA15672.1|EG: 165H7.1 [*Drosophila melanogaster*] | 825 | 0.0 |
| gb|AAF45503.1|CG3972-PA [*Drosophila melanogaster*] | 825 | 0.0 |
| gb|ABY20430.1|GH01123p [*Drosophila melanogaster*] | 825 | 0.0 |
| *Drosophila simulans* [flies] taxid 7240 | | |
| ref|XP_002076787.1|GD24639 [*Drosophila simulans*] | 824 | 0.0 |
| gb|EDX16353.1|GD24639 [*Drosophila simulans*] | 824 | 0.0 |
| *Drosophila yakuba* [flies] taxid 7245 | | |
| ref|XP_002099674.1|GE16587 [*Drosophila yakuba*] | 824 | 0.0 |
| gb|EDX00782.1|GE16587 [*Drosophila yakuba*] | 824 | 0.0 |
| *Drosophila pseudoobscura pseudoobscura* [flies] taxid 46245 | | |
| ref|XP_001354787.1|GA17813 [*Drosophila pseudoobscura* pseu ... | 823 | 0.0 |
| gb|EAL31842.1|GA17813 [*Drosophila pseudoobscura* pseudoobs ... | 823 | 0.0 |
| *Drosophila mojavensis* [flies] taxid 7230 | | |
| ref|XP_002011612.1|GI11123 [*Drosophila mojavensis*] | 818 | 0.0 |
| gb|EDW05602.1|GI11123 [*Drosophila mojavensis*] | 818 | 0.0 |
| *Drosophila virilis* [flies] taxid 7244 | | |
| ref|XP_002058244.1|GJ15981 [*Drosophila virilis*] | 816 | 0.0 |
| gb|EDW66352.1|GJ15981 [*Drosophila virilis*] | 816 | 0.0 |
| *Drosophila ananassae* [flies] taxid 7217 | | |
| ref|XP_001964253.1|GF20812 [*Drosophila ananassae*] | 813 | 0.0 |
| gb|EDV34702.1|GF20812 [*Drosophila ananassae*] | 813 | 0.0 |
| *Drosophila grimshawi* [flies] taxid 7222 | | |
| ref|XP_001992189.1|GH24346 [*Drosophila grimshawi*] | 798 | 0.0 |
| gb|EDV91896.1|GH24346 [*Drosophila grimshawi*] | 798 | 0.0 |
| *Drosophila willistoni* [flies] taxid 7260 | | |
| ref|XP_002071182.1|GK25658 [*Drosophila willistoni*] | 769 | 0.0 |
| gb|EDW82168.1|GK25658 [*Drosophila willistoni*] | 769 | 0.0 |
| *Culex quinquefasciatus* [flies] taxid 7176 | | |
| ref|XP_001869039.1|cytochrome P450 4g15 [*Culex quinquefas* ... | 585 | 2e-165 |
| gb|EDS28283.1|cytochrome P450 4g15 [*Culex quinquefasciatus*] | 585 | 2e-165 |
| ref|XP_001851084.1|cytochrome P450 4g15 [*Culex quinquefas* ... | 532 | 3e-149 |
| gb|EDS33030.1|cytochrome P450 4g15 [*Culex quinquefasciatus*] | 532 | 3e-149 |
| *Aedes aegypti* [flies] taxid 7159 | | |
| ref|XP_001658068.1|cytochrome P450 [*Aedes aegypti*] | 585 | 3e-165 |
| ref|XP_001659149.1|cytochrome P450 [*Aedes aegypti*] | 585 | 5e-165 |
| ref|XP_001648376.1|cytochrome P450 [*Aedes aegypti*] | 523 | 1e-146 |
| *Nasonia vitripennis* [wasps &c.] taxid 7425 | | |
| ref|XP_001600301.1|PREDICTED: similar to cytochrome P450 ... | 574 | 8e-162 |
| ref|XP_001606417.1|PREDICTED: similar to cytochrome P450 ... | 528 | 6e-148 |
| *Chironomus tentans* [flies] taxid 7153 | | |
| gb|AAW78325.1|cytochrome P450 family 4 [*Chironomus tentans*] | 568 | 4e-160 |
| *Anopheles gambiae* str. PEST [flies] taxid 180454 | | |
| ref|XP_555875.3|AGAP000877-PA [*Anopheles gambiae* str. PEST] | 561 | 7e-158 |
| gb|EAL39767.3|AGAP000877-PA [*Anopheles gambiae* str. PEST] | 561 | 7e-158 |
| ref|XP_558699.5|AGAP001076-PA [*Anopheles gambiae* str. PEST] | 524 | 8e-147 |
| gb|EAL40625.3|AGAP001076-PA [*Anopheles gambiae* str. PEST] | 524 | 8e-147 |
| *Tribolium castaneum* (rust-red flour beetle) [beetles] taxid 7070 | | |
| ref|NP_001107860.1|cytochrome P450 monooxygenase CYP4G7 [ ... | 551 | 5e-155 |
| ref|NP_001107791.1|cytochrome P450 monooxygenase [*Triboli* ... | 531 | 7e-149 |

TABLE A-continued

Additional examples of oxidative decarbonylase enzymes.

| | Score | E Value |
|---|---|---|
| *Bombyx mori* (silk moth, . . . ) [moths] taxid 7091 | | |
| ref|NP_001106221.1|cytochrome P450 [*Bombyx mori*] | 550 | 1e−154 |
| gb|ABF51451.1|cytochrome P450 [*Bombyx mori*] | 550 | 1e−154 |
| ref|NP_001106223.1|cytochrome P450 CYP4G25 [*Bombyx mori*] | 506 | 2e−141 |
| gb|ABF51415.1|cytochrome P450 CYP4G25 [*Bombyx mori*] | 506 | 2e−141 |
| *Leptinotarsa decemlineata* [beetles] taxid 7539 | | |
| gb|AAZ94273.1|cytochrome P450 [*Leptinotarsa decemlineata*] | 543 | 1e−152 |
| *Drosophila sechellia* [flies] taxid 7238 | | |
| ref|XP_002044080.1|GM13084 [*Drosophila sechellia*] | 529 | 2e−148 |
| gb|EDW51392.1|GM13084 [*Drosophila sechellia*] | 529 | 2e−148 |
| ref|XP_002040228.1|GM19042 [*Drosophila sechellia*] | 427 | 1e−117 |
| gb|EDW43699.1|GM19042 [*Drosophila sechellia*] | 427 | 1e−117 |
| *Apis mellifera* (bee, . . . ) [bees] taxid 7460 | | |
| ref|NP_001035323.1|cytochrome P450 monooxygenase [*Apis me* . . . | 528 | 4e−148 |
| gb|ABB36785.1|cytochrome P450 monooxygenase [*Apis mellifera*] | 528 | 4e−148 |
| *Blattella germanica* [roaches] taxid 6973 | | |
| gb|AAO20251.1|cytochrome P450 monooxygenase CYP4G19 [*Blat* . . . | 521 | 9e−146 |
| *Ips paraconfusus* [beetles] taxid 89938 | | |
| gb|ABF06553.1|CYP4G27 [*Ips paraconfusus*] | 517 | 1e−144 |
| *Antheraea yamamai* (oak silkmoth, . . . ) [moths] taxid 7121 | | |
| dbj|BAD81026.1|cytochrome P450 CYP4G25 [*Antheraea yamamai*] | 507 | 1e−141 |
| *Mamestra brassicae* [moths] taxid 55057 | | |
| gb|AAR26517.1|antennal cytochrome P450 CYP4 [*Mamestra* bra . . . | 502 | 3e−140 |
| *Acyrthosiphon pisum* [aphids] taxid 7029 | | |
| ref|XP_001944205.1|PREDICTED: similar to cytochrome P450 . . . | 484 | 6e−135 |
| *Drosophila persimilis* [flies] taxid 7234 | | |
| ref|XP_002023479.1|GL20168 [*Drosophila persimilis*] | 429 | 4e−118 |
| gb|EDW27627.1|GL20168 [*Drosophila persimilis*] | 429 | 4e−118 |
| *Blaberus discoidalis* [roaches] taxid 6981 | | |
| sp|P29981|CP4C1_BLADI Cytochrome P450 4C1 (CYPIVC1) | 352 | 5e−95 |
| gb|AAA27819.1|cytochrome P450 | 352 | 5e−95 |
| *Carcinus maenas* (common shore crab) [crustaceans] taxid 6759 | | |
| pir||JC8026 cytochrome P450 enzyme, CYP4C39 enzyme - green . . . | 339 | 4e−91 |
| gb|AAQ93010.1|cytochrome P450 CYP4C39 [*Carcinus maenas*] | 339 | 4e−91 |
| *Branchiostoma floridae* [lancelets] taxid 7739 | | |
| gb|EEA69963.1|hypothetical protein BRAFLDRAFT_57954 [Bran . . . | 328 | 5e−88 |
| gb|EEA70036.1|hypothetical protein BRAFLDRAFT_210358 [Bra . . . | 322 | 7e−86 |
| *Balaenoptera acutorostrata* (lesser rorqual) [whales & dolphins] taxid 9767 | | |
| dbj|BAF64512.1|cytochrome 4V6 [*Balaenoptera acutorostrata*] | 322 | 5e−86 |
| *Helicoverpa zea* (tomato fruitworm, ...) [moths] taxid 7113 | | |
| gb|AAM54722.1|cytochrome P450 monooxygenase CYP4M6 [Helic . . . | 322 | 6e−86 |
| *Daphnia magna* [crustaceans] taxid 35525 | | |
| dbj|BAF35771.1|cytochrome P450 4 family [*Daphnia magna*] | 321 | 1e−85 |
| *Nilaparvata lugens* [bugs] taxid 108931 | | |
| emb|CAQ57675.1|cytochrome P450 [*Nilaparvata lugens*] | 313 | 2e−83 |
| emb|CAQ57674.1|cytochrome P450 [*Nilaparvata lugens*] | 308 | 8e−82 |
| *Danio rerio* (leopard danio, . . . ) [bony fishes] taxid 7955 | | |
| ref|NP_001073465.1|hypothetical protein LOC562008 [*Danio* . . . | 313 | 2e−83 |
| gb|AAI25941.1|Zgc: 154042 [*Danio rerio*] | 313 | 2e−83 |
| *Arabidopsis thaliana* (thale-cress, . . . ) [eudicots] taxid 3702 | | |
| ref|NP_198661.1|CYP735A1 (cytochrome P450, family 735, su . . . | 144 | 1e−33 |
| dbj|BAB09357.1|cytochrome P450-like protein [*Arabidopsis* . . . | 144 | 1e−33 |
| emb|CAB10290.1|cytochrome P450 like protein [*Arabidopsis* . . . | 131 | 1e−29 |
| emb|CAB78553.1|cytochrome P450 like protein [*Arabidopsis* . . . | 131 | 1e−29 |

TABLE A-continued

Additional examples of oxidative decarbonylase enzymes.

| | Score | E Value |
|---|---|---|
| *Oryza sativa Indica* Group (Indian rice) [monocots] taxid 39946 | | |
| gb|EAZ07069.1|hypothetical protein OsI_028301 [*Oryza* sati . . . | 144 | 1e−33 |
| gb|EAY75510.1|hypothetical protein OsI_003357 [*Oryza* sati . . . | 137 | 2e−33 |
| gb|EAY75509.1|hypothetical protein OsI_003356 [*Oryza* sati . . . | 137 | 2e−31 |
| gb|EAY84668.1|hypothetical protein OsI_005901 [*Oryza* sati . . . | 136 | 4e−31 |

Given these teachings, one of ordinary skill in the art will appreciate that sequences similar to CYP4G1 and CYP4G2 can readily be cloned and used to make hydrocarbons and hydrocarbon intermediates. Therefore, throughout this description reference to CYP4G1 and CYP4G2 should be understood to mean all proteins displaying the respective activity (as well as all polynucleotides encoding such proteins), including, for example those in Table A, the Examples as well as others that can be identified or engineered through various molecular techniques such as antibody binding, nucleic acid hybridization, PCR and the like.

Although particular embodiments of hydrocarbon and hydrocarbon intermediate forming sequences are disclosed, it will be understood that sequences that have similar structural characteristics can be isolated from other microorganisms. These newly isolated sequences can be assayed for oxidative decarbonylase activity (see Table A for list of specific, non-limiting examples of related sequences) by methods known to those of skill in the art including those disclosed herein (such as in the Examples). In addition, it will be understood that other functionally equivalent forms of the sequences disclosed herein can be readily identified and/or generated using conventional molecular biological techniques, including for instance site-directed mutagenesis or M13 primer mutagenesis. Details of these techniques are provided in Sambrook et al., *Molecular Cloning: A Laboratory Manual*, 3rd ed., vol. 1-3, Cold Spring Harbor, N.Y., 2000, Ch. 15. Thus, in addition to structurally related sequences and homologous sequences, the disclosure also encompasses amino acid sequences that have at least 30%, 35%, 40%, 45%, 50%, 55%, 60%, 70%, 75%, 80%, 85%, 90%, 95%, 96%, 97%, 98% or 99% sequence identity with SEQ ID NOs: 1 and 2, for instance at least 95%, 96%, 97%, 98%, or 99% sequence identity. Moreover, the disclosure also encompasses nucleic acid sequences that encode polypeptides that have at least 30%, 35%, 40%, 45%, 50%, 55%, 60%, 70%, 75%, 80%, 85%, 90%, 95%, 96%, 97%, 98% or 99% sequence identity with SEQ ID NOs: 1 and 2, for instance at least 95%, 96%, 97%, 98%, or 99% sequence identity.

Sequences retaining structural and functional similarity to CYP4G1 and CYP4G2 can be identified by any of a number of known methods. One such method involves the screening of genomic sequences for sequence alignment with the known sequence(s). Methods for aligning sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene* 73:237-244, 1988; Higgins & Sharp, *CABIOS* 5:151-153, 1989; Corpet et al., *Nucleic Acids Research* 16:10881-10890, 1988; Huang, et al., *CABIOS* 8:155-165, 1992; and Pearson et al., *Methods in Molecular Biology* 24:307-331, 1994. Altschul et al., *J. Mol. Biol.* 215:403-410, 1990, presents a detailed consideration of sequence alignment methods and homology calculations.

When a genomic sequence is not available for a particular species of interest, related sequences can be amplified from total RNA using RT-PCR. Briefly, total RNA is extracted from the cells of interest by any one of a variety of well known methods. Sambrook et al., *Molecular Cloning: A Laboratory Manual*, 3rd ed., vol. 1-3, Cold Spring Harbor, N.Y., 2000, and Ausubel et al. (In Current Protocols in Molecular Biology, Greene Publ. Assoc. and Wiley-Intersciences, 1992) provide descriptions of methods for RNA isolation. Generally, any microorganism can be used as a source of such RNA. The extracted RNA is then used as a template for performing reverse transcription-polymerase chain reaction (RT-PCR) amplification of cDNA. Methods and conditions for RT-PCR are described in Kawasaki et al., (In PCR Protocols, A Guide to Methods and Applications, Innis et al. (eds.), 21-27, Academic Press, Inc., San Diego, Calif., 1990).

The selection of amplification primers will be made according to the particular cDNA that is to be amplified. Variations in amplification conditions can be required to accommodate primers and amplicons of differing lengths and composition; such considerations are well known in the art and are discussed for instance in Innis et al. (PCR Protocols, A Guide to Methods and Applications, Academic Press, Inc., San Diego, Calif., 1990).

Sequencing of PCR products obtained by these amplification procedures can be used to facilitate confirmation of the amplified sequence and provide information about natural variation of this sequence in different species. Oligonucleotides derived from the provided CYP4G1 and CYP4G2 sequences can be used in such sequencing methods. Closely related orthologous CYP4G1 and CYP4G2 molecules can share at least 30%, 35%, 40%, 45%, 50%, 55%, 60%, 65%, 70%, 75%, 80%, 85%, 90%, 95%, or at least 98% sequence identity with the disclosed CYP4G1 and CYP4G2 sequences (see, the sequence listing).

2. Function

Hydrocarbons and intermediates thereof can be formed by expressing one or more of the disclosed polypeptides in a host cell, such as *E. coli*. Therefore, *E. coli*, or other organisms that naturally or are engineered to make hydrocarbons such as *S. maltophilia*, *C. aggregans* or *X. axonopodis*, can be used to determine the oxidative decarbonylase activity of a specific protein. Briefly, the protein to be tested, for example a sequence similar to CYP4G2, is expressed in a host that is known to display oxidative decarbonylase activity. The CYP4G2-like sequence is deemed to be active (i.e. have oxidative decarbonylase activity) if the host produces or increases production of hydrocarbons, such as an increase of at least 10%, at least 20%, at least 50%, or at least 90%.

Production hosts can be engineered using the peptides disclosed herein to produce hydrocarbons and hydrocarbon intermediates having defined structural characteristics (degrees of branching, saturation, and length). One method of making hydrocarbon intermediates involves expressing, increasing the expression of, or expressing more active forms of, one or more enzymes having oxidative decarbonylase activity. Exemplary enzymes that can be manipulated to increase hydrocarbon production include CYP4G1 and CYP4G2, as well as other enzymes that increase or modify fatty acid production. One of ordinary skill in the art will appreciate that the products produced from such enzymes vary with the acyl chain of the substrate.

There are several methods of identifying peptides having hydrogen decarboxylase activity. Product (hydrocarbon) formation using one or more of these methods indicates that the peptide has dehydrogenase activity. For example, the peptide can be expressed from an exogenous nucleic acid sequence in a cell and then a cell lysate can be prepared. Various substrates such as NADPH and/or NADH can be added to the lysate and products can be detected using the GC/MS methods described herein (see, Examples below). In another example, the peptide can be purified and incubated with cell lysate from a cell that is not expressing the peptide (herein after wild-type lysate). The purified peptide, wild-type lysate and various substrates can be incubated and the resulting products can be characterized using the methods described herein. Peptides having oxidative decarbonylase activity are identified as those that produce hydrocarbons. One of ordinary skill in the art will appreciate that when a cell lysate is used that already contains hydrocarbon products, peptides having decarboxylase activity will be recognized by an increase in hydrocarbon production compared to the lysate without the addition of substrate.

B. Recombinant Nucleic Acid Constructs

Also disclosed herein are recombinant nucleic acid constructs that include one or more nucleic acid sequences encoding CYP4G1 or CYP4G2; homologs of SEQ ID NO: 1 or 2; conservative variants of SEQ ID NO: 1 or 2 (including those provided in the Examples below); and/or sequences having at least 50% sequence identity, such as at least 60%, at least 70%, at least 80%, at least 90%, at least 95%, or at least 99% (such as about 80%, about 85%, about 90%, about 95%, about 96%, about 97%, about 98% or about 99%) with SEQ ID NO: 1 or 2 or those provided in Table A. Exemplary recombinant nucleic acid constructs of use include cloning vectors, expression vectors or synthetic operons. A cloning vector is a self-replicating DNA molecule that serves to transfer a DNA segment into a host cell. Three common types of cloning vectors are bacterial plasmids, phages, and other viruses. An expression vector is a cloning vector designed so that a coding sequence inserted at a particular site will be transcribed and translated into a protein. A synthetic operon is a fragment of DNA encoding the gene of interest flanked by promoter regions and regions that will allow integration into a heterologous host.

Both cloning and expression vectors contain nucleotide sequences that allow the vectors to replicate in one or more suitable host cells. In cloning vectors, this sequence is generally one that enables the vector to replicate independently of the host cell chromosomes, and also includes either origins of replication or autonomously replicating sequences. Various bacterial and viral origins of replication are well known and include, but are not limited to, the pBR322 plasmid origin and the SV40, polyoma, adenovirus, VSV and BPV viral origins.

The nucleic acid sequences disclosed herein can be used to produce proteins by the use of recombinant expression vectors containing the sequence(s). A great variety of expression vectors can be used, for instance chromosomal, episomal and virus-derived vectors, including vectors derived from bacterial plasmids, from bacteriophage, from yeast episomes, from yeast chromosomal elements, from viruses such as baculoviruses, papoviruses such as SV40, vaccinia viruses, adenoviruses, fowl pox viruses; pseudorabies viruses and retroviruses, and vectors derived from combinations thereof, such as those derived from plasmid and bacteriophage genetic elements, such as cosmids and phagemids. Generally, any vector suitable to maintain, propagate or express polynucleotides to express a polypeptide in a host cell can be used for expression in this regard. Therefore, any other vector that is replicable and viable in the host cell can be used.

The appropriate DNA sequence is inserted into the vector by any of a variety of well-known and routine techniques. In general, a DNA sequence for expression is joined to an expression vector by cleaving the DNA sequence and the expression vector with one or more restriction endonucleases and then joining the restriction fragments together using T4-DNA ligase. Procedures for restriction and ligation are well known. Suitable procedures in this regard, and for constructing expression vectors using alternative techniques, which also are well known, are set forth in great detail in Sambrook et al. (2000); Ausubel et al. (1995).

In an expression vector, the sequence of interest is operably linked to a suitable regulatory sequence, expression control sequence or promoter recognized by the host cell to direct mRNA synthesis. Promoters are untranslated sequences located generally within 100 to 1000 base pairs upstream from the start codon of a structural gene that regulate the transcription and translation of nucleic acid sequences under their control. Promoters are generally either inducible or constitutive.

Inducible promoters are promoters that initiate increased levels of transcription from DNA under their control in response to some change in the environment, for instance the presence or absence of a nutrient or a change in temperature. Constitutive promoters, in contrast, maintain a relatively constant level of transcription. In addition, useful promoters can also confer appropriate cellular and temporal specificity. Such promoters include those that are developmentally-regulated and/or cell-specific.

A nucleic acid sequence is operably linked to another nucleic acid sequence when it is placed into a functional relationship with the other nucleic acid sequence. For example, DNA for a presequence or secretory leader is operatively linked to DNA for a polypeptide if it is expressed as a preprotein that participates in the secretion of the polypeptide; a promoter is operably linked to a coding sequence if it affects the transcription of the sequence; or a ribosome binding site is operably linked to a coding sequence if it is positioned so as to facilitate translation. Generally, operably linked sequences are contiguous and, in the case of a secretory leader, contiguous and in reading frame.

Linking is achieved by conventional techniques such as SOE PCR, DNA synthesis, blunt end ligation, or ligation at restriction enzyme sites. If suitable restriction sites are not available, then synthetic oligonucleotide adapters or linkers can be used (Sambrook et al., 2000; Ausubel et al., 1995).

It will be recognized that numerous promoters are functional in bacterial cells, and have been described in the literature, including constitutive, inducible, developmentally regulated, and environmentally regulated promoters. Of particular interest is the use of promoters (also referred to as transcriptional initiation regions) functional in the appropriate microbial host cell. For example if *E. coli* is used as a host cell then exemplary promoters that can be used include the phage lambda PL promoter, the *E. coli* lac, trp and tac promoters, the SV40 early and late promoters, promoters of retroviral LTRs, the CaMV 35S promoter, coconut foliar decay virus (CFDV) DNA (U.S. Pat. No. 6,303,345), and the endogenous promoters of *P. citrorellolis*. If *Saccharomyces cerevisiae* is the host then the sequences of interest are under the control of yeast promoters. A specific, non-limiting example of a useful yeast promoter includes the GAL/CYC promoter. It will be understood that numerous promoters that are not mentioned are suitable for use and are well known, and can be readily employed in the manner illustrated herein. Other promoters known to control the expression of genes in prokaryotic or eukaryotic cells can be used. Expression vectors can also contain a ribosome binding site for translation initiation, and a transcription terminator. The vector can also contain sequences useful for the amplification of gene expression.

Expression and cloning vectors can and usually do contain a structural gene or selection marker having the necessary regulatory regions for expression in a host cell and providing for selection of transformant cells. The gene can provide for resistance to a cytotoxic agent, for instance an antibiotic, heavy metal, or toxin, complementation providing prototrophy to an auxotrophic host, viral immunity or the like. Depending upon the number of different host species into which the expression construct or components thereof are introduced, one or more markers can be employed, where different conditions for selection are used for the different hosts.

Specific, non-limiting examples of suitable selection markers include genes that confer resistance to bleomycin, gentamycin, glyphosate, hygromycin, kanamycin, methotrexate, nalidixic acid, phleomycin, phosphinotricin, spectinomycin, streptomycin, sulfonamide, sulfonylureas, ampicillin/carbenicillin, chloramphenicol, or streptomycin/spectinomycin, and tetracycline. Specific, non-limiting examples of markers include, but are not limited to, alkaline phosphatase (AP), myc, hemagglutinin (HA), 13 glucuronidase (GUS), luciferase, and green fluorescent protein (GFP).

In addition, expression vectors also can contain marker sequences operatively linked to a nucleotide sequence for a protein that encodes an additional protein used as a marker. The result is a hybrid or fusion protein comprising two linked and different proteins. The marker protein can provide, for example, an immunological or enzymatic marker for the recombinant protein produced by the expression vector. Additionally, the end of the polynucleotide can be modified by the addition of a sequence encoding an amino acid sequence useful for purification of the protein produced by affinity chromatography. Various methods have been devised for the addition of such affinity purification moieties to proteins. Representative examples can be found in U.S. Pat. Nos. 4,703,004, 4,782,137, 4,845,341, 5,935,824, and 5,594,115. Any method known in the art for the addition of nucleotide sequences encoding purification moieties can be used, for example those contained in Innis et al. (1990) and Sambrook et al. (2000).

More particularly, the present disclosure includes recombinant constructs that include one or more isolated nucleic acid sequences that encode CYP4G1 (SEQ ID NO: 2) or CYP4G2 (SEQ ID NO: 1) or variants and homologs of these sequences. The constructs can include a vector, such as a plasmid or viral vector, into which the sequence has been inserted, either in the forward or reverse orientation. The recombinant construct can further include a regulatory sequence, including for example, a promoter operatively linked to the sequence. Large numbers of suitable vectors and promoters are known and are commercially available. In one embodiment, the pET-21b(+), pCOLADuet-1, pCDFDuet-1, pcDNA3.1(+), and/or pCMV SPORT6.1 (Invitrogen) vectors are used. It will be understood however, that other plasmids or vectors can be used as long as they are replicable and viable or capable of expressing the encoded protein in the host. It will also be understood that recombinant DNA technology resulting in the integration of the respective DNA sequences encoding for CYP4G1 (SEQ ID NO: 2) or CYP4G2 (SEQ ID NO: 1) and/or variants and homologs of these sequences into the chromosome of any living organism can result in expression and production of the proteins.

The polynucleotide sequence also can be part of an expression cassette that at a minimum includes, operably linked in the 5' to 3' direction, a promoter, one or more nucleic acids of the present disclosure, and a transcriptional termination signal sequence functional in a host cell. The promoter can be of any of the types discussed herein, for example, an inducible promoter or constitutive promoter, and the expression cassette can further include an operably linked targeting sequence, or transit or secretion peptide coding region capable of directing transport of the protein produced. The expression cassette can also further include a nucleotide sequence encoding a selectable marker and/or a purification moiety.

C. Host Cells

Host cells (for instance, bacterial, fungal eukaryotic, plant, or algae cells) are provided that are genetically engineered (for instance, transformed, transduced or transfected) with one or more nucleic acid molecules encoding one or more of CYP4G1 (SEQ ID NO: 2) or CYP4G2 (SEQ ID NO: 1) or a variant or homolog of one or more of these sequences. These sequences can be expressed from vector constructs or directly from the chromosome after gene integration or from extrachromosomal arrays. For example, an CYP4G1 (SEQ ID NO: 2) or CYP4G2 (SEQ ID NO: 1) protein is operably linked to gene expression control elements that are functional in the desired host cell, for instance a T7 promoter in *E. coli*.

Methods of expressing proteins in heterologous expression systems are well known in the art. Typically a bacterial or yeast host cell is transformed by natural transformation, electroporation, conjugation of transduction to contain the expression construct either extrachromosomally as with a plasmid on integrated into the chromosome after recombination. In eukaryotic cells, typically, a host cell is transfected with (or infected with a virus containing) an expression vector using any method suitable for the particular host cell. Such transfection methods are also well known in the art and non limiting exemplary methods are described herein. The transfected (also called, transformed) host cell is capable of expressing the protein encoded by the corresponding nucleic acid sequence in the expression cassette. Transient or stable transfection of the host cell with one or more expression vectors is contemplated by the present disclosure.

Many different types of cells can be used to express heterologous proteins provided herein, such as bacteria, yeasts, fungi, algae, insects, vertebrate cells (such as mammalian cells), and plant cells, including (as appropriate) primary cells and immortal cell lines. Numerous representatives of each cell type are commonly used and are available from a wide variety of commercial sources, including, for example, ATCC, Pharmacia, and Invitrogen.

Various yeast strains and yeast derived vectors are used commonly for the expression of heterologous proteins. For instance, specific, non-limiting examples of suitable yeast cells include *Saccharomyces cerevisiae* cells, *Aspergillus* cells, *Trichoderma* cells, *Neurospora* cells, *Fusarium* cells, or a *Chrysosporium* cells. In one specific, non-limiting example, *Pichia pastoris* expression systems, obtained from Invitrogen (Carlsbad, Calif.), can be used to express a CYP4G1 (SEQ ID NO: 2) or CYP4G2 (SEQ ID NO: 1) peptide. Such systems include suitable *Pichia pastoris* strains, vectors, reagents, transformants, sequencing primers, and media. Available strains include KM71H (a prototrophic strain), SMD1168H (a prototrophic strain), and SMD1168 (a pep4 mutant strain) (Invitrogen, Carlsbad, Calif.).

*Saccharomyces cerevisiae* is another commonly used yeast. The plasmid YRp7 (Stinchcomb et al., *Nature,* 282:39, 1979; Kingsman et al., *Gene,* 7:141, 1979; Tschemper et al., *Gene,* 10:157, 1980) is commonly used as an expression vector in *Saccharomyces*. This plasmid contains the trp1 gene that provides a selection marker for a mutant strain of yeast lacking the ability to grow in tryptophan, such as strains ATCC No. 44,076 and PEP4-1 (Jones, *Genetics,* 85:12, 1977). The presence of the trp1 lesion as a characteristic of the yeast host cell genome then provides an effective environment for detecting transformation by growth in the absence of tryptophan.

Yeast host cells can be transformed using the polyethylene glycol method, as described by Hinnen (*Proc. Natl. Acad. Sci. USA,* 75:1929, 1978). Additional yeast transformation protocols are set forth in Gietz et al. (*Nucl. Acids Res.,* 20(17):1425, 1992) and Reeves et al. (FEMS, 99(2-3):193-197, 1992).

In the construction of suitable expression vectors, the termination sequences associated with these genes are also ligated into the expression vector 3' of the sequence desired to be expressed to provide polyadenylation of the mRNA and termination. Any plasmid vector containing a yeast-compatible promoter capable of transcribing a nucleic acid sequence encoding a prokaryotic tRNA, an origin of replication, and a termination sequence, is suitable.

Other suitable host cells are bacterial cells. Specific, non-limiting examples of suitable bacterial phyla include Acidobacteria, Actinobacteria, Aquificae, Bacteroidetes, Chlamydiae, Chlorobi, Chloroflexi Chrysiogenetes, Cyanobacteria, Deferribacteres, Deinococcus, Thermus, Dictyoglomi, Fibrobacteres, Firmicutes, Fusobacteria, Gemmatimonadetes, Lentisphaerae, Nitrospira, Planctomycetes, Proteobacteria, Spirochaetes, Tenericutes, Thermodesulfobacteria, Thermomicrobia, Thermotogae, and Verrucomicrobia. Specific, non-limiting examples bacterial species of use include *Escherichia coli, Thermus thermophilus, Stenotrophomonas maltophilia, Kineococcus radiotolerans Bacillus stearothermophilus, Methanococcus jannaschii, Methanosarcina mazei, Methanobacterium thermoautotrophicum, Methanococcus maripaludis, Methanopyrus kandleri, Halobacterium* such as *Haloferax volcanii* and *Halobacterium* species NRC-i, *Archaeoglobusfulgidus, Pyrococcus fit riosus, Pyrococcus horikoshii, Pyrobaculum aerophilum, Pyrococcus abyssi, Sulfolobus solfataricus, Sulfolobus tokodaii, Aeuropyrum pernix, Thermoplasma acidophilum,* and *Thermoplasma volcanium*. In one specific, non-limiting embodiment, the host cell is an *E. coli* cell, a *S. maltophilia* cell, a *Pseudomonas* species cell, a *Bacillus* sp. cell or an actinomycetes cell or cells belonging to the genus *Rhodococcus* genus. Introduction of the construct into the host cell can be accomplished by a variety of methods including calcium phosphate transfection, DEAE-dextran mediated transfection, polybrene mediated transfection, protoplast fusion, liposome mediated transfection, conjugation, natural transformation, electroporation, and other methods known in the art.

Still other suitable host cells are plant cells, including, but not limited to species of eukaryotic algae, mosses, club mosses, ferns, angiosperms, gymnosperms, and lichens. Any known method can be employed for plant cell transformation, culture, and regeneration can be employed. Methods for introduction of foreign DNA into plant cells include, but are not limited to: transfer involving the use of *Agrobacterium tumefaciens* and appropriate Ti vectors, including binary vectors; chemically induced transfer (for instance, with polyethylene glycol); biolistics; and microinjection. See, for instance, An et al., *Plant Molecular Biology Manual* A3:1-19, 1988. Various promoters suitable for expression of heterologous genes in plant cells are known in the art, including constitutive promoters, for instance, the cauliflower mosaic virus (CaMV) 35S promoter, which is expressed in many plant tissues, organ- or tissue-specific promoters, and promoters that are inducible by chemicals such as methyl jasminate, salicylic acid, or safeners, for example.

Host cells are grown under appropriate conditions to a suitable cell density. If the sequence of interest is operably linked to an inducible promoter, the appropriate environmental alteration is made to induce expression. If the product (for instance the hydrocarbon) accumulates in the host cell, the cells are harvested by, for example, centrifugation or filtration. Whole cell extractions can be performed to purify the hydrocarbon products from the whole cells. If the host cells secrete the product into the medium, the cells and medium are separated and the medium retained for purification of the desired product.

D. Product Production and Uses Thereafter

The disclosure provides methods of making hydrocarbons. Various production hosts are provided that can be used to produce products having engineered carbon chain lengths, saturation sites, and branch points. Methods of making such products are also provided as well as methods of further modifying the products, such as through cracking, to create high quality biofuels and specialty chemicals. For example, the present disclosure also provides for the use of the disclosed enzymes and hydrocarbons produced therefrom. One use is the production of hydrocarbons as biofuels, either in vitro, or by inserting the isolated disclosed sequences, such as CYP4G2 (or related sequences, see Table A) into an organism (e.g., plant, bacteria, algae, etc.) as described in detail herein in order to alter the hydrocarbon content, such as increasing the content, for production of fuel, lubricant, solvent, etc.

Another use of the disclosed enzymes is the production of synthetic hydrocarbon sex-pheromone components for *Musca domestica* control. For example, lures or traps may be baited with synthetic hydrocarbon sex-pheromones to attract *Musca domestica*

1. Carbon Chain Characteristics

The hydrocarbons can be engineered to have specific carbon chain characteristics by expressing various enzymes or attenuating the expression of various enzymes in the production host. For example, carbon chain length can be controlled by expressing various thioesterases in the production host while attenuating the expression of endogenous thioesterases. Similarly, various branch points can be introduced into the carbon chain by expressing various bkd genes, and the degree of saturation can also be controlled by expressing various genes for example by over-expressing fabB.

2. Methods of Making Hydrocarbons

One of ordinary skill in the art will appreciate that hydrocarbons can be produced using in vitro reactions, including chemical or enzymatic conversions as well as through in vivo reactions. Additionally, a combination of in vivo and in vitro conversions can be used. Moreover, specific hydrocarbons can be produced by selectively providing selected fatty acids, acyl-ACP, acyl-CoA, or aliphatic ketones (in the instance where the product desired is a specific hydrocarbon).

The term "convert" refers to the use of either chemical means or polypeptides in a reaction which changes a first intermediate to a second intermediate. The term "chemical conversion" refers to reactions that are not actively facilitated by polypeptides. The term "biological conversion" refers to reactions that are actively facilitated by peptides. Conversions can take place in vivo or in vitro. When biological conversions are used the peptides and/or cells can be immobilized on supports such as by chemical attachment on polymer supports. The conversion can be accomplished using any reactor known to one of ordinary skill in the art, for example in a batch or a continuous reactor.

a. In Vitro

Given the disclosure provided herein, large scale enzyme production of the peptides CYP4G1 (SEQ ID NO: 2) or CYP4G2 (SEQ ID NO: 1) and homologues, variants thereof is now possible. Briefly, the coding sequences from anyone of these peptides or homologues of these peptides can be cloned into a high expression plasmid such as pET-21B(+) or pCO-LADuet-1 (EMD Chemicals, Inc., Germany) and the plasmid can be induced. The resulting peptides can then be purified and used in batch production.

When in vitro methods are used, the peptides supplied to the reaction will depend upon the starting material. For example, when a hydrocarbon is desired and the starting material is acyl-ACP, a thioesterase and appropriate co-reactants can be added in conjunction with CYP4G1 (SEQ ID NO: 2) or CYP4G2 (SEQ ID NO: 1) peptides.

Additionally, a combination of chemical conversions and biological conversions can be used to produce a desired product. For example, one of ordinary skill in the art will appreciate that two fatty acids can be condensed to make an aliphatic ketone via chemical conversion and the resulting aliphatic ketone can then be converted a hydrocarbon using biological conversions.

b. In Vivo

Given the disclosure provided herein, hydrocarbons can be produced in a recombinant cell. The recombinant cell can produce one or more CYP4G1 (SEQ ID NO: 2) or CYP4G2 (SEQ ID NO: 1) and related sequences thereof (see Table A). One of ordinary skill in the art will appreciate that the choice of peptides to express in the recombinant cell will depend upon the desired product and the starting material provided to the cells. The in vivo methods described herein can also be used in combination with chemical conversions and in vitro biological conversions. The disclosure allows for the large scale production of hydrocarbons that have defined carbon chain lengths, saturation levels, and branch points. The production of such engineered molecules provides a diversity of products that can be used a fuels, and specialty chemicals.

3. Post Production Processing

The generated hydrocarbons can be subjected to cracking to convert the high molecular weight carbon chains (for example, about $C_{22}$ to about $C_{36}$) to lower molecular weight hydrocarbons (for example, about $C_1$ to about $C_{18}$). In particular, the cracking can selectively target the double bond positions for cleavage in the feedstock. For example, a $C_{26}$ hydrocarbon with a single internal double bond can be cleaved to make two products, such as a $C_{12}$ alkane and a $C_{1-4}$ alkane. In some examples, any unsaturated hydrocarbon, especially a $C_{14}$ to $C_{20}$ hydrocarbon is cracked to make an octane, nonane, etc. These are especially useful for producing high value products for jet fuel (for instance, $C_{14}$ to $C_{18}$), diesel (for instance, $C_8$ to $C_{14}$), and gasoline (for instance, $C_5$ to $C_{10}$). Any of the methods of thermal cracking, hydrocracking, and catalytic cracking known to those of skill in the art can be used to further modify the products produced.

The disclosure is illustrated by the following non-limiting Examples.

EXAMPLES

Example 1

CYP4G1 is a Oxidative Decarbonylase

This example shows that CYP4G1 is a cytochrome P450 that functions as a oxidative decarbonylase.

CYP4G1 (Flybase I.D. CG3972; GenBank Accession Nos. NM080292 and AAF45503 each of which is herein incorporated by reference in its entirety) is a fruitfly (*Drosophila melanogaster*) cytochrome P450 that is most similar (71.7% identity and 81.8% similarity at the amino acid level) to CYP4G2 of any known sequence. To date, CYP4G1 mRNA had been found exclusively in oenocytes in *D. melanogaster*.

Figure 5:
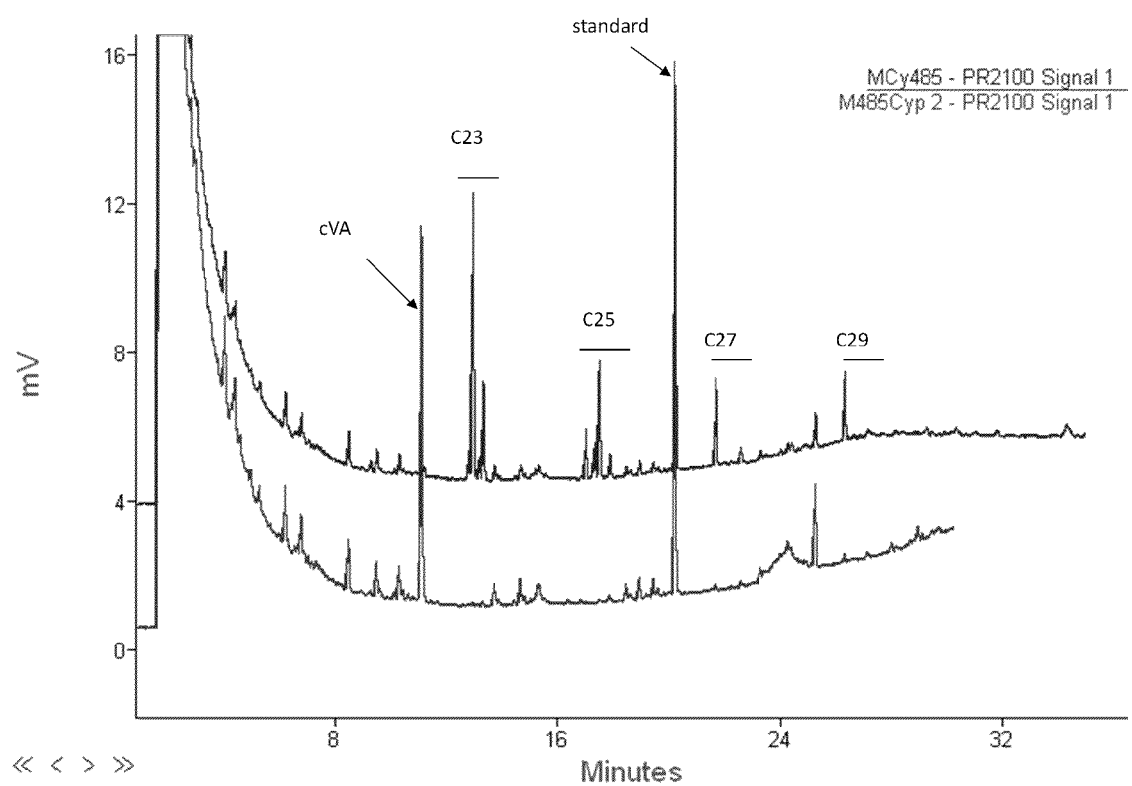
FIG. 5 is a representative gas chromatography (GC) profile of male 485 line *D. melanogaster* that have either knocked down CYP4G1 (lower line) or wildtype activity (upper line). Carbon lengths of various hydrocarbons are noted above their corresponding peaks.
Figure 6:
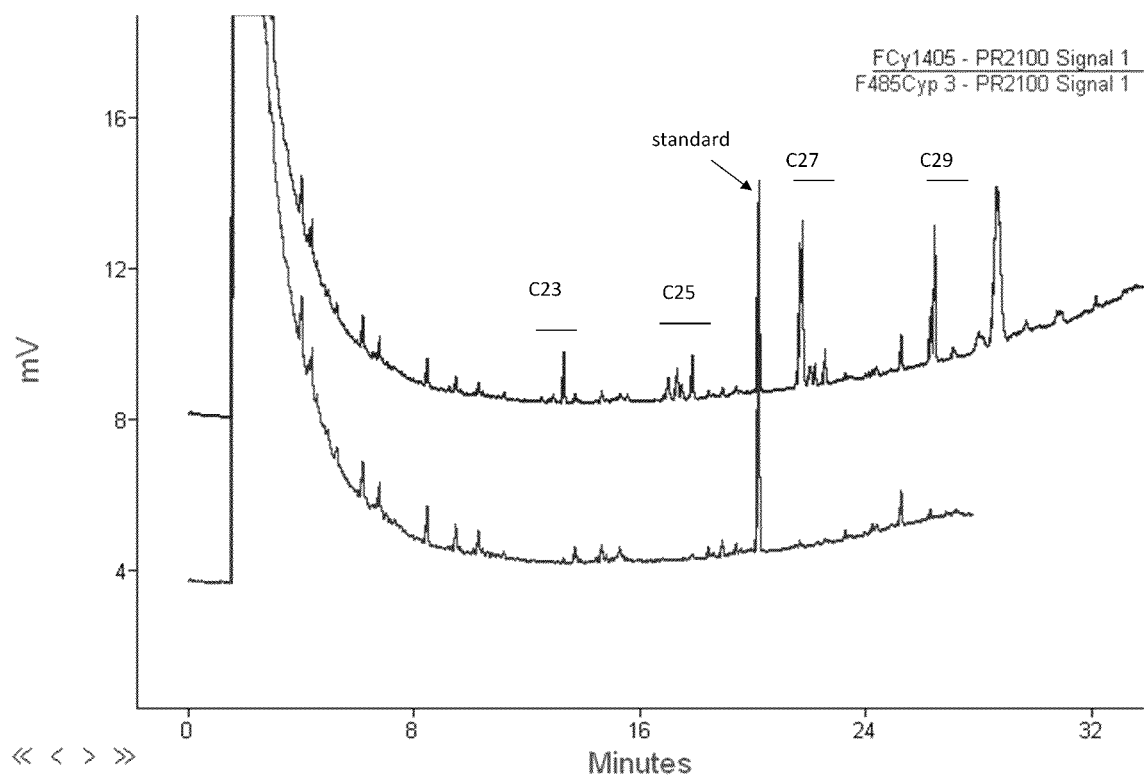
FIG. 6 is a representative GC profile of male 1405 line *D. melanogaster* that have either knocked down CYP4G1 (lower line) or wildtype activity (upper line). Carbon lengths of various hydrocarbons are noted above their corresponding peaks.
Figure 7:
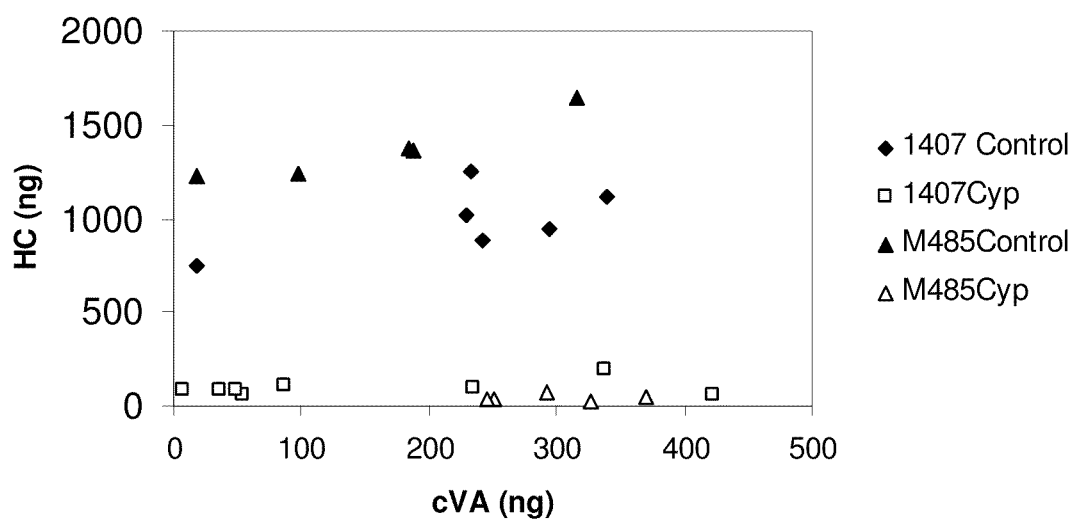
FIG. 7 is a plot of hydrocarbon content (HC) vs cis-vaccinyl acetate content for male and female 485 and 1405 line *D. melanogaster*. Control flies have normal CYP4G1 activity, while the "Cyp" samples have CYP4G1 activity removed by RNAi. Each point represents an individual fly.
Figure 11:
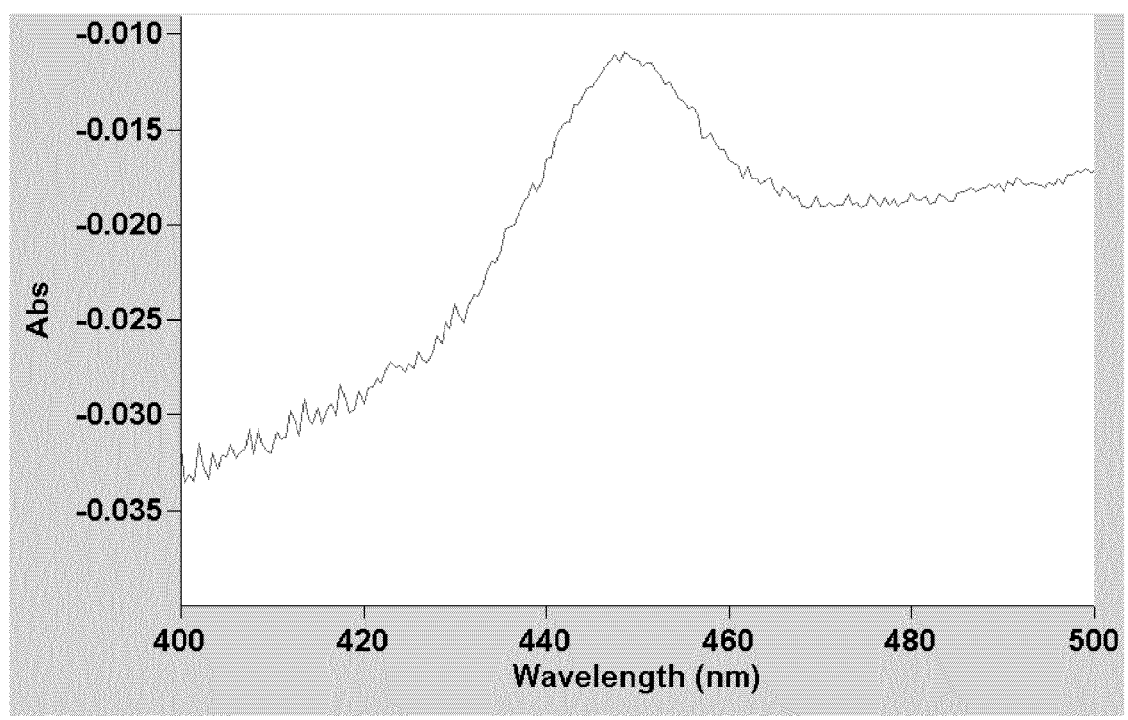
FIG. 11 is a tracing illustrating *Drosophila melanogaster* CYP4G1 expressed in yeast. The full-length CYP4G1 sequence recoded for optimal yeast codon usage was cloned into the pYeDP60 vector and expressed in a modified WR yeast strain after induction by galactose. The CO, reduced difference spectrum of yeast microsomes shows approx. 50 μmol CYP4G1/mg protein.

Fruitfly lines were generated based on an RNAi-fly stock that specifically knocks down CYP4G1 mRNA levels in oenocytes. These flies were essentially missing, or have significantly reduced, CYP4G1 activity. Hydrocarbons (HC) and cis-vaccinyl acetate (cVA) from these flies and from control (normal) flies were extracted and compared. FIG. 3 summarizes two RNAi-based lines (1405 and 485) used to knockdown CYP4G1 gene expression in *Drosophila melanogaster*. Quantitative analyses indicated the CYP4G1-knockdown flies had between 10- to 30-fold lower hydrocarbon levels than wildtype flies (FIGS. 3 and 7). Cis-vaccinyl acetate, a fatty acid-derived component specific to males, appeared at similar amounts in both strains, suggesting that fatty acid production was unaffected. Gas chromatograph traces (FIGS. 5 and 6) clearly show reduced hydrocarbon levels in the CYP4G1 knockdown flies. These studies demonstrate that CYP4G1 functions to produce hydrocarbons, i.e. it is a oxidative decarbonylase. Additionally, FIG. 11 provides a tracing illustrating *Drosophila melanogaster* CYP4G1 expressed in yeast. The full-length CYP4G1 sequence recoded for optimal yeast codon usage was cloned into the pYeDP60 vector and expressed in a modified WR yeast strain after induction by galactose. The CO-reduced difference spectrum of yeast microsomes showed approximately 50 μmol CYP4G1/mg protein. These studies are contrary to the prior studies in which *Drosophila melanogaster* CYP4G1 was predicted to be an omega hydroxylase.

Example 2

Expression and Characterization of CYP4G2

This example describes the expression and characterization of CYP4G2.

Figure 4:
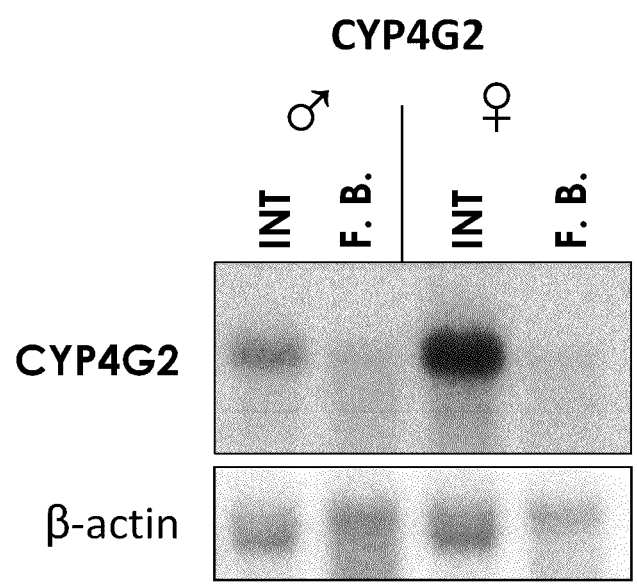
FIG. 4 is an image of a northern blot of housefly RNA isolated from male and female integuments and fat bodies hybridized with labeled CYP4G2 and actin (housekeeping control gene) cDNAs.

Housefly RNA was isolated from male and female integruments and fat bodies by methods known to those of skill in the art. Samples were subjected to northern blot analysis in which housefly RNA isolated from male and female integuments and fat bodies was hybridized with labeled CYP4G2 and actin (housekeeping control gene) cDNAs. As illustrated in FIG. 4, CYP4G2 expression was localized to the integument in both sexes, but not in the fat body. This supports that CYP4G2 mRNA is localized to oenocytes.

The results from the RNAi silencing of CYP4G1 (an ortholog of the housefly CYP4G2) provided strong evidence that both these genes encoded the cytochrome P450s that convert aldehydes to hydrocarbons in insects. To verify that they are, CYP4G2 from the housefly and CYP4G1 from the fruitfly were expressed and assayed. The CYP4G2 cDNA was amplified by PCR and directionally cloned into the BamHI and XhoI sites of pENTR4 (Invitrogen) (modified to remove the NcoI site in the poly-linker, Sandstrom et al., 2006, *Insect*

*Biochem. Molec. Biol.* 36(11):835-845) by standard methods and transformed into DH5α cells.

The BaculoDirect expression system (Invitrogen, Carlsbad, Calif.) was first used to express CYP4G2 as this system was previously used to express CYP9T2, CYP9T1, and other CYP6 and CYP9 P450s. For example, various *I. pini* and *D. ponderosae* P450 cDNAs in baculoviral vectors were expressed in Sf9 cells with (9T2, 6BW1) or without (9T1, 9Z18) housefly P450 reductase and all preparations showed the characteristic 450 nm peak. However, using this system with CYP4G2 resulted in no detectable 450 nm peak in the CO difference spectrum of recombinant microsomes. It was hypothesized that CYP4G2 may not be folding correctly in the heterologous system. The CYP4G2 membrane anchor is not well defined compared to other P450s, and has three contiguous valines close to the catalytic portion of the enzyme.

To address this problem, the second valine of the three contiguous valines in CYP4G2 (amino acid 38 of SEQ ID NO: 1) was mutated to alanine with a site-directed mutagenesis kit (Stratagene), producing CYP4G2$_{V38A}$. In addition, a chimera containing the signal sequence of CYP9T2 followed by the CYP4G2 catalytic domain (CYP9T2/4G2) was constructed (SEQ ID NO: 51 provides the nucleic acid sequence and SEQ ID NO: 52 provides the amino acid sequence of which amino acids 1-25 form 9T2). KpnI sites were created by mutagenesis (Stratagene) at the C-terminal of the signal sequence in CYP9T2, and at the N-terminal end of the CYP4G2 catalytic domain. The regions were amplified by PCR, digested with KpnI, purified, and ligated together. The ligation product was amplified by PCR using a CYP9T2-specific forward primer and a CYP4G2-specific reverse primer, directionally cloned into the SalI and XhoI sites of pENTR4, and transformed into Top 10 cells. Either or both of these strategies were hypothesized to relieve the problem of misfolding CYP4G2 in Sf9 cells.

In additional characterization studies, recombinant baculoviral CYP4G2$_{V38A}$ and CYP9T2/4G2 clones are produced by LR recombinase reaction between each pENTR4 recombinant clone and BaculoDirect Linear DNA. The recombinant baculoviral virus is transfected into Sf9 cells, and the cells are grown in the presence of ganciclovir to select for recombinant virus. The titers of viral stocks are determined by a plaque assay.

Recombinant CYP9T2/4G2 and CYP4G2$_{V38A}$ constructs are co-expressed with housefly P450 reductase for functional assays essentially as described previously (Sandstrom et al., 2006, *Insect Biochem. Molec. Biol.* 36(11):835-845; Sandstrom et al., 2008, *J. Chem. Ecol.* 34(12):1584-1592. Sf9 cells are infected with recombinant CYP9T2/4G2 or CYP4G2$_{V38A}$ baculovirus and housefly reductase baculovirus at multiplicities of infection (MOIs, pfu/cell) ranging from 0.2 to 2. A fixed, optimized MOI ratio for recombinant CYP9T2/4G2 or CYP4G2$_{V38A}$: housefly P450 reductase is used in all infections. Hemin (final concentration 0.06 mM) is added 24 hours after transfection. Sf9 are harvested 96 hours post-infection and microsomes are prepared by differential centrifugation according to Sandstrom et al. (*Insect Biochem. Molec. Biol.* 36(11):835-845, 2006). Briefly, cells are collected by centrifugation at 3000×g at 4° C. for 10 minutes and then lysed in ice cold lysis buffer (100 mM sodium phosphate pH 7.8, containing 1.1 mM EDTA, 0.1 mM DTT, 0.5 mM PMSF, 1/1000 volume of Sigma protease inhibitor cocktail, and 20% glycerol) by sonication for 30 seconds on ice using a Branson Sonifier 450. The lysate is centrifuged at 10,000×g for 20 minutes at 4° C. The supernatant is collected and centrifuged at 120,000×g for 1 hour to pellet the microsomes. The microsomes are resuspended in the same buffer and used immediately. Alternatively, because CYP4G2 activity is stable in frozen housefly microsome preparations for at least a month, recombinant Sf9 microsomes can be flash-frozen in liquid nitrogen and stored at −80° C. for later analysis. Protein concentrations are assayed by a Bradford assay, utilizing BSA as a standard. The amount of P450 expressed in Sf9 microsomes are measured by adsorption at 450 nm according to the carbon monoxide (CO)-difference spectrum analysis method.

Hydrocarbon product is extracted, isolated and assayed by standard procedures, including those disclosed herein. Alternatively, a *Drosophila* cell expression system can be used to express either CYP4G2, CYP9T2/4G2, or CYP4G2$_{V38A}$ and CYP4G1. Thus, these studies will characterize the disclosed polypeptides and assess their enzymatic activity.

Example 3

Purification of CYP9T2/4G2 or CYP4G2$_{V38A}$

This example describes methods for purifying exemplary insect P450 enzymes and in particular, their oxidative decarbonylase activity.

Compared to plants and mammals, much less is known about functions of the different insect P450 enzymes. The biochemical characteristics of insect P450 enzymes, such as CYP9T2/4G2 or CYP4G2$_{V38A}$, can be determined through assays of purified, recombinant protein. CYP9T2/4G2 or CYP4G2$_{V38A}$ is purified using an immune affinity column.

Antibody production: In order to identify a suitable antigenic region for antibody production, an alignment of CYP4G2 to CYP4G13 was compared, which revealed a 62% amino acid identity to CYP4G2. One of several loop regions identified in the model had very high identity with CYP4G2 and revealed a 15 amino acid peptide in this region with very high antigenic potential.

To generate antisera against CYP4G2, the 15 residue peptide corresponding to a predicted antigenic portion of the sequence (WQHHRKMIAPTFHQS, amino acids 157-170 of SEQ ID NO: 1) is synthesized and purified by HPLC purification by the Nevada Proteomic Center (Reno, Nev., USA). The synthesized peptide is conjugated to a keyhole limpet hemocyanin carrier via an added C-terminal cysteine, and is used to immunize rabbits at Cocalico Biologicals (Reamstown, Pa., USA). ELISA assays of collected antisera are performed to confirm immunoreactivity. The positive samples are affinity purified using a SulfoLink column (Pierce, Rockford, Ill., USA) coupled with the peptide. The immunoreactivity of the affinity-purified rabbit anti-CYP4G2 antiserum is further confirmed by western blots of bacterially-expressed recombinant CYP4G2.

In addition or alternatively, an approach relying on intact CYP4G2 as an antigen can be used. The ORF for CYP4G2 (truncated to remove the membrane anchor) is inserted into pENT4 so that the vector-encoded His tag is fused to the C-terminal. This truncated CYP4G2 ("CYP4G2$_{cat}$") is transferred to the BaculoDirect expression vector by recombination, and high-titre virus stocks is prepared as described herein. Recombinant CYP4G2$_{cat}$-His fusion protein is subsequently purified on a Ni$^{2+}$-column and incubated with enterokinase to remove the His tag. Purification of CYP4G2$_{cat}$-His is confirmed by SDS-PAGE and peptide sequencing.

Protein purification: Recombinant CYP9T2/4G2 or CYP4G2$_{V38A}$ is purified with an immune affinity column. Microsomal fractions of the cells are prepared according to methods described herein and solubilized with detergent. The solubilized enzyme is applied to a CYP4G2 affinity column prepared by fixing purified rabbit anti-CYP4G2 antibody to a protein A column (Pierce Protein Research Products, Rockford, Ill.). The column is washed to remove unbound protein and recombinant CYP4G2 is eluted with high salt buffer.

Alternatively, if this procedure reduces CYP4G2 catalytic activity, CYP4G2 is purified by standard ion exchange chromatography. The microsomal fraction is resuspended in 10 mM potassium phosphate buffer, ph 7.5, containing 20% glycerol, 0.1 mM EDA, 0.1 mM DTT and 0.1 mM BHT (Buffer A). A mixture of 1.7% (v/v) Lubrol PX and 4.25% (w/v) cholate is added to the microsomal suspension under stiffing to give a final concentration of 0.2% Lubrol PX and 0.5% cholate. The suspension is stirred gently for 40 minutes at 4° C., and then centrifuged at 105,000×g for 60 minutes. Calcium phosphate gel is added to the supernatant, and the supernatant is collected after centrifugation at 2000×g for 5 min. The precipitated gel is washed with 7 ml of 10 mM potassium phosphate buffer pH 7.5, containing 20% glycerol, 0.1 mM EDTA, 0.2% Lubro PX and 0.5% cholate. After centrifugation at 2000×g for 5 minutes, the supernatant is collected and mixed with the first supernatant to form the enzyme fraction. The supernatant is applied to a HiTrap DEAE FF column connected to an AKTApurifier (Amersham Biosciences). The column is washed with one bed-volume of buffer A and the with two bed-volume of 50 mM NaCl. Finally, the enzyme is eluted with a linear gradient of 50-200 mM NaCl. The amount of heme-containing CYP9T2/4G2 or CYP4G2$_{V38A}$ in the elution is monitored by measuring the absorption at 450 nm. The fractions containing the CYP4G2 activity is concentrated with Centriprep concentrators (Amicon, Billerica, Mass.) and the buffer is exchanged 10 mM potassium phosphate buffer, pH 7.5, containing 20% glycerol. The sample is concentrated to a small volume and applied to a hydroxyapatite column. The enzyme in the pass through fraction is collected, measured by carbon monoxide (CO)-difference spectrum analysis method and stored at −80° C. until use. Purification is confirmed by SDS-PAGE, native gel electrophoresis and isoelectric focusing. Amino acid sequencing and MALDI-MS analyses are also performed to verify the identity and integrity of the isolated proteins. The CO-reduced difference spectra are measured to observe the peak at 450 which confirms the preparation of active P450

Example 4

Characterization of CYP9T2/4G2 and CYP4G2$_{V38A}$

This example provides methods for characterizing disclosed cytochrome P450 enzymes.

Isolated P450s require lipid for activity. The approach used to mimic the structural arrangement of lipids and enzymes within the endoplasmic reticulum is to physically incorporate the cytochromes P450 in a vesicle bilayer of phospholipids. To obtain optimal activity, phospholipid is added to the assay mixture. The procedure is as follows: dilaurylphosphateidylcholine (DLPC), is suspended at a concentration of 5 mM in a solution of 50 mM potassium phosphate (pH7.25), 20% glycerol, 0.1 M NaCl, and 5 mM EDTA. The suspension lipid is sonicated in a glass tube in a water bath until it turns completely clear. Once the lipid is clear, purified CYP9T2/4G2 or CYP4G2$_{V38A}$ or other disclosed purified polypeptides and lipid is mixed in microfuge tubes. The above protein and lipid is incubated at room temperature for 2 hours. After the incubation, the mixture is aliquoted into assay tubes, and buffer and reaction components are added directly to the mixture. The assay solutions are incubated at 30° C. in the presence of substrate for 5 minutes, then reactions are started by adding NADPH. The standard experimental procedure in our lab will performed as described in objective-1. The lipid is added at varying ratios (100:1 to 500:1) to find the ideal ratio for CYP9T2/4G2 or CYP4G2$_{V38A}$ by assaying the activity. If adding lipid is difficult, protein can be added back from housefly integument tissue to see if a hydrocarbon binding protein is present that would bind hydrocarbon as it is produced and increase activity or time of linearity of reaction.

Chain length specificity: Long chain hydrocarbons of insects play central roles in the waterproofing of the insect cuticle and function extensively in chemical communication. Thus, deuterium- or tritium-labeled aldehydes of 14, 16, 18, 20, 22, 24 and 28 carbons are prepared by the method used by Reed et al. (*Proc. Natl. Acad. Sci. U.S.A.* 91(21): 10000-10004, 1994). Each aldehyde is assayed individually and the rate of conversion of aldehyde to hydrocarbon is monitored by GC-MS (deuterium labeled) or liquid scintillation counting (tritium labeled). In addition, groups of aldehydes are assayed together to determine the chain length preference.

Selectivity for the cofactor: Reed et al. (*Biochemistry* 34: 26221-26227, 1995) found when NADH replaced NADPH as a reductant, both males and females produced much less hydrocarbon. In contrast to the results using NADPH, males produced more hydrocarbon than females over the entire range of NADH concentrations tested. Purified P450 is assayed in the presence of varying amounts of NADPH, NADH or a combination of NADPH and NADH to determine the specificity of the reductant. If applicable, the Michaelis-Menton equation is used to evaluate $K_M$, $k_{cat}$, and $K_{cat}/K_M$ for the various substrates. These studies will allow the disclosed polypeptides to be characterized.

Example 5

Molecular Modeling of CYP4G2

This example provides techniques to gain insight into the structure of CYP4G2. Molecular modeling has become an increasingly useful tool in understanding the mechanisms underlying biological phenomena. Since proteins are long, linear molecules even with limited flexibility the number of possible conformations is enormous: thus construction of models based simply from first principles is impractical at this time. Historically molecular models of proteins rely on constraints generated from experimental data (e.g., X-ray diffraction of single crystals). As the Protein Data Bank has accumulated a large number of experimentally constrained models of protein structure, it became evident that proteins form a limited number of folds (perhaps 1000-2000) thus making it possible to use this knowledge of protein folds to constrain model building. The combination of knowledge and energy based methods (constraining the protein so that it is at the lowest energy conformation) has had many successful predictions of protein structure. Success depends on correctly identifying a homologous protein whose structure has been determined experimentally. This so-called template is then used to constrain model building of the unknown protein (the target). Since protein sequence determines the secondary, tertiary, and quaternary structure of protein, sequence homology is commonly used to identify template structures.

Figure 9:
FIG. 9 is a digital image of a model of *Homo sapiens* microsomal cytochrome P450 3A4 (PDB 1TQN) illustrating the variant regions.
Figure 10:
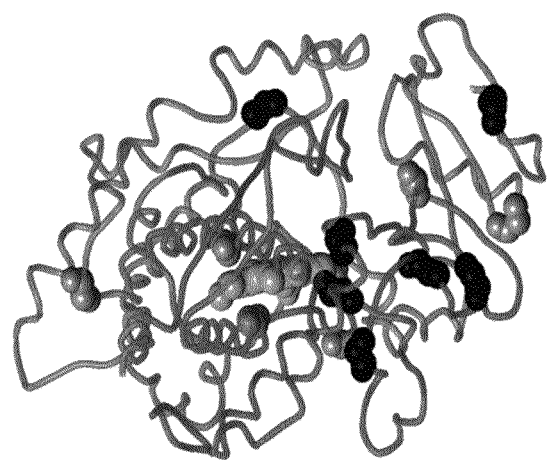
FIG. 10 is a digital image of a model of *Homo sapiens* microsomal cytochrome P450 3A4 (PDB 1TQN) exemplifying both the conserved and less conserved regions are intermixed unlike the alignment (FIG. 8) where there are distinct regions.

Cytochromes P450 are quite varied in function and have a broad substrate specificity thus making the molecular modeling of P450s challenging. A ClustalW 2.0 alignment (FIG. 8) of *Musca domestica* cytochrome CYP4G2 with other P450s from the PDB, specifically *Homo sapiens* cytochrome CYP3A4 (pdb 1TQN) and *Mycobacterium tuberculosis* CYP51 (pdb 2CIB), show an area that contains many gaps, areas of varying homology, and few invariant residues as exemplified in the model and alignment. While there are differences within this class of enzymes, there are also many similarities. One important region of similarity includes the heme binding at the active center (FIG. 9), thus placing constraints on the protein fold around the binding/active site. Invariant glycines and prolines (FIGS. 9 and 10) are of interest because these residues have unique effects on Ramachandran space and thus on backbone geometry. The tiny side chain of glycine also facilitates tertiary interactions such as alpha-helix crossings, as seen in FIG. 9. Prolines strongly stiffen the peptide chain, while glycines cause the protein to have greater flexibility, thus they are often found where turns are located as exemplified in FIG. 10. The alignment in FIG. 8 shows the characteristic invariant cysteine, which binds to the iron center of the heme in the active site forming the 6$^{th}$ ligand of the heme group (FIG. 9), as is seen with cytochromes P450. Upon further examination of this template (1TQN) a pocket where a substrate has the potential to fit was observed in an area on the opposite side of the heme from the cysteine. The model of 1TQN shows that the more conserved and the less conserved regions make up approximately equal halves of the protein, the more conserved areas being more closely associated with the heme binding center (FIG. 10). Note the two halves of the primary structure are interdigitated in the tertiary structure. Thus conserved and non-conserved regions strongly interact. CYP4G2 is longer than the other enzymes examined in the above alignment, thus the fly enzyme will contain multiple insertions. In this example, the amino acid sequence is used to predict putative solution conformations of the protein. Complementarity of the binding site to possible substrates (e.g., aldehydes 18 carbons, 24 carbons long, etc) are evaluated using molecular dynamics and visualized using programs such as MOLCAD (Heiden et al., 1993, *J. Comput. Aided Mol. Des.* 7(5): 503-14).)

The methods utilized are calibrated against solved structures of known P450 proteins with ligands bound in the binding/active site. The energy of interaction between substrate and enzyme using free energy perturbation are calculated and compared with empirical methods using the AMBER suite of computational programs (Case et al., 2005, *J. Comput. Chem.* 26(16):1668-1688). When this model is experimentally confirmed, then it is applied to predict substrate specificity. In addition, upon determination that the model is realistic, it can be used to find ways to engineer the P450 to function as needed. Models are built by a combination of sequence homology (FUGUE) (Williams et al., 2001, *Proteins* 5:92-97) and threading, which uses recognition of protein folds of known structure, rather than homology, to base a structure prediction on using programs like Matchmaker, or GeneFold. Ligands are docked (e.g., Morris et al., 1996, *J. Comput. Aided Mol. Des.* 10(4): 293-304) and energies of interaction are determined by using free energy perturbation (examining energies between two states of a protein) and integration methods (calculates free energy for consecutive points in time and is calculated from an average over all points).

Other computational tools are investigated and incorporated if they are found to be beneficial. In addition to measurement of catalytic properties (substrate specificity, product analysis, inhibition), conformational verification can be done through optical spectroscopy (such as CD, UV-vis, fluorescence perturbation, fluorescence quenching, depolarization of fluorescence), hydrodynamics (e.g., gel permeation chromatography, analytical ultracentrifugation, inelastic light scattering), chemical modification (number and rates of reaction), site-directed mutagenesis and kinetics of proteolytic digestion.

It is to be understood that the above discussion provides a detailed description of various embodiments. The above descriptions will enable those of ordinary skill in the art to make and use the disclosed embodiments, and to make departures from the particular examples described above to provide embodiments of the methods and apparatuses constructed in accordance with the present disclosure. The embodiments are illustrative, and not intended to limit the scope of the present disclosure. The scope of the present disclosure is rather to be determined by the scope of the claims as issued and equivalents thereto.

We claim:

1. An isolated polypeptide sequence having an amino acid sequence at least 99% identity to the amino acid sequence of cytochrome P450 CYP4G2 (SEQ ID NO: 1) and having cytochrome P450 monooxygenase activity.

2. The isolated polypeptide sequence of claim 1, wherein the polypeptide sequence is as set forth by SEQ ID NO: 1.

3. A method of catalyzing hydrocarbon formation comprising contacting a sample comprising a fatty aldehyde with the polypeptide of claim 1.

4. A method of catalyzing hydrocarbon formation comprising contacting a sample comprising a fatty aldehyde with the polypeptide of claim 3.

* * * * *

SEQUENCE LISTING

```
<160> NUMBER OF SEQ ID NOS: 52

<210> SEQ ID NO 1
<211> LENGTH: 559
<212> TYPE: PRT
<213> ORGANISM: Musca domestica

<400> SEQUENCE: 1

Met Thr Ala Asp Thr Leu Val Leu Glu Thr Met Asp Ser Ala Lys Asn
1               5                   10                  15

Ser Thr Ala Gly Pro Ala Thr Val Leu Asn Pro Ile Trp Thr Ala Leu
            20                  25                  30

Leu Gly Ile Ala Val Val Val Ser Leu Tyr Glu Ile Trp Leu Arg Asn
        35                  40                  45

Thr Arg Lys Tyr Lys Leu Thr Ala Asn Met Pro Asn Pro Pro Met Leu
    50                  55                  60

Pro Leu Ile Gly Asn Gly His Leu Val Ala His Leu Thr Asn Ala Glu
65                  70                  75                  80

Ile Leu Ala Arg Gly Ile Gly Tyr Met Gln Thr Tyr Gly Gly Ala Met
                85                  90                  95
```

```
Arg Gly Phe Leu Gly Pro Met Leu Val Val Phe Leu Trp Asn Ala Pro
            100                 105                 110

Asp Ile Glu Leu Ile Leu Ser Thr His Thr His Leu Glu Lys Ser Ile
            115                 120                 125

Glu Tyr Arg Phe Phe Lys Pro Trp Phe Gly Asp Gly Leu Leu Ile Ser
130                 135                 140

Asn Gly His His Trp Gln His Arg Lys Met Ile Ala Pro Thr Phe
145                 150                 155                 160

His Gln Ser Ile Leu Lys Ser Phe Val Pro Ala Phe Val Gln His Ser
                    165                 170                 175

Lys Lys Val Val Glu Arg Met Ala Lys Glu Leu Gly Lys Glu Phe Asp
            180                 185                 190

Val His Asp Tyr Met Ser Gln Thr Thr Val Glu Ile Leu Leu Ser Thr
        195                 200                 205

Ala Met Gly Val Lys Lys Val Pro Glu Asp Asn Lys Ser Leu Glu Tyr
        210                 215                 220

Ala Lys Ala Val Val Asp Met Cys Asp Ile Ile His Lys Arg Gln Leu
225                 230                 235                 240

Lys Phe Phe Tyr Arg Met Asp Ala Leu Tyr Asn Leu Ser Met Ser
                245                 250                 255

Glu Lys Gly Lys Lys Met Met Asp Ile Ile Leu Gly Met Thr Arg Lys
            260                 265                 270

Val Val Thr Glu Arg Gln Gln Asn Phe Asn Ala Glu Ser Arg Ala Ile
        275                 280                 285

Val Glu Glu Asp Asp Glu Ile Ser Lys Gln Lys Gln Gln Ala Lys Lys
        290                 295                 300

Lys Glu Gly Leu Arg Asp Asp Leu Asp Asp Ile Asp Glu Asn Asp Val
305                 310                 315                 320

Gly Ala Lys Lys Arg Leu Ala Leu Leu Asp Ala Met Met Ala Met Ser
                325                 330                 335

Lys Asn Pro Asp Val Glu Trp Thr Asp Lys Asp Val Met Asp Glu Val
            340                 345                 350

Asn Thr Ile Met Phe Glu Gly His Asp Thr Thr Ser Ala Gly Ser Ser
        355                 360                 365

Phe Val Leu Cys Met Leu Gly Ile Tyr Lys Asp Ile Gln Glu Lys Val
        370                 375                 380

Leu Ala Glu Gln Lys Ala Ile Phe Gly Asp Asn Phe Leu Arg Asp Cys
385                 390                 395                 400

Thr Phe Ala Asp Thr Met Glu Met Lys Tyr Leu Glu Arg Val Ile Met
                405                 410                 415

Glu Thr Leu Arg Leu Tyr Pro Pro Val Pro Leu Ile Ala Arg Arg Ala
            420                 425                 430

Glu Phe Asp Val Lys Leu Ala Ser Gly Pro Tyr Thr Ile Pro Lys Gly
        435                 440                 445

Thr Thr Val Val Ile Ala Gln Phe Ala Val His Arg Asn Pro Gln Tyr
        450                 455                 460

Phe Pro Asn Pro Glu Lys Phe Asp Pro Asp Asn Phe Leu Pro Glu Arg
465                 470                 475                 480

Met Ala Asn Arg His Tyr Tyr Ser Phe Ile Pro Phe Ser Ala Gly Pro
                485                 490                 495

Arg Ser Cys Val Gly Arg Lys Tyr Ala Met Leu Lys Leu Lys Val Leu
            500                 505                 510

Leu Ser Thr Ile Ile Arg Asn Tyr Ser Val Gln Ser Asn Gln Gln Glu
```

```
                     515                 520                 525

Lys Asp Phe Lys Leu Gln Ala Asp Ile Ile Leu Lys Ile Glu Asn Gly
            530                 535                 540

Phe Asn Ile Met Leu Asn Arg Arg Pro Glu Ala Met Lys Ala Met
545                 550                 555

<210> SEQ ID NO 2
<211> LENGTH: 486
<212> TYPE: PRT
<213> ORGANISM: Musca domestica

<400> SEQUENCE: 2

Val Ala Ala Gly Leu Ser Asn Ala Glu Ile Leu Ala Val Gly Leu Gly
1               5                   10                  15

Tyr Leu Asn Lys Tyr Gly Glu Thr Met Lys Ala Trp Leu Gly Asn Val
            20                  25                  30

Leu Leu Val Phe Leu Thr Asn Pro Ser Asp Ile Glu Leu Ile Leu Ser
        35                  40                  45

Gly His Gln His Leu Thr Lys Ala Glu Glu Tyr Arg Tyr Phe Lys Pro
    50                  55                  60

Trp Phe Gly Asp Gly Leu Ile Ser Asn Gly His His Trp Arg His
65                  70                  75                  80

His Arg Lys Met Ile Ala Pro Thr Phe His Gln Ser Ile Leu Lys Ser
                85                  90                  95

Phe Val Pro Thr Phe Val Asp His Ser Lys Ala Val Val Ala Arg Met
            100                 105                 110

Gly Leu Glu Ala Gly Lys Ser Phe Asp Val His Asp Tyr Met Ser Gln
        115                 120                 125

Thr Thr Val Asp Ile Leu Leu Ser Thr Ala Met Gly Val Lys Lys Leu
    130                 135                 140

Pro Glu Gly Asn Lys Ser Phe Glu Tyr Ala Gln Ala Val Val Asp Met
145                 150                 155                 160

Cys Asp Ile Ile His Lys Arg Gln Val Lys Leu Leu Tyr Arg Leu Asp
                165                 170                 175

Ser Ile Tyr Lys Phe Thr Lys Leu Arg Glu Lys Gly Asp Arg Met Met
            180                 185                 190

Asn Ile Ile Leu Gly Met Thr Ser Lys Val Val Lys Asp Arg Lys Glu
        195                 200                 205

Asn Phe Gln Glu Glu Ser Arg Ala Ile Val Glu Glu Ile Ser Thr Pro
    210                 215                 220

Val Ala Ser Thr Pro Ala Ser Lys Lys Glu Gly Leu Arg Asp Asp Leu
225                 230                 235                 240

Asp Asp Ile Asp Glu Asn Asp Val Gly Ala Lys Arg Arg Leu Ala Leu
                245                 250                 255

Leu Asp Ala Met Val Glu Met Ala Lys Asn Pro Asp Ile Glu Trp Asn
            260                 265                 270

Glu Lys Asp Ile Met Asp Glu Val Asn Thr Ile Met Phe Glu Gly His
        275                 280                 285

Asp Thr Thr Ser Ala Gly Ser Ser Phe Ala Leu Cys Met Met Gly Ile
    290                 295                 300

His Lys Asp Ile Gln Ala Lys Val Phe Ala Glu Gln Lys Ala Ile Phe
305                 310                 315                 320

Gly Asp Asn Met Leu Arg Asp Cys Thr Phe Ala Asp Thr Met Glu Met
                325                 330                 335

Lys Tyr Leu Glu Arg Val Ile Leu Glu Thr Leu Arg Leu Tyr Pro Pro
```

```
                    340             345             350
Val Pro Leu Ile Ala Arg Arg Leu Asp Tyr Asp Leu Lys Leu Ala Ser
                355                 360                 365

Gly Pro Tyr Thr Val Pro Lys Gly Thr Thr Val Ile Val Leu Gln Tyr
        370                 375                 380

Cys Val His Arg Arg Pro Asp Ile Tyr Pro Asn Pro Thr Lys Phe Asp
385                 390                 395                 400

Pro Asp Asn Phe Leu Pro Glu Arg Met Ala Asn Arg His Tyr Tyr Ser
                405                 410                 415

Phe Ile Pro Phe Ser Ala Gly Pro Arg Ser Cys Val Gly Arg Lys Tyr
                420                 425                 430

Ala Met Leu Lys Leu Lys Val Leu Leu Ser Thr Ile Val Arg Asn Tyr
                435                 440                 445

Ile Val His Ser Thr Asp Thr Glu Ala Asp Phe Lys Leu Gln Ala Asp
                450                 455                 460

Ile Ile Leu Lys Leu Glu Asn Gly Phe Asn Val Ser Leu Glu Lys Arg
465                 470                 475                 480

Gln Tyr Ala Thr Val Ala
                485

<210> SEQ ID NO 3
<211> LENGTH: 556
<212> TYPE: PRT
<213> ORGANISM: Drosophila erecta

<400> SEQUENCE: 3

Met Ala Val Glu Val Val Gln Glu Thr Leu Gln Gln Ala Ala Ala Ser
1               5                   10                  15

Ser Ser Thr Thr Val Leu Gly Phe Ser Pro Met Phe Thr Thr Leu Val
                20                  25                  30

Gly Thr Leu Val Ala Met Ala Leu Tyr Glu Tyr Trp Arg Arg Asn Ser
            35                  40                  45

Arg Glu Tyr Arg Met Val Ala Asn Ile Pro Ser Pro Pro Glu Leu Pro
        50                  55                  60

Ile Leu Gly Gln Ala His Val Ala Ala Gly Leu Ser Asn Ala Glu Ile
65                  70                  75                  80

Leu Ala Val Gly Leu Gly Tyr Leu Asn Lys Tyr Gly Glu Thr Met Lys
                85                  90                  95

Ala Trp Leu Gly Asn Val Leu Leu Val Phe Leu Thr Asn Pro Ser Asp
            100                 105                 110

Ile Glu Leu Ile Leu Ser Gly His Gln His Leu Thr Lys Ala Glu Glu
        115                 120                 125

Tyr Arg Tyr Phe Lys Pro Trp Phe Gly Asp Gly Leu Leu Ile Ser Asn
    130                 135                 140

Gly His His Trp Arg His His Arg Lys Met Ile Ala Pro Thr Phe His
145                 150                 155                 160

Gln Ser Ile Leu Lys Ser Phe Val Pro Thr Phe Val Asp His Ser Lys
                165                 170                 175

Ala Val Val Ala Arg Met Gly Leu Glu Ala Gly Lys Ser Phe Asp Val
            180                 185                 190

His Asp Tyr Met Ser Gln Thr Thr Val Asp Ile Leu Leu Ser Thr Ala
        195                 200                 205

Met Gly Val Lys Lys Leu Pro Glu Gly Asn Lys Ser Phe Glu Tyr Ala
    210                 215                 220

Gln Ala Val Val Asp Met Cys Asp Ile Ile His Lys Arg Gln Val Lys
```

```
           225                 230                 235                 240
Leu Leu Tyr Arg Leu Asp Ser Ile Tyr Lys Phe Thr Lys Leu Arg Glu
                245                 250                 255
Lys Gly Asp Arg Met Met Asn Ile Ile Leu Gly Met Thr Ser Lys Val
            260                 265                 270
Val Lys Asp Arg Lys Glu Asn Phe Gln Glu Glu Ser Arg Ala Ile Val
        275                 280                 285
Glu Glu Ile Ser Thr Pro Ala Ser Thr Pro Ala Ser Lys Lys Glu
    290                 295                 300
Gly Leu Arg Asp Asp Leu Asp Asp Ile Asp Glu Asn Asp Val Gly Ala
305                 310                 315                 320
Lys Arg Arg Leu Ala Leu Leu Asp Ala Met Val Glu Met Ala Lys Asn
                325                 330                 335
Pro Asp Ile Glu Trp Asn Glu Lys Asp Ile Met Asp Glu Val Asn Thr
            340                 345                 350
Ile Met Phe Glu Gly His Asp Thr Thr Ser Ala Gly Ser Ser Phe Ala
        355                 360                 365
Leu Cys Met Met Gly Ile His Lys Asp Ile Gln Ala Lys Val Phe Ala
    370                 375                 380
Glu Gln Lys Ala Ile Phe Gly Asp Asn Met Leu Arg Asp Cys Thr Phe
385                 390                 395                 400
Ala Asp Thr Met Glu Met Lys Tyr Leu Glu Arg Val Ile Leu Glu Thr
                405                 410                 415
Leu Arg Leu Tyr Pro Pro Val Pro Leu Ile Ala Arg Leu Asp Tyr
            420                 425                 430
Asp Leu Lys Leu Ala Ser Gly Pro Tyr Thr Val Pro Lys Gly Thr Thr
        435                 440                 445
Val Ile Val Leu Gln Tyr Cys Val His Arg Pro Asp Ile Tyr Pro
    450                 455                 460
Asn Pro Thr Lys Phe Asp Pro Asp Asn Phe Leu Pro Glu Arg Met Ala
465                 470                 475                 480
Asn Arg His Tyr Tyr Ser Phe Ile Pro Phe Ser Ala Gly Pro Arg Ser
                485                 490                 495
Cys Val Gly Arg Lys Tyr Ala Met Leu Lys Leu Lys Val Leu Leu Ser
            500                 505                 510
Thr Ile Val Arg Asn Tyr Ile Val His Ser Thr Asp Thr Glu Ala Asp
        515                 520                 525
Phe Lys Leu Gln Ala Asp Ile Ile Leu Lys Leu Glu Asn Gly Phe Asn
    530                 535                 540
Val Ser Leu Glu Lys Arg Gln Tyr Ala Thr Val Ala
545                 550                 555

<210> SEQ ID NO 4
<211> LENGTH: 556
<212> TYPE: PRT
<213> ORGANISM: Drosophila simulans

<400> SEQUENCE: 4

Met Ala Val Glu Val Val Gln Glu Thr Leu Gln Gln Ala Ala Ala Ser
1               5                   10                  15
Ser Ser Thr Thr Val Leu Gly Phe Ser Pro Met Leu Thr Thr Leu Val
            20                  25                  30
Gly Thr Leu Val Ala Met Ala Leu Tyr Glu Tyr Trp Arg Arg Asn Ser
        35                  40                  45
Arg Glu Tyr Arg Met Val Ala Asn Ile Pro Ser Pro Pro Glu Leu Pro
```

```
            50                  55                  60
Ile Leu Gly Gln Ala His Val Ala Ala Gly Leu Ser Asn Ala Glu Ile
 65                  70                  75                  80

Leu Ala Val Gly Leu Gly Tyr Leu Asn Lys Tyr Gly Glu Thr Met Lys
                 85                  90                  95

Ala Trp Leu Gly Asn Val Leu Leu Val Phe Leu Thr Asn Pro Ser Asp
                100                 105                 110

Ile Glu Leu Ile Leu Ser Gly His Gln His Leu Thr Lys Ala Glu Glu
                115                 120                 125

Tyr Arg Tyr Phe Lys Pro Trp Phe Gly Asp Gly Leu Leu Ile Ser Asn
130                 135                 140

Gly His His Trp Arg His His Arg Lys Met Ile Ala Pro Thr Phe His
145                 150                 155                 160

Gln Ser Ile Leu Lys Ser Phe Val Pro Thr Phe Val Asp His Ser Lys
                165                 170                 175

Ala Val Val Ala Arg Met Gly Leu Glu Ala Gly Lys Ser Phe Asp Val
                180                 185                 190

His Asp Tyr Met Ser Gln Thr Thr Val Asp Ile Leu Leu Ser Thr Ala
                195                 200                 205

Met Gly Val Lys Lys Leu Pro Glu Gly Asn Lys Ser Phe Glu Tyr Ala
210                 215                 220

Gln Ala Val Val Asp Met Cys Asp Ile Ile His Lys Arg Gln Val Lys
225                 230                 235                 240

Leu Leu Tyr Arg Leu Asp Ser Ile Tyr Lys Phe Thr Lys Leu Arg Glu
                245                 250                 255

Lys Gly Asp Arg Met Met Asn Ile Ile Leu Gly Met Thr Ser Lys Val
                260                 265                 270

Val Lys Asp Arg Lys Glu Asn Phe Gln Glu Glu Ser Arg Ala Ile Val
                275                 280                 285

Glu Glu Ile Ser Thr Pro Val Ala Ser Thr Pro Ala Ser Lys Lys Glu
                290                 295                 300

Gly Leu Arg Asp Asp Leu Asp Asp Ile Asp Glu Asn Asp Val Gly Ala
305                 310                 315                 320

Lys Arg Arg Leu Ala Leu Leu Asp Ala Met Val Glu Met Ala Lys Asn
                325                 330                 335

Pro Asp Ile Glu Trp Asn Glu Lys Asp Ile Met Asp Glu Val Asn Thr
                340                 345                 350

Ile Met Phe Glu Gly His Asp Thr Thr Ser Ala Gly Ser Ser Phe Ala
                355                 360                 365

Leu Cys Met Met Gly Ile His Lys Asp Ile Gln Ala Lys Val Phe Ala
370                 375                 380

Glu Gln Lys Ala Ile Phe Gly Asp Asn Met Leu Arg Asp Cys Thr Phe
385                 390                 395                 400

Ala Asp Thr Met Glu Met Lys Tyr Leu Glu Arg Val Ile Leu Glu Thr
                405                 410                 415

Leu Arg Leu Tyr Pro Pro Val Pro Leu Ile Ala Arg Arg Leu Asp Tyr
                420                 425                 430

Asp Leu Lys Leu Ala Ser Gly Pro Tyr Thr Val Pro Lys Gly Thr Thr
                435                 440                 445

Val Ile Val Leu Gln Tyr Cys Val His Arg Arg Pro Asp Ile Tyr Pro
450                 455                 460

Asn Pro Thr Lys Phe Asp Pro Asp Asn Phe Leu Pro Glu Arg Met Ala
465                 470                 475                 480
```

```
Asn Arg His Tyr Tyr Ser Phe Ile Pro Phe Ser Ala Gly Pro Arg Ser
            485                 490                 495

Cys Val Gly Arg Lys Tyr Ala Met Leu Lys Leu Lys Val Leu Leu Ser
            500                 505                 510

Thr Ile Val Arg Asn Tyr Ile Val His Ser Thr Asp Thr Glu Ala Asp
            515                 520                 525

Phe Lys Leu Gln Ala Asp Ile Ile Leu Lys Leu Glu Asn Gly Phe Asn
            530                 535                 540

Val Ser Leu Glu Lys Arg Gln Tyr Ala Thr Val Ala
545                 550                 555

<210> SEQ ID NO 5
<211> LENGTH: 556
<212> TYPE: PRT
<213> ORGANISM: Drosophila yakuba

<400> SEQUENCE: 5

Met Ala Val Glu Val Val Gln Glu Thr Leu Gln Gln Ala Ala Ala Ser
1               5                   10                  15

Ser Ser Thr Thr Val Leu Gly Phe Ser Pro Met Phe Thr Thr Leu Val
            20                  25                  30

Gly Thr Leu Val Ala Met Ala Leu Tyr Glu Tyr Trp Arg Arg Asn Ser
            35                  40                  45

Arg Glu Tyr Arg Met Val Ala Asn Ile Pro Ser Pro Pro Glu Leu Pro
50                  55                  60

Ile Leu Gly Gln Ala His Val Ala Ala Gly Leu Ser Asn Ala Glu Ile
65                  70                  75                  80

Leu Ala Val Gly Leu Gly Tyr Leu Asn Lys Tyr Gly Glu Thr Met Lys
            85                  90                  95

Ala Trp Leu Gly Asn Val Leu Leu Val Phe Leu Thr Asn Pro Ser Asp
            100                 105                 110

Ile Glu Leu Ile Leu Ser Gly His Gln His Leu Thr Lys Ala Glu Glu
            115                 120                 125

Tyr Arg Tyr Phe Lys Pro Trp Phe Gly Asp Gly Leu Leu Ile Ser Asn
130                 135                 140

Gly His His Trp Arg His His Arg Lys Met Ile Ala Pro Thr Phe His
145                 150                 155                 160

Gln Ser Ile Leu Lys Ser Phe Val Pro Thr Phe Val Asp His Ser Lys
            165                 170                 175

Ala Val Val Ala Arg Met Gly Leu Glu Ser Gly Lys Ser Phe Asp Val
            180                 185                 190

His Asp Tyr Met Ser Gln Thr Thr Val Asp Ile Leu Leu Ser Thr Ala
            195                 200                 205

Met Gly Val Lys Lys Leu Pro Glu Gly Asn Lys Ser Phe Glu Tyr Ala
210                 215                 220

Gln Ala Val Val Asp Met Cys Asp Ile Ile His Lys Arg Gln Val Lys
225                 230                 235                 240

Leu Leu Tyr Arg Leu Asp Ser Ile Tyr Lys Phe Thr Lys Leu Arg Glu
            245                 250                 255

Lys Gly Asp Arg Met Met Asn Ile Ile Leu Gly Met Thr Ser Lys Val
            260                 265                 270

Val Lys Asp Arg Lys Glu Asn Phe Gln Glu Glu Ser Arg Ala Ile Val
            275                 280                 285

Glu Glu Ile Ala Thr Pro Val Ala Ser Thr Pro Ala Ser Lys Lys Glu
290                 295                 300
```

```
Gly Leu Arg Asp Asp Leu Asp Ile Asp Glu Asn Asp Val Gly Ala
305                 310                 315                 320

Lys Arg Arg Leu Ala Leu Leu Asp Ala Met Val Glu Met Ala Lys Asn
            325                 330                 335

Pro Asp Ile Glu Trp Asn Glu Lys Asp Ile Met Asp Glu Val Asn Thr
        340                 345                 350

Ile Met Phe Glu Gly His Asp Thr Thr Ser Ala Gly Ser Ser Phe Ala
    355                 360                 365

Leu Cys Met Met Gly Ile His Lys Asp Ile Gln Ala Lys Val Phe Ala
370                 375                 380

Glu Gln Lys Ala Ile Phe Gly Asp Asn Met Leu Arg Asp Cys Thr Phe
385                 390                 395                 400

Ala Asp Thr Met Glu Met Lys Tyr Leu Glu Arg Val Ile Leu Glu Thr
                405                 410                 415

Leu Arg Leu Tyr Pro Pro Val Pro Leu Ile Ala Arg Leu Asp Tyr
            420                 425                 430

Asp Leu Lys Leu Ala Ser Gly Pro Tyr Thr Val Pro Lys Gly Thr Thr
        435                 440                 445

Val Ile Val Leu Gln Tyr Cys Val His Arg Arg Pro Asp Ile Tyr Pro
    450                 455                 460

Asn Pro Thr Lys Phe Asp Pro Asp Asn Phe Leu Pro Glu Arg Met Ala
465                 470                 475                 480

Asn Arg His Tyr Tyr Ser Phe Ile Pro Phe Ser Ala Gly Pro Arg Ser
                485                 490                 495

Cys Val Gly Arg Lys Tyr Ala Met Leu Lys Leu Lys Val Leu Leu Ser
            500                 505                 510

Thr Ile Val Arg Asn Tyr Ile Val His Ser Thr Asp Thr Glu Ala Asp
        515                 520                 525

Phe Lys Leu Gln Ala Asp Ile Ile Leu Lys Leu Glu Asn Gly Phe Asn
    530                 535                 540

Val Ser Leu Glu Lys Arg Gln Tyr Ala Thr Val Ala
545                 550                 555
```

<210> SEQ ID NO 6
<211> LENGTH: 552
<212> TYPE: PRT
<213> ORGANISM: Drosophila pseudoobscura

<400> SEQUENCE: 6

```
Met Thr Val Asp Thr Val Gln Glu Thr Leu Gln His Ala Ala Thr Ser
1               5                   10                  15

Thr Ser Gly Leu Gly Phe Ser Pro Met Leu Thr Thr Leu Val Gly Thr
            20                  25                  30

Ile Val Ala Leu Gly Leu Tyr Glu Tyr Trp Arg Arg Asn Thr Arg Glu
        35                  40                  45

Tyr Arg Met Val Ala Asn Ile Pro Ser Pro Pro Gly Leu Pro Leu Leu
    50                  55                  60

Gly Gln Ala His Met Val Ala Gly Leu Ser Asn Ala Glu Ile Leu Asn
65                  70                  75                  80

Val Gly Leu Gly Tyr Leu Asn Lys Tyr Gly Glu Thr Met Lys Ala Trp
                85                  90                  95

Leu Gly Asn Val Leu Val Phe Leu Thr Asn Pro Asn Asp Ile Glu
            100                 105                 110

Leu Ile Leu Ser Gly His Gln His Leu Thr Lys Ala Glu Glu Tyr Arg
        115                 120                 125
```

```
Tyr Phe Lys Pro Trp Phe Gly Asp Gly Leu Leu Ile Ser Asn Gly His
130                 135                 140

His Trp Arg His His Arg Lys Met Ile Ala Pro Thr Phe His Gln Ser
145                 150                 155                 160

Ile Leu Lys Ser Phe Val Pro Thr Phe Val Asp His Ser Lys Ser Val
                165                 170                 175

Val Gly Arg Met Gly Leu Glu Thr Gly Lys Ser Phe Asp Val His Asp
                180                 185                 190

Tyr Met Ser Thr Thr Thr Val Asp Ile Leu Leu Ser Thr Ala Met Gly
            195                 200                 205

Val Lys Lys Leu Pro Glu Gly Asn Lys Ser Phe Glu Tyr Ala Gln Ala
210                 215                 220

Val Val Asp Met Cys Asp Ile Ile His Lys Arg Gln Val Lys Leu Leu
225                 230                 235                 240

Tyr Arg Leu Asp Ser Ile Tyr Lys Phe Thr Lys Leu Arg Glu Lys Gly
                245                 250                 255

Asp Arg Met Met Asn Ile Ile Leu Gly Met Thr Ser Lys Val Val Lys
                260                 265                 270

Asp Arg Lys Gln Asn Phe Gln Glu Gly Ser Arg Ala Ile Val Asp Glu
                275                 280                 285

Val Gln Ala Val Ser Thr Pro Ala Thr Lys Lys Glu Gly Leu Arg Asp
290                 295                 300

Asp Leu Asp Asp Ile Asp Glu Asn Asp Val Gly Ala Lys Arg Arg Leu
305                 310                 315                 320

Ala Leu Leu Asp Ala Met Val Glu Met Ala Lys Asn Pro Asp Ile Glu
                325                 330                 335

Trp Asn Glu Lys Asp Ile Ile Asp Glu Val Asn Thr Ile Met Phe Glu
                340                 345                 350

Gly His Asp Thr Thr Ser Ala Gly Ser Ser Phe Ala Leu Cys Met Met
                355                 360                 365

Gly Ile His Lys Asp Ile Gln Glu Lys Val Phe Ala Glu Gln Lys Ala
                370                 375                 380

Ile Phe Gly Asp Asn Met Leu Arg Asp Cys Thr Phe Ala Asp Thr Asn
385                 390                 395                 400

Glu Met Lys Tyr Leu Glu Arg Val Ile Leu Glu Thr Leu Arg Leu Tyr
                405                 410                 415

Pro Pro Val Pro Leu Ile Ala Arg Arg Leu Asp Tyr Asp Leu Lys Leu
                420                 425                 430

Ala Ser Gly Pro Tyr Thr Val Pro Lys Gly Thr Thr Val Ile Val Leu
                435                 440                 445

Gln Tyr Cys Val His Arg Arg Ala Asp Ile Tyr Pro Asn Pro Thr Lys
450                 455                 460

Phe Asp Pro Asp Asn Phe Leu Pro Glu Arg Met Ala Asn Arg His Tyr
465                 470                 475                 480

Tyr Ser Phe Ile Pro Phe Ser Ala Gly Pro Arg Ser Cys Val Gly Arg
                485                 490                 495

Lys Tyr Ala Met Leu Lys Leu Lys Val Leu Leu Ser Thr Ile Val Arg
                500                 505                 510

Asn Tyr Ile Val His Ser Thr Asp Thr Glu Ala Asp Phe Lys Leu Gln
                515                 520                 525

Ala Asp Ile Ile Leu Lys Leu Glu Asn Gly Phe Asn Ile Ser Leu Glu
530                 535                 540

Lys Arg Lys Tyr Ala Thr Val Ala
545                 550
```

<210> SEQ ID NO 7
<211> LENGTH: 552
<212> TYPE: PRT
<213> ORGANISM: Drosophila mojavensis

<400> SEQUENCE: 7

Met Ser Val Glu Thr Val Gln Glu Thr Leu Gln Gln Ala Ala Lys Ser
1               5                   10                  15

Ser Gly Gly Phe Ser Pro Ile Leu Thr Gly Leu Leu Gly Thr Ile Ile
            20                  25                  30

Val Met Ala Leu Tyr Glu Tyr Trp His Arg Asn Thr Arg Glu Tyr Arg
        35                  40                  45

Met Val Ala Asn Ile Pro Ser Pro Pro Ser Leu Pro Leu Ile Gly Met
    50                  55                  60

Ala His Leu Ala Ala Gly Leu Ser Asn Ala Glu Ile Leu Ser Val Gly
65                  70                  75                  80

Leu Gly Tyr Leu Asn Lys Tyr Gly Glu Thr Met Lys Gly Trp Leu Gly
                85                  90                  95

Asn Val Leu Leu Val Phe Leu Thr Asn Pro Asn Asp Ile Glu Leu Ile
            100                 105                 110

Leu Ser Gly His Gln His Leu Thr Lys Ala Glu Glu Tyr Arg Tyr Phe
        115                 120                 125

Lys Pro Trp Phe Gly Asp Gly Leu Leu Ile Ser Asn Gly His His Trp
    130                 135                 140

Arg His His Arg Lys Met Ile Ala Pro Thr Phe His Gln Ser Ile Leu
145                 150                 155                 160

Lys Ser Phe Val Pro Thr Phe Val Ala His Ser Lys Ala Val Ser Ala
                165                 170                 175

Arg Met Ala Lys Glu Ala Gly Lys Ser Phe Asp Val His Asp Tyr Met
            180                 185                 190

Ser Gln Thr Thr Val Asp Ile Leu Leu Thr Thr Ala Met Gly Val Lys
        195                 200                 205

Lys Leu Pro Glu Gly Asn Lys Ser Phe Glu Tyr Ala Gln Ala Val Val
    210                 215                 220

Asp Met Cys Asp Ile Ile His Thr Arg Gln Val Lys Leu Leu Tyr Arg
225                 230                 235                 240

Leu Asp Ser Ile Tyr Lys Phe Thr Lys Leu Arg Glu Lys Gly Asp Arg
                245                 250                 255

Met Met Asn Ile Ile Leu Gly Met Thr Arg Lys Val Val Lys Asp Arg
            260                 265                 270

Asn Glu Asn Tyr Ser Pro Glu Ser Arg Ala Ile Ile Glu Asp Val Ala
        275                 280                 285

Glu Pro Thr Pro Ala Lys Gln Ala Thr Lys Thr Glu Gly Leu Arg Asp
    290                 295                 300

Asp Leu Asp Asp Ile Asp Glu Asn Asp Val Gly Ala Lys Arg Arg Leu
305                 310                 315                 320

Ala Leu Leu Asp Ala Met Val Glu Met Ala Lys Asn Pro Asp Ile Glu
                325                 330                 335

Trp Asn Glu Lys Asp Ile Met Asp Glu Val Asn Thr Ile Met Phe Glu
            340                 345                 350

Gly His Asp Thr Thr Ser Ala Gly Ser Ser Phe Ala Leu Cys Met Met
        355                 360                 365

Gly Ile His Lys Asp Val Gln Glu Arg Val Phe Ala Glu Gln Lys Ala
    370                 375                 380

```
Ile Phe Gly Asp Asn Met Leu Arg Asp Cys Thr Phe Ala Asp Thr Met
385                 390                 395                 400

Glu Met Lys Tyr Leu Glu Arg Val Ile Leu Glu Thr Leu Arg Met Tyr
                405                 410                 415

Pro Pro Val Pro Leu Ile Ala Arg Arg Leu Asp His Asp Val Lys Leu
            420                 425                 430

Ala Ser Gly Pro Tyr Thr Val Pro Lys Gly Thr Thr Cys Val Val Leu
        435                 440                 445

Gln Tyr Cys Val His Arg Arg Pro Asp Ile Tyr Glu Asn Pro Thr Lys
    450                 455                 460

Phe Asp Pro Asp Asn Phe Leu Pro Glu Arg Ala Ala Lys Arg His Tyr
465                 470                 475                 480

Tyr Ser Phe Ile Pro Phe Ser Ala Gly Pro Arg Ser Cys Val Gly Arg
                485                 490                 495

Lys Tyr Ala Met Leu Lys Leu Lys Val Leu Leu Ser Thr Ile Val Arg
                500                 505                 510

Asn Phe Ile Ile His Ser Thr Asp Thr Glu Ala Asp Phe Lys Leu Gln
                515                 520                 525

Ala Asp Ile Ile Leu Lys Leu Glu Asn Gly Phe Asn Ile Ser Leu Glu
530                 535                 540

Pro Arg Gln Tyr Pro Thr Ala Ala
545                 550

<210> SEQ ID NO 8
<211> LENGTH: 558
<212> TYPE: PRT
<213> ORGANISM: Drosophila virilis

<400> SEQUENCE: 8

Met Ser Val Glu Thr Val Gln Glu Thr Leu Gln Gln Ala Thr Gly Ser
1               5                   10                  15

Thr Gly Ser Phe Met Leu Ser Pro Leu Leu Thr Gly Leu Val Gly Thr
                20                  25                  30

Met Leu Ile Met Ala Leu Tyr Glu Tyr Trp His Arg Asn Thr Arg Glu
            35                  40                  45

Tyr Arg Met Val Ala Asn Ile Pro Ser Pro Ser Leu Pro Ile Ile
    50                  55                  60

Gly Met Ala His Leu Ala Ala Gly Leu Ser Asn Ala Glu Ile Leu Ala
65                  70                  75                  80

Val Gly Leu Gly Tyr Leu Asn Lys Tyr Gly Glu Thr Met Lys Ala Trp
                85                  90                  95

Leu Gly Asn Val Leu Ile Val Phe Leu Thr Asn Pro Ser Asp Ile Glu
            100                 105                 110

Leu Ile Leu Ser Gly His Gln His Leu Thr Lys Ala Glu Glu Tyr Arg
        115                 120                 125

Tyr Phe Lys Pro Trp Phe Gly Asp Gly Leu Leu Ile Ser Asn Gly His
    130                 135                 140

His Trp Arg His His Arg Lys Met Ile Ala Pro Thr Phe His Gln Ser
145                 150                 155                 160

Ile Leu Lys Ser Phe Val Pro Thr Phe Val Asp His Ser Lys Ala Val
                165                 170                 175

Ser Ala Arg Met Ala Lys Glu Ala Gly Lys Ser Phe Asp Val His Asp
            180                 185                 190

Tyr Met Ser Gln Thr Thr Val Asp Ile Leu Leu Ser Thr Ala Met Gly
        195                 200                 205
```

Val Lys Lys Leu Pro Glu Gly Asn Lys Ser Phe Glu Tyr Ala Gln Ala
    210                 215                 220

Val Val Asp Met Cys Asp Ile Ile His Lys Arg Gln Val Lys Leu Leu
225                 230                 235                 240

Tyr Arg Leu Asp Ser Ile Tyr Lys Phe Thr Lys Leu Arg Glu Lys Gly
                245                 250                 255

Asp Arg Met Met Asn Ile Ile Leu Gly Met Thr Arg Lys Val Val Lys
            260                 265                 270

Asp Arg Lys Asp Asn Phe Gln Asn Glu Thr His Ala Ile Ile Glu Glu
        275                 280                 285

Val Glu Glu Thr Pro Val Lys Gln Ser Arg Val Thr Ser Ala Thr Lys
    290                 295                 300

Lys Glu Gly Leu Arg Asp Asp Leu Asp Asp Ile Asp Glu Asn Asp Val
305                 310                 315                 320

Gly Ala Lys Arg Arg Leu Ala Leu Leu Asp Ala Met Val Glu Met Ala
                325                 330                 335

Lys Asn Pro Asp Ile Glu Trp Asn Glu Lys Asp Ile Met Asp Glu Val
            340                 345                 350

Asn Thr Ile Met Phe Glu Gly His Asp Thr Thr Ser Ala Gly Ser Ser
        355                 360                 365

Phe Ala Leu Cys Met Leu Gly Ile His Lys His Ile Gln Glu Arg Val
    370                 375                 380

Phe Ala Glu Gln Lys Ser Ile Phe Gly Asp Asn Met Gln Arg Asp Cys
385                 390                 395                 400

Thr Phe Ala Asp Thr Met Glu Met Lys Tyr Leu Glu Arg Val Ile Leu
                405                 410                 415

Glu Thr Leu Arg Met Tyr Pro Pro Val Pro Leu Ile Ala Arg Arg Leu
            420                 425                 430

Asp His Asp Val Lys Leu Val Ser Gly Pro Tyr Thr Val Pro Lys Gly
        435                 440                 445

Thr Thr Val Val Leu Leu Gln Tyr Cys Val His Arg Arg Pro Asp Ile
    450                 455                 460

Tyr Pro Asn Pro Thr Glu Phe Asp Pro Asp Asn Phe Leu Pro Glu Arg
465                 470                 475                 480

Ala Ala Asn Arg His Tyr Tyr Ser Phe Ile Pro Phe Ser Ala Gly Pro
                485                 490                 495

Arg Ser Cys Val Gly Arg Lys Tyr Ala Met Leu Lys Leu Lys Val Leu
            500                 505                 510

Leu Ser Thr Ile Val Arg Asn Phe Ile Val His Ser Thr Asp Thr Glu
        515                 520                 525

Ala Asp Phe Lys Leu Gln Ala Asp Ile Ile Leu Lys Leu Glu Asn Gly
    530                 535                 540

Phe Asn Ile Ser Leu Glu Pro Arg Lys Tyr Gln Thr Val Ala
545                 550                 555

<210> SEQ ID NO 9
<211> LENGTH: 540
<212> TYPE: PRT
<213> ORGANISM: Drosophila ananassae

<400> SEQUENCE: 9

Met Thr Val Glu Ala Ala Ala Thr Ser Thr Ser Leu Leu Gly Tyr Ser
1               5                   10                  15

Pro Thr Leu Thr Thr Leu Val Ala Thr Met Val Ala Leu Gly Leu Tyr
                20                  25                  30

```
Glu Tyr Trp Arg Arg Asn Thr Arg Glu Tyr Arg Met Val Ala Asn Ile
             35                  40                  45

Pro Ser Pro Pro Glu Leu Pro Leu Leu Gly Gln Ala His Leu Ala Ala
 50                  55                  60

Gly Leu Ser Asn Ala Glu Ile Met Asn Val Gly Leu Gly Tyr Leu Ser
 65                  70                  75                  80

Lys Tyr Gly Glu Thr Leu Lys Ala Trp Leu Gly Ser Val Leu Leu Val
             85                  90                  95

Phe Ile Thr Asn Pro Asn Asp Ile Glu Leu Ile Leu Ser Gly His Gln
            100                 105                 110

His Leu Thr Lys Ala Glu Glu Tyr Arg Tyr Phe Lys Pro Trp Phe Gly
            115                 120                 125

Asp Gly Leu Leu Ile Ser Asn Gly His His Trp Arg His His Arg Lys
            130                 135                 140

Met Ile Ala Pro Thr Phe His Gln Ser Ile Leu Lys Ser Phe Val Pro
145                 150                 155                 160

Thr Phe Val Asn His Ser Lys Ala Val Val Asp Arg Met Gly Leu Glu
            165                 170                 175

Ala Gly Lys Ser Phe Asp Val His Asp Tyr Met Ser Gln Thr Thr Val
            180                 185                 190

Asp Ile Leu Leu Ser Thr Ala Met Gly Val Lys Lys Leu Pro Glu Gly
            195                 200                 205

Asn Lys Ser Phe Glu Tyr Ala Gln Ala Val Val Asp Met Cys Asp Ile
            210                 215                 220

Ile His Lys Arg Gln Ile Lys Leu Leu Tyr Arg Leu Asp Ser Ile Tyr
225                 230                 235                 240

Lys Phe Thr Lys Leu Arg Glu Lys Gly Asp Arg Met Met Asn Ile Ile
            245                 250                 255

Leu Gly Met Thr Ser Lys Val Val Lys Asp Arg Lys Glu Asn Phe Gln
            260                 265                 270

Glu Glu Ser Arg Ala Ile Val Glu Glu Ile Thr Thr Pro Ala Thr Pro
            275                 280                 285

Ala Ala Lys Lys Glu Gly Leu Arg Asp Asp Leu Asp Ile Asp Glu
            290                 295                 300

Asn Asp Val Gly Ala Lys Arg Arg Leu Ala Leu Leu Asp Ala Met Val
305                 310                 315                 320

Glu Met Ala Lys Asn Pro Asp Ile Glu Trp Asn Glu Lys Asp Ile Ile
            325                 330                 335

Asp Glu Val Asn Thr Ile Met Phe Glu Gly His Asp Thr Thr Ser Ala
            340                 345                 350

Gly Ser Ser Phe Ala Leu Cys Met Met Gly Ile His Lys Asp Ile Gln
            355                 360                 365

Glu Lys Val Phe Ala Glu Gln Lys Ala Ile Phe Gly Asp Asn Met Leu
            370                 375                 380

Arg Asp Cys Thr Phe Ala Asp Thr Met Glu Met Lys Tyr Leu Glu Arg
385                 390                 395                 400

Val Ile Leu Glu Thr Leu Arg Leu Tyr Pro Pro Val Pro Leu Ile Ala
            405                 410                 415

Arg Arg Val Asp Tyr Asp Leu Lys Leu Ala Ser Gly Pro Tyr Thr Val
            420                 425                 430

Pro Lys Gly Thr Thr Val Ile Val Leu Gln Tyr Cys Val His Arg Arg
            435                 440                 445

Pro Asp Ile Tyr Pro Asn Pro Thr Lys Phe Asp Pro Asp Asn Phe Leu
```

```
                450                 455                 460
Pro Glu Arg Met Ala Asn Arg His Tyr Tyr Ala Phe Ile Pro Phe Ser
465                 470                 475                 480

Ala Gly Pro Arg Ser Cys Val Gly Arg Lys Tyr Ala Met Leu Lys Leu
                485                 490                 495

Lys Val Leu Leu Ser Thr Ile Val Arg Asn Tyr Ile Val His Ser Thr
                500                 505                 510

Asp Thr Glu Ala Asp Phe Lys Leu Gln Ala Asp Ile Ile Leu Lys Leu
                515                 520                 525

Glu Asn Gly Phe Asn Ile Ser Leu Glu Lys His Met
                530                 535                 540

<210> SEQ ID NO 10
<211> LENGTH: 562
<212> TYPE: PRT
<213> ORGANISM: Drosophila grimshawi

<400> SEQUENCE: 10

Met Ser Val Glu Thr Val Gln Glu Thr Leu Gln Gln Ala Ala Ser Gly
1               5                   10                  15

Gly Gly Gly Tyr Ile Leu Ser Pro Leu Thr Gly Val Leu Gly Thr
                20                  25                  30

Ile Leu Ile Met Ala Leu Tyr Glu Tyr Trp His Arg Asn Ser Arg Glu
                35                  40                  45

Tyr Arg Met Val Glu Asn Ile Pro Ser Pro Thr Leu Pro Leu Val
                50                  55                  60

Gly Met Ala His Leu Val Val Gly Leu Ser Asn Ala Glu Ile Leu Ser
65              70                  75                  80

Val Gly Leu Gly Tyr Leu Asn Lys Tyr Gly Glu Thr Met Lys Ala Trp
                85                  90                  95

Leu Gly Asn Val Leu Val Phe Leu Thr Asn Pro Ser Asp Ile Glu
                100                 105                 110

Leu Ile Leu Ser Gly His Gln His Leu Thr Lys Ala Glu Glu Tyr Arg
                115                 120                 125

Tyr Phe Lys Pro Trp Phe Gly Asp Gly Leu Leu Ile Ser Asn Gly His
                130                 135                 140

His Trp Arg His His Arg Lys Met Ile Ala Pro Thr Phe His Gln Ser
145                 150                 155                 160

Ile Leu Lys Ser Phe Val Pro Thr Phe Val Asp His Ser Lys Ala Val
                165                 170                 175

Ser Ala Arg Met Gly Lys Glu Ser Gly Lys Pro Phe Asp Val His Asp
                180                 185                 190

Tyr Met Ser Gln Thr Thr Val Asp Ile Leu Leu Ser Thr Ala Met Gly
                195                 200                 205

Val Lys Lys Leu Pro Glu Gly Asn Thr Ser Phe Glu Tyr Ala Gln Ala
210                 215                 220

Val Val Asp Met Cys Asp Ile Ile His Lys Arg Gln Val Lys Leu Leu
225                 230                 235                 240

Tyr Arg Leu Asp Ser Ile Tyr Lys Phe Thr Lys Leu Arg Glu Lys Gly
                245                 250                 255

Asp Arg Met Met Asn Ile Ile Leu Gly Met Thr Arg Lys Val Val Lys
                260                 265                 270

Asp Arg Lys Asp Asn Phe Ile Thr Glu Ser Arg Pro Ile Ile Asp Glu
                275                 280                 285

Val Glu Glu Thr Pro Asn Pro Lys Leu Ser Arg Ala Thr Pro Pro Ala
```

```
                    290                 295                 300
Ala Ala Ala Lys Lys Glu Gly Leu Arg Asp Asp Leu Asp Asp Ile Asp
305                 310                 315                 320

Glu Asn Asp Val Gly Ala Lys Arg Arg Leu Ala Leu Leu Asp Ala Met
                325                 330                 335

Val Glu Met Ala Lys Asn Pro Glu Ile Glu Trp Asn Glu Lys Asp Ile
            340                 345                 350

Met Asp Glu Val Asn Thr Ile Met Phe Glu Gly His Asp Thr Thr Ser
        355                 360                 365

Ala Gly Ser Ser Phe Ala Leu Cys Met Leu Gly Ile His Lys Asp Ile
    370                 375                 380

Gln Glu Arg Val Phe Ala Glu Gln Lys Ala Ile Phe Gly Asp Lys Met
385                 390                 395                 400

Gln Arg Asp Cys Thr Phe Ala Asp Thr Met Glu Met Lys Tyr Leu Glu
                405                 410                 415

Arg Val Ile Leu Glu Thr Leu Arg Met Tyr Pro Pro Val Pro Leu Ile
            420                 425                 430

Ala Arg Arg Leu Asp His Asp Val Lys Leu Thr Ser Gly Pro Tyr Thr
        435                 440                 445

Val Pro Lys Gly Thr Thr Val Val Leu Gln Tyr Cys Val His Arg
    450                 455                 460

Arg Ala Asp Ile Tyr Pro Asn Pro Thr Lys Phe Asp Pro Asp Asn Phe
465                 470                 475                 480

Leu Pro Glu Arg Ala Ala Asn Arg His Tyr Tyr Ser Phe Ile Pro Phe
                485                 490                 495

Ser Ala Gly Pro Arg Ser Cys Val Gly Arg Lys Tyr Ala Met Leu Lys
            500                 505                 510

Leu Lys Val Leu Leu Ser Thr Ile Val Arg Asn Tyr Ile Val His Ser
        515                 520                 525

Thr Asp Thr Glu Ala Asp Phe Lys Leu Gln Ala Asp Ile Ile Leu Lys
    530                 535                 540

Leu Glu Asn Gly Phe Asn Ile Ser Leu Glu Pro Arg Lys Tyr Gln Thr
545                 550                 555                 560

Val Ala

<210> SEQ ID NO 11
<211> LENGTH: 505
<212> TYPE: PRT
<213> ORGANISM: Drosophila willistoni

<400> SEQUENCE: 11

Met Val Ser Asn Ile Pro Ser Pro Pro Gly Leu Pro Leu Leu Gly Gln
1               5                   10                  15

Ala His Leu Ala Ala Gly Leu Ser Asn Ala Glu Ile Met Ser Val Gly
            20                  25                  30

Met Gly Tyr Leu Asn Lys Tyr Gly Glu Thr Val Lys Ala Trp Leu Gly
        35                  40                  45

His Val Leu Leu Val Phe Leu Thr Asn Pro Asn Asp Ile Glu Leu Ile
    50                  55                  60

Leu Ser Gly His Gln His Leu Thr Lys Ala Glu Glu Tyr Arg Tyr Phe
65                  70                  75                  80

Lys Pro Trp Phe Gly Asp Gly Leu Leu Ile Ser Asn Gly His Trp
                85                  90                  95

Arg His His Arg Lys Met Ile Ala Pro Thr Phe His Gln Ser Ile Leu
            100                 105                 110
```

Lys Ser Phe Val Pro Thr Phe Val Asp His Ser Lys Asn Val Val Ala
            115                 120                 125

Arg Met Asp Thr Glu Ala Gly Lys Ser Phe Asp Val His Asp Tyr Met
    130                 135                 140

Ser Gln Thr Thr Val Asp Ile Leu Leu Ser Thr Ala Met Gly Val Lys
145                 150                 155                 160

Lys Leu Pro Glu Gly Asn Lys Ser Phe Glu Tyr Ala Gln Ala Val Val
                165                 170                 175

Asp Met Cys Asp Ile Ile His Lys Arg Gln Ile Lys Leu Leu Tyr Arg
            180                 185                 190

Leu Asp Ser Ile Tyr Lys Phe Thr Lys Leu Arg Glu Lys Gly Asp Lys
        195                 200                 205

Met Met Asn Ile Ile Leu Gly Met Thr Ser Lys Val Val Lys Asp Arg
210                 215                 220

Lys Glu Asn Phe Gln Ala Asp Thr Arg Ala Ile Ile Glu Glu Glu Leu
225                 230                 235                 240

Thr Lys Pro Ala Ala Thr Ser Pro Ser Ala Lys Lys Glu Gly Leu Arg
                245                 250                 255

Asp Asp Leu Asp Asp Ile Asp Glu Asn Asp Val Gly Ala Lys Arg Arg
            260                 265                 270

Leu Ala Leu Leu Asp Ala Met Val Glu Met Ala Lys Asn Pro Asp Ile
        275                 280                 285

Glu Trp Asn Glu Lys Asp Ile Ile Asp Glu Val Asn Thr Ile Met Phe
290                 295                 300

Glu Gly His Asp Thr Thr Ser Ala Gly Ser Ser Phe Ala Leu Cys Met
305                 310                 315                 320

Met Gly Ile His Lys His Ile Gln Glu Arg Val Phe Ala Glu Gln Lys
                325                 330                 335

Ala Ile Phe Gly Asp Asn Met Gln Arg Asp Cys Thr Phe Ala Asp Ala
            340                 345                 350

Met Glu Met Lys Tyr Leu Glu Arg Val Ile Leu Glu Thr Leu Arg Leu
        355                 360                 365

Tyr Pro Pro Val Pro Leu Ile Ala Arg Arg Leu Asp His Asp Leu Lys
370                 375                 380

Leu Ala Ser Gly Pro Tyr Thr Val Pro Lys Gly Thr Thr Val Ile Val
385                 390                 395                 400

Leu Gln Tyr Cys Val His Arg Arg Pro Asp Ile Tyr Pro Asn Pro Thr
                405                 410                 415

Thr Phe Asp Pro Asp Asn Phe Leu Pro Glu Arg Met Ala Asn Arg His
            420                 425                 430

Tyr Tyr Ala Phe Ile Pro Phe Ser Ala Gly Pro Arg Ser Cys Val Gly
        435                 440                 445

Arg Lys Tyr Ala Met Leu Lys Leu Lys Val Leu Leu Ser Thr Ile Val
450                 455                 460

Arg Asn Tyr Ile Ile His Ser Thr Asp Thr Glu Ala Asp Phe Lys Leu
465                 470                 475                 480

Gln Ala Asp Ile Ile Leu Lys Leu Glu Asn Gly Phe Asn Ile Ser Leu
                485                 490                 495

Glu Lys Arg Lys Tyr Pro Thr Val Ala
            500                 505

<210> SEQ ID NO 12
<211> LENGTH: 557
<212> TYPE: PRT

<213> ORGANISM: Culex quinquefasciatus

<400> SEQUENCE: 12

```
Met Asn Val Glu Phe Val His Glu Arg Ser Ser Leu Ala Ala Leu Ala
1               5                   10                  15

Met Pro Thr Val Ile Val Met Thr Leu Val Leu Val Ser Val Leu
            20                  25                  30

Phe His Met Trp Met Leu Ser Arg Arg Tyr Val Lys Leu Gly Asn Met
        35                  40                  45

Ile Pro Gly Pro Arg Ala Tyr Pro Leu Ile Gly Asn Ala Asn Met Leu
    50                  55                  60

Leu Gly Lys Ser His Asp Glu Ile Met Lys Arg Ala Ile Glu Leu Ser
65                  70                  75                  80

Phe Val Tyr Gly Ser Val Ala Arg Gly Trp Leu Gly Tyr His Leu Val
                85                  90                  95

Val Phe Leu Thr Glu Pro Ala Asp Ile Glu Leu Ile Leu Asn Ser Tyr
            100                 105                 110

Val His Leu Thr Lys Ser Asn Glu Tyr Arg Phe Phe Lys Pro Trp Leu
        115                 120                 125

Gly Asp Gly Leu Leu Ile Ser Ser Gly Asp Lys Trp Lys Ser His Arg
130                 135                 140

Lys Leu Ile Ala Pro Ala Phe His Gln Asn Val Leu Lys Thr Phe Ile
145                 150                 155                 160

Asp Val Phe Asn Asp Asn Ser Leu Ala Val Val Glu Arg Met Arg Lys
                165                 170                 175

Glu Val Gly Lys Val Phe Asp Val His Asp Tyr Met Ser Glu Val Thr
            180                 185                 190

Val Asp Ile Leu Leu Glu Thr Ala Met Gly Ser Asn Arg Thr Gly Glu
        195                 200                 205

Asn Lys Glu Gly Phe Asp Tyr Ala Met Ala Val Met Lys Met Cys Asp
210                 215                 220

Ile Leu His Ser Arg Gln Ile Lys Ile His Leu Arg Met Asp Pro Ile
225                 230                 235                 240

Phe Asn Met Thr Lys Thr Lys Lys Glu Gln Glu Arg Leu Leu Gly Ile
                245                 250                 255

Ile His Gly Leu Thr Arg Lys Val Lys Gln Lys Lys Glu Leu Phe
            260                 265                 270

Glu Lys Asn Leu Ala Glu Gly Lys Leu Pro Ser Pro Ser Leu Ser Glu
        275                 280                 285

Ile Ile Gly Lys Glu Glu Glu Ser Ser Gly Thr Thr Lys Val Glu Glu
290                 295                 300

Pro Ala Val Ile Ser Gln Gly Ser Met Leu Arg Asp Asp Leu Asp Ala
305                 310                 315                 320

Ile Asp Glu Asn Asp Ile Gly Glu Lys Arg Arg Leu Ala Phe Leu Asp
                325                 330                 335

Leu Met Ile Glu Thr Ala Lys Thr Gly Ala Asp Leu Ser Asp Glu Glu
            340                 345                 350

Ile Lys Glu Glu Val Asp Thr Ile Met Phe Glu Gly His Asp Thr Thr
        355                 360                 365

Ala Ala Gly Ser Ser Phe Val Leu Cys Leu Leu Gly Ile His Gln Asp
370                 375                 380

Ile Gln Asp Arg Val Tyr Lys Glu Ile Lys Gln Ile Phe Gly Asp Ser
385                 390                 395                 400

Lys Arg Lys Ala Thr Phe Asn Asp Thr Met Glu Met Lys Tyr Leu Glu
```

```
                              405                 410                 415
Arg Val Ile Phe Glu Thr Leu Arg Met Tyr Pro Pro Val Pro Ala Ile
                420                 425                 430

Ala Arg Lys Leu Thr Gln Glu Val Arg Leu Ala Ser His Asp Tyr Val
            435                 440                 445

Val Pro Ser Gly Thr Thr Val Val Ile Gly Thr Tyr Lys Leu His Arg
        450                 455                 460

Arg Glu Asp Ile Tyr Pro Asn Pro Asp Val Phe Asn Pro Asp Asn Phe
465                 470                 475                 480

Leu Pro Glu Arg Thr Ser Asn Arg His Tyr Tyr Ser Tyr Ile Pro Phe
                485                 490                 495

Ser Ala Gly Pro Arg Ser Cys Val Gly Arg Lys Tyr Ala Met Leu Lys
            500                 505                 510

Leu Lys Val Leu Leu Thr Thr Ile Leu Arg Asn Tyr Arg Val Val Ser
        515                 520                 525

Asn Leu Lys Glu Ser Asp Phe Lys Leu Gln Ala Asp Ile Ile Leu Lys
    530                 535                 540

Arg Thr Asp Gly Phe Arg Ile Gln Leu Glu Pro Arg Val
545                 550                 555

<210> SEQ ID NO 13
<211> LENGTH: 560
<212> TYPE: PRT
<213> ORGANISM: Aedes aegypti

<400> SEQUENCE: 13

Val Ser Gly Val Ile Tyr Lys Met Ser Ala Glu Ile Val Ala Glu Arg
1               5                   10                  15

Gly Ser Ser Leu Val Ser Leu Ala Val Pro Met Val Ile Phe Met Thr
                20                  25                  30

Leu Val Leu Val Ala Ser Ala Leu Phe His Phe Trp Met Ile Ser Arg
            35                  40                  45

Arg Tyr Val Gln Leu Gly Asn Lys Ile Pro Gly Pro Arg Ala Tyr Pro
        50                  55                  60

Phe Ile Gly Asn Ala Asn Met Leu Leu Gly Met Asn His Asn Glu Ile
65                  70                  75                  80

Met Glu Arg Ala Met Gln Leu Ser Tyr Ile Tyr Gly Ser Val Ala Arg
                85                  90                  95

Gly Trp Leu Gly Tyr His Leu Val Val Phe Leu Thr Glu Pro Ala Asp
            100                 105                 110

Ile Glu Ile Ile Leu Asn Ser Tyr Val His Leu Thr Lys Ser Ser Glu
        115                 120                 125

Tyr Arg Phe Phe Lys Pro Trp Leu Gly Asp Gly Leu Leu Ile Ser Ser
    130                 135                 140

Gly Glu Lys Trp Arg Ser His Arg Lys Leu Ile Ala Pro Ala Phe His
145                 150                 155                 160

Met Asn Val Leu Lys Thr Phe Val Asp Val Phe Asn Asp Asn Ser Leu
                165                 170                 175

Ala Val Val Glu Arg Met Arg Lys Glu Val Gly Lys Glu Phe Asp Val
            180                 185                 190

His Asp Tyr Met Ser Glu Val Thr Val Asp Ile Leu Leu Glu Thr Ala
        195                 200                 205

Met Gly Ser Gln Arg Thr Ser Glu Ser Lys Glu Gly Phe Asp Tyr Ala
    210                 215                 220

Met Ala Val Met Lys Met Cys Asp Ile Leu His Ser Arg Gln Leu Lys
```

```
                225                 230                 235                 240
Phe His Leu Arg Met Asp Ser Val Phe Asn Phe Thr Lys Ile Lys Gln
                245                 250                 255

Glu Gln Glu Arg Leu Leu Gly Ile Ile His Gly Leu Thr Arg Lys Val
            260                 265                 270

Val Lys Gln Lys Lys Glu Leu Phe Glu Lys Asn Phe Ala Asp Gly Lys
        275                 280                 285

Leu Pro Ser Pro Ser Leu Ser Glu Ile Ile Ala Lys Glu Glu Ser Glu
    290                 295                 300

Ser Lys Glu Ser Leu Pro Val Ile Ser Gln Gly Ser Leu Leu Arg Asp
305                 310                 315                 320

Asp Leu Asp Phe Asn Asp Glu Asn Asp Ile Gly Glu Lys Arg Arg Leu
                325                 330                 335

Ala Phe Leu Asp Leu Met Ile Glu Thr Ala Lys Ser Gly Ala Asp Leu
            340                 345                 350

Thr Asp Glu Glu Ile Lys Glu Glu Val Asp Thr Ile Met Phe Glu Gly
        355                 360                 365

His Asp Thr Thr Ala Ala Gly Ser Ser Phe Val Leu Cys Leu Leu Gly
    370                 375                 380

Ile His Gln Asp Val Gln Asp Arg Val Tyr Lys Glu Ile Tyr Gln Ile
385                 390                 395                 400

Phe Gly Asn Ser Lys Arg Lys Ala Thr Phe Asn Asp Thr Leu Glu Met
                405                 410                 415

Lys Tyr Leu Glu Arg Val Ile Phe Glu Thr Leu Arg Met Tyr Pro Pro
            420                 425                 430

Val Pro Val Ile Ala Arg Lys Val Thr Gln Asp Val Arg Leu Ala Ser
        435                 440                 445

His Asp Tyr Val Val Pro Ala Gly Thr Thr Val Val Ile Gly Thr Tyr
    450                 455                 460

Lys Val His Arg Arg Ala Asp Ile Tyr Pro Asn Pro Asp Val Phe Asn
465                 470                 475                 480

Pro Asp Asn Phe Leu Pro Glu Arg Thr Gln Asn Arg His Tyr Tyr Ser
                485                 490                 495

Tyr Ile Pro Phe Ser Ala Gly Pro Arg Ser Cys Val Gly Arg Lys Tyr
            500                 505                 510

Ala Met Leu Lys Leu Lys Val Leu Leu Ser Thr Ile Leu Arg Asn Tyr
        515                 520                 525

Arg Val Val Ser Asn Leu Lys Glu Ser Asp Phe Lys Leu Gln Gly Asp
    530                 535                 540

Ile Ile Leu Lys Arg Thr Asp Gly Phe Arg Ile Gln Leu Glu Pro Arg
545                 550                 555                 560

<210> SEQ ID NO 14
<211> LENGTH: 566
<212> TYPE: PRT
<213> ORGANISM: Aedes aegypti

<400> SEQUENCE: 14

Met Ser Ala Thr Val Ala Pro Ala Asp Pro Val Met Ala Asn Ala Asn
1               5                   10                  15

Ile Ala Ser Pro Met Asn Val Phe Tyr Phe Leu Leu Ala Pro Ala Leu
            20                  25                  30

Leu Leu Trp Phe Ile Tyr Trp Arg Ile Ser Arg Gln His Met Leu Lys
        35                  40                  45

Leu Ala Glu Lys Ile Pro Gly Pro Pro Gly Leu Pro Leu Leu Gly Asn
```

```
               50                  55                  60
Ala Leu Glu Leu Ile Gly Thr Ser His Ser Val Phe Arg Asn Val Ile
 65                  70                  75                  80

Glu Lys Gly Lys Asp Phe Asn Gln Val Ile Lys Ile Trp Ile Gly Pro
                 85                  90                  95

Lys Leu Ile Val Phe Leu Val Asp Pro Arg Asp Val Glu Leu Leu Leu
                    100                 105                 110

Ser Ser His Val Tyr Ile Asp Lys Ser Pro Glu Tyr Arg Phe Phe Lys
            115                 120                 125

Pro Trp Leu Gly Asn Gly Leu Leu Ile Ser Thr Gly His Lys Trp Arg
        130                 135                 140

Gln His Arg Lys Leu Ile Ala Pro Thr Phe His Leu Asn Val Leu Lys
145                 150                 155                 160

Ser Phe Ile Asp Leu Phe Asn Glu Asn Ser Arg Leu Val Val Glu Lys
                    165                 170                 175

Met His Lys Glu Ala Gly Lys Thr Phe Asp Cys His Asp Tyr Met Ser
                180                 185                 190

Glu Cys Thr Val Glu Ile Leu Leu Glu Thr Ala Met Gly Val Ser Lys
            195                 200                 205

Lys Thr Gln Asp Gln Ser Gly Phe Asp Tyr Ala Met Ala Val Met Lys
        210                 215                 220

Met Cys Asp Ile Leu His Leu Arg His Arg Lys Met Trp Leu Tyr Pro
225                 230                 235                 240

Asp Leu Phe Phe Asn Met Ser Gln Tyr Ala Lys Arg Gln Val Lys Leu
                    245                 250                 255

Leu Asp Thr Ile His Ser Leu Thr Arg Lys Val Ile Arg Asn Lys Lys
                260                 265                 270

Ala Ala Phe Ala Thr Gly Thr Arg Gly Ser Leu Ala Thr Thr Ser Ile
            275                 280                 285

Lys Thr Ala Glu Phe Glu Lys Pro Lys Ser Asn Ile Asn Thr Asn Ser
        290                 295                 300

Val Glu Gly Leu Ser Phe Gly Gln Ser Ala Asn Leu Lys Asp Asp Leu
305                 310                 315                 320

Asp Val Asp Glu Asn Asp Val Gly Glu Lys Lys Arg Leu Ala Phe Leu
                    325                 330                 335

Asp Leu Leu Leu Glu Ser Ala Glu Asn Gly Ala Leu Ile Ser Asp Glu
                340                 345                 350

Glu Ile Lys Asn Gln Val Asp Thr Ile Met Phe Glu Gly His Asp Thr
            355                 360                 365

Thr Ala Ala Gly Ser Ser Phe Phe Leu Ser Met Met Gly Ile His Gln
        370                 375                 380

His Ile Gln Asp Lys Val Ile Gln Glu Leu Asp Asp Ile Phe Gly Asp
385                 390                 395                 400

Ser Asp Arg Pro Ala Thr Phe Gln Asp Thr Leu Glu Met Lys Tyr Leu
                    405                 410                 415

Glu Arg Cys Leu Met Glu Thr Leu Arg Met Tyr Pro Pro Val Pro Ile
                420                 425                 430

Ile Ala Arg Ser Leu Lys Gln Asp Leu Lys Leu Ala Ser Ser Asp Leu
            435                 440                 445

Val Val Pro Ser Gly Ala Thr Ile Val Val Ala Thr Tyr Lys Leu His
        450                 455                 460

Arg Leu Glu Thr Ile Tyr Pro Asn Pro Asn Val Phe Asp Pro Asp Asn
465                 470                 475                 480
```

```
Phe Leu Pro Glu Arg Gln Ala Asn Arg His Tyr Tyr Ala Phe Val Pro
                485                 490                 495

Phe Ser Ala Gly Pro Arg Ser Cys Val Gly Arg Lys Tyr Ala Met Leu
            500                 505                 510

Lys Leu Lys Val Ile Leu Ser Thr Ile Leu Arg Asn Phe Arg Val Ile
        515                 520                 525

Ser Asp Leu Lys Glu Glu Asp Phe Lys Leu Gln Ala Asp Ile Ile Leu
    530                 535                 540

Lys Arg Glu Glu Gly Phe Gln Ile Arg Leu Glu Pro Arg Gln Arg Lys
545                 550                 555                 560

Pro Lys Ala Ala Lys Ala
                565

<210> SEQ ID NO 15
<211> LENGTH: 552
<212> TYPE: PRT
<213> ORGANISM: Nasonia vitripennis

<400> SEQUENCE: 15

Met Asp Ala Val Pro Met Ser Thr Ser Tyr Leu Pro Ala Thr Leu Phe
1               5                   10                  15

Trp Pro Leu Val Leu Ile Ala Ala Leu Ala Ala Val His Tyr Tyr
            20                  25                  30

Ile Glu Thr Ser Arg Ile Val Arg Leu Gly Asn Lys Leu Pro Gly Pro
            35                  40                  45

Lys Thr Val Pro Phe Phe Gly Asn Ala Leu Met Ala Leu Gly Val Gln
        50                  55                  60

Pro Lys Asp Val Leu Thr Glu Val Met Lys Tyr Asp Ile Tyr Gly Asn
65                  70                  75                  80

Val Ala Arg Ala Phe Leu Gly Pro Lys Leu Val Phe Leu Val Asp
                85                  90                  95

Pro Arg Asp Val Glu Ile Ile Leu Gly Ser His Val His Ile Asp Lys
            100                 105                 110

Ser Pro Glu Tyr Arg Tyr Phe Ala Pro Trp Leu Gly Glu Gly Leu Leu
        115                 120                 125

Ile Ser Thr Gly Glu Lys Trp Arg Ser His Arg Lys Ile Ile Ala Pro
130                 135                 140

Thr Phe His Leu Asn Val Leu Lys Ser Phe Val Pro Leu Phe Tyr Glu
145                 150                 155                 160

Asn Ser Ile Asp Leu Val Lys Arg Leu Lys Ser Glu Val Gly Lys Glu
                165                 170                 175

Phe Asp Cys His Asp Tyr Met Ser Gly Ile Thr Val Asp Ile Leu Leu
            180                 185                 190

Glu Thr Ala Met Gly Val Arg Gly Thr Gln Lys Glu Lys Ser Ser Tyr
        195                 200                 205

Asp Tyr Ala Met Ala Val Met Lys Met Cys Asn Ile Ile His Gln Arg
    210                 215                 220

Gln Tyr Asn Phe Met Leu Arg Leu Asp Thr Phe Phe Gln Phe Thr Ser
225                 230                 235                 240

Phe Ala Lys Gln Gln Thr Lys Phe Leu Asp Ile Ile His Gly Leu Thr
                245                 250                 255

Lys Arg Val Ile Lys Lys Arg Asn Val Glu Phe Lys Asp Lys Met Asp
            260                 265                 270

Ser Pro Met Met Asn Ser Ile Met Lys Glu Leu Lys Lys Asp Ser Thr
        275                 280                 285
```

Glu Ile Val Asp Glu Lys Gln Pro Glu Glu Gln Lys Met Arg Tyr Val
            290                 295                 300

Arg Asp Asp Leu Asp Glu Ile Asp Glu Asn Asp Val Gly Glu Lys Arg
305                 310                 315                 320

Arg Leu Ala Phe Leu Asp Leu Met Leu Glu Met Arg Lys Asn Gly Glu
                325                 330                 335

Gln Leu Thr Asp Glu Glu Ile Lys Glu Val Asp Thr Ile Met Phe
            340                 345                 350

Glu Gly His Asp Thr Thr Ala Ala Gly Ser Ser Phe Val Leu Cys Val
                355                 360                 365

Leu Gly Ile His Gln Asp Val Gln Asp Arg Val Ile Glu Glu Leu Asn
370                 375                 380

Glu Ile Phe Lys Gly Ser Asp Arg Pro Cys Thr Phe Gln Asp Thr Leu
385                 390                 395                 400

Glu Met Lys Tyr Leu Glu Arg Val Ile Leu Glu Thr Leu Arg Leu Phe
                405                 410                 415

Pro Pro Val Pro Ala Ile Ala Arg Gln Leu Asn Gln Asp Val Lys Leu
                420                 425                 430

Ala Ser Gly Asp Tyr Ile Leu Pro Ser Gly Cys Thr Val Val Ile Pro
                435                 440                 445

Gln Phe Lys Ile His Arg Leu Lys Glu Tyr Tyr Pro Asn Pro Asp Val
            450                 455                 460

Phe Asp Pro Asp Asn Phe Leu Pro Asp Lys Thr Gln Asp Arg His Tyr
465                 470                 475                 480

Tyr Ala Tyr Ile Pro Phe Ser Ala Gly Pro Arg Ser Cys Val Gly Arg
                485                 490                 495

Lys Tyr Ala Met Leu Lys Leu Lys Val Leu Leu Ser Thr Ile Leu Arg
            500                 505                 510

Asn Tyr Lys Ile Asn Ser Asp Leu Thr Glu Glu Asp Phe Lys Leu Gln
            515                 520                 525

Val Asp Ile Ile Leu Lys Arg Ser Asp Gly Phe Arg Ile Gln Ile Glu
530                 535                 540

Pro Arg Asn Gln Ala Val Ile Val
545                 550

<210> SEQ ID NO 16
<211> LENGTH: 561
<212> TYPE: PRT
<213> ORGANISM: Nasonia vitripennis

<400> SEQUENCE: 16

Met Ser Ala Ala Gly Pro Glu Val Val Ala Gly Ser Val Ala Ala
1               5                   10                  15

Ala Ala Ser Gly Phe Ser Ala Thr Ser Val Phe Phe Thr Leu Leu Val
                20                  25                  30

Pro Ala Ile Leu Leu Tyr Tyr Val Tyr Phe Arg Ile Ser Arg Arg His
            35                  40                  45

Met Ile Glu Leu Ser Asp Lys Ile Pro Gly Pro Lys Gly Leu Pro Leu
50                  55                  60

Leu Gly Asn Ala Leu Glu Leu Ile Gly Ser Ser Asp Thr Ile Phe Arg
65                  70                  75                  80

Asn Val Tyr Lys Arg Ser Phe Glu Phe Asp Gln Val Ile Lys Leu Trp
                85                  90                  95

Val Gly Pro Lys Leu Val Ile Phe Leu Ile Asp Pro Arg Asp Val Glu
            100                 105                 110

```
Val Ile Leu Ser Ser His Val Tyr Ile Asp Lys Ser Pro Glu Tyr Arg
            115                 120                 125

Phe Phe Gln Pro Trp Leu Gly Asn Gly Leu Leu Ile Ser Thr Gly Gln
130                 135                 140

Lys Trp Arg Ala His Arg Lys Leu Ile Ala Pro Thr Phe His Leu Asn
145                 150                 155                 160

Val Leu Lys Ser Phe Ile Asp Leu Phe Asn Ala Asn Ser Arg Ala Val
                165                 170                 175

Val Gln Lys Met Arg Lys Glu Asp Glu Arg Glu Phe Asp Ile His Asp
            180                 185                 190

Tyr Met Ser Glu Thr Thr Val Glu Ile Leu Leu Glu Ala Met Gly
            195                 200                 205

Val Ser Lys Ser Thr Gln Asp Lys Ser Gly Phe Glu Tyr Ala Met Ala
            210                 215                 220

Val Met Lys Met Cys Asp Ile Leu His Leu Arg His Thr Arg Val Trp
225                 230                 235                 240

Leu Arg Pro Asp Trp Leu Phe Asn Leu Thr Lys Tyr Gly Lys Glu Gln
                245                 250                 255

Val His Leu Leu Asp Ile Ile His Gly Leu Thr Lys Lys Val Ile Ala
            260                 265                 270

Arg Lys Lys Glu Asp Tyr Lys Ser Gly Lys Arg Asn Phe Val Asp Thr
            275                 280                 285

Ser Ala Ala Lys Asp Asn Lys Ser Thr Thr Val Val Glu Gly Leu
290                 295                 300

Ser Phe Gly Gln Ser Ala Gly Leu Lys Asp Asp Leu Asp Val Asp Asp
305                 310                 315                 320

Asn Asp Val Gly Glu Lys Lys Arg Gln Ala Phe Leu Asp Leu Leu Val
                325                 330                 335

Glu Ala Ser Gln Asn Gly Val Val Leu Thr Asp Glu Glu Val Lys Glu
            340                 345                 350

Gln Val Asp Thr Ile Met Phe Glu Gly His Asp Thr Thr Ala Ala Gly
            355                 360                 365

Ser Ser Phe Phe Leu Ser Met Met Gly Cys His Pro Asp Ile Gln Glu
            370                 375                 380

Lys Val Ile Gln Glu Leu Asp Glu Ile Phe Gly Asp Ser Asp Arg Pro
385                 390                 395                 400

Ala Thr Phe Gln Asp Thr Leu Glu Met Lys Tyr Leu Glu Arg Cys Leu
                405                 410                 415

Met Glu Thr Leu Arg Met Tyr Pro Pro Val Pro Ile Ile Ala Arg Glu
            420                 425                 430

Val Lys Thr Asp Leu Lys Leu Ala Ser Gly Asp Tyr Thr Ile Pro Ala
            435                 440                 445

Gly Cys Thr Val Val Ala Thr Phe Lys Leu His Arg Gln Pro His
450                 455                 460

Ile Tyr Pro Asn Pro Asp Val Phe Asn Pro Asp Asn Phe Leu Pro Glu
465                 470                 475                 480

Lys Thr Ala Asn Arg His Tyr Tyr Ala Phe Val Pro Phe Ser Ala Gly
                485                 490                 495

Pro Arg Ser Cys Val Gly Arg Lys Tyr Ala Met Leu Lys Leu Lys Ile
            500                 505                 510

Leu Leu Ser Thr Ile Leu Arg Asn Phe Arg Val Arg Ser Thr Val Lys
            515                 520                 525

Glu Glu Asp Phe Arg Leu Gln Ala Asp Ile Ile Leu Lys Arg Ala Glu
            530                 535                 540
```

```
Gly Phe Lys Val Lys Leu Glu Pro Arg Lys Arg Ala Ala Gly Leu Lys
545                 550                 555                 560
Ala
```

<210> SEQ ID NO 17
<211> LENGTH: 559
<212> TYPE: PRT
<213> ORGANISM: Chironomus tentans

<400> SEQUENCE: 17

```
Met Ala Val Glu Gln Ile Ile Gln Ser Ser Val Phe Ser Ser Pro Leu
1               5                   10                  15

Leu Met Pro Leu Leu Ala Ile Val Phe Val Leu Ala Ala Val His Phe
                20                  25                  30

Trp Gln Met Ser Arg Arg Glu Arg Lys Ile Gly Asp Leu Leu Pro Gly
            35                  40                  45

Pro Pro Thr Val Pro Ile Ile Gly Asn Ala Tyr Leu Phe Met Asn Gly
        50                  55                  60

Thr Asn His Glu Met Phe Lys Lys Ala Val Asp Leu Val Asn Cys Tyr
65                  70                  75                  80

Gly Ser Val Val Arg Gly Trp Val Gly His Lys Leu Leu Val Gly Leu
                85                  90                  95

Ser Asp Pro Arg Asp Val Glu Ile Ile Leu Gly Ser Gln Val His Ile
                100                 105                 110

Asp Lys Ser Asp Glu Tyr Arg Phe Phe Arg Pro Trp Leu Gly Asn Gly
            115                 120                 125

Leu Leu Ile Ser Ser Gly Asp Lys Trp Arg Thr His Arg Lys Leu Ile
        130                 135                 140

Ala Pro Ala Phe His Met Asn Val Leu Lys Ser Phe Met Ala Thr Phe
145                 150                 155                 160

Asn Asp Asn Ser Arg Phe Val Ile Lys Lys Leu Met Lys Glu Ala Gly
                165                 170                 175

Lys Glu Phe Asp Cys His Asp Tyr Met Ser Glu Ala Thr Val Asp Ile
                180                 185                 190

Leu Leu Glu Thr Ala Met Gly Ser Lys Arg Thr Ser Glu Ser Glu Glu
            195                 200                 205

Gly Phe Lys Tyr Ala Met Ala Val Met Lys Met Cys Asp Ile Leu His
        210                 215                 220

Arg Arg Gln Phe Lys Ile Phe Ser Arg Phe Glu Pro Phe Phe Thr Leu
225                 230                 235                 240

Thr Gly Met Lys Glu Gln Gln Lys Leu Leu Gly Ile Ile His Gly
                245                 250                 255

Met Thr Gln Arg Val Leu Asn Glu Lys Lys Ala Ile Phe Asp Lys Asn
                260                 265                 270

Leu Ser Glu Gly Asn Leu Pro Ser Pro Ser Leu Gln Glu Ile Ile Lys
            275                 280                 285

Thr Asp Ala Ser Val Asp Gln Ala Ile Lys Lys Ala Lys Ala Lys Ala
        290                 295                 300

Gln Asn Ile Asp Ala Gly Leu His Asp Asp Leu Asp Asp Ile Asp Glu
305                 310                 315                 320

Asn Asp Val Gly Glu Lys Arg Arg Leu Ala Phe Leu Asp Leu Met Ile
                325                 330                 335

Glu Thr Ser His Tyr Asn Pro Gln Leu Ser Gln Leu Glu Ile Lys
                340                 345                 350
```

```
Gln Gln Val Asp Thr Ile Met Phe Glu Gly His Asp Thr Ala Ala
        355                 360                 365
Gly Ser Ser Phe Thr Leu Cys Met Leu Gly Cys His Pro Asp Ile Gln
370                 375                 380
Glu Lys Val Tyr Gln Glu Gln Lys Ala Ile Phe Gly Asp Ser Asp Arg
385                 390                 395                 400
Asp Cys Thr Phe Ala Asp Thr Leu Glu Met Lys Tyr Leu Glu Arg Val
                405                 410                 415
Ile Phe Glu Thr Leu Arg Met Tyr Pro Pro Val Pro Leu Ile Ala Arg
                420                 425                 430
Lys Ile Asn Lys Asp Ile Arg Leu Ala Ser Cys Asp Gln Val Val Pro
                435                 440                 445
Ala Gly Thr Thr Ile Ile Ala Thr Val Lys Ile His Arg Arg Pro
450                 455                 460
Asp Ile Tyr Pro Asn Pro Asp Lys Phe Asp Pro Asp Asn Phe Leu Pro
465                 470                 475                 480
Glu Arg Thr Ser Asn Arg His Tyr Tyr Gly Phe Ile Pro Phe Ser Ala
                485                 490                 495
Gly Pro Arg Ser Cys Val Gly Arg Lys Tyr Ala Met Leu Lys Leu Lys
                500                 505                 510
Val Leu Leu Ser Thr Ile Val Arg Asn Phe Tyr Val Lys Ser Thr Val
                515                 520                 525
Pro Glu Lys Asp Phe Lys Leu Gln Ala Asp Ile Ile Leu Lys Arg Thr
                530                 535                 540
Asp Gly Phe Arg Ile Lys Leu Gly Pro Arg Lys Thr Lys Ala Asn
545                 550                 555

<210> SEQ ID NO 18
<211> LENGTH: 566
<212> TYPE: PRT
<213> ORGANISM: Anopheles gambiae

<400> SEQUENCE: 18

Val Ser Glu Ile Met Gly Ile Glu Thr Ile Pro Glu Arg Met Ala Met
1               5                   10                  15
Asp Glu Thr Val Pro Gly Ser Trp Val Leu Ser Val Thr Val Ala Thr
                20                  25                  30
Val Leu Leu Leu Val Ala Gly Thr Leu Phe His Leu Trp Met Gln Thr
                35                  40                  45
Arg Arg Tyr Val Gln Leu Gly Asn Leu Ile Pro Gly Pro Val Ala Tyr
        50                  55                  60
Pro Leu Ile Gly Asn Ala Asn Met Leu Leu Gly Lys Thr His Asn Gln
65                  70                  75                  80
Ile Met Glu Lys Ala Met Glu Leu Ser Tyr Ile Tyr Gly Thr Val Ala
                85                  90                  95
Arg Gly Trp Leu Gly Tyr His Leu Val Val Phe Leu Thr Glu Pro Ala
                100                 105                 110
Asp Val Glu Ile Ile Leu Asn Ser Tyr Val His Leu Glu Lys Ser Ser
                115                 120                 125
Glu Tyr Arg Phe Phe Lys Pro Trp Leu Gly Asp Gly Leu Leu Ile Ser
        130                 135                 140
Ser Gly Asp Lys Trp Lys Ser His Arg Lys Leu Ile Ala Pro Ala Phe
145                 150                 155                 160
His Gln Asn Val Leu Lys Thr Phe Ile Asp Val Phe Asn Asp Asn Ser
                165                 170                 175
```

```
Leu Ala Val Val Lys Arg Met Ser Lys Glu Val Gly His Val Phe Asp
            180                 185                 190
Cys His Asp Tyr Met Ser Glu Val Thr Val Asp Ile Leu Leu Glu Thr
        195                 200                 205
Ala Met Gly Ser Thr Arg Thr Gly Glu Asn Lys Glu Gly Phe Glu Tyr
    210                 215                 220
Ala Met Ala Val Met Lys Met Cys Asp Ile Leu His Lys Arg Gln Leu
225                 230                 235                 240
Lys Ile His Leu Arg Leu Asp Pro Leu Phe Asn Leu Thr Gly Val Lys
                245                 250                 255
Lys Glu Gln Glu Arg Leu Leu Gln Ile Ile His Gly Leu Thr Arg Lys
            260                 265                 270
Val Val Arg Glu Lys Lys Gln Leu Tyr Glu Arg Gln Met Ala Glu Gly
        275                 280                 285
Lys Met Pro Ser Pro Ser Leu Thr Glu Ile Ile Gly Lys Glu Glu Lys
    290                 295                 300
Pro Gly Glu Gly Gln Leu Gly Gly Ser Pro Ala Phe Ile Ser Gln Gly
305                 310                 315                 320
Ser Met Leu Arg Asp Asp Leu Asp Asp Asn Asp Glu Asn Asp Ile Gly
                325                 330                 335
Glu Lys Arg Arg Leu Ala Phe Leu Asp Leu Met Ile Glu Thr Ala Asn
            340                 345                 350
Asn Gly Ala Asn Ile Ser Asp Glu Glu Ile Lys Glu Val Asp Thr
        355                 360                 365
Ile Met Phe Glu Gly His Asp Thr Thr Ala Ala Gly Ser Ser Phe Val
    370                 375                 380
Leu Cys Leu Leu Gly Ile His Gln His Val Gln Glu Gln Val Tyr Ala
385                 390                 395                 400
Glu Leu Arg Gln Ile Phe Gly Asp Ser Lys Arg Lys Ala Thr Phe Gly
                405                 410                 415
Asp Thr Leu Glu Met Lys Tyr Leu Glu Arg Val Ile Phe Glu Thr Leu
            420                 425                 430
Arg Met Phe Pro Pro Val Pro Met Ile Ala Arg Lys Ile Asn Glu Asp
        435                 440                 445
Val Gln Leu Ala Ser Lys Asn Tyr Thr Ile Pro Ala Gly Thr Thr Val
    450                 455                 460
Val Ile Gly Thr Tyr Lys Ile His Arg Arg Glu Asp Leu Tyr Pro His
465                 470                 475                 480
Pro Glu Thr Phe Asn Pro Asp Asn Phe Leu Pro Glu Arg Thr Gln Asn
                485                 490                 495
Arg His Tyr Tyr Ser Tyr Ile Pro Phe Ser Ala Gly Pro Arg Ser Cys
            500                 505                 510
Val Gly Arg Lys Tyr Ala Met Leu Lys Leu Lys Val Leu Leu Ser Thr
        515                 520                 525
Val Leu Arg His Tyr Arg Val Val Ser Asn Leu Thr Glu Lys Asp Phe
    530                 535                 540
Lys Leu Gln Ala Asp Ile Ile Leu Lys Arg Thr Asp Gly Phe Gln Ile
545                 550                 555                 560
Gln Leu Glu Pro Arg Ala
                565

<210> SEQ ID NO 19
<211> LENGTH: 565
<212> TYPE: PRT
<213> ORGANISM: Anopheles gambiae
```

<400> SEQUENCE: 19

```
Met Ser Ala Thr Ile Ala His Thr Asp Gly Leu Asn Ser Ser Ala Asn
1               5                   10                  15

Ile Ile Ser Pro Ile Asn Met Phe Tyr Phe Leu Leu Thr Pro Ala Leu
            20                  25                  30

Leu Leu Trp Phe Phe Tyr Trp Arg Leu Ser Arg Arg His Met Leu Glu
        35                  40                  45

Leu Ala Glu Arg Ile Pro Gly Pro Lys Gly Leu Pro Leu Ile Gly Asn
50                  55                  60

Ala Leu Asp Leu Val Gly Ser Ser His Ser Val Phe Arg Thr Ile Ile
65                  70                  75                  80

Glu Lys Gly Lys Glu Tyr Asn Glu Val Ile Lys Ile Trp Ile Gly Pro
                85                  90                  95

Lys Leu Ile Val Phe Leu Val Asp Pro Arg Asp Ile Glu Leu Leu Leu
            100                 105                 110

Ser Ser His Val Tyr Ile Asp Lys Ser Pro Glu Tyr Arg Phe Phe Lys
        115                 120                 125

Pro Trp Leu Gly Asn Gly Leu Leu Ile Ser Thr Gly His Lys Trp Arg
130                 135                 140

Gln His Arg Lys Leu Ile Ala Pro Thr Phe His Leu Asn Val Leu Lys
145                 150                 155                 160

Ser Phe Ile Asp Leu Phe Asn Glu Asn Ser Arg Leu Val Val Lys Lys
                165                 170                 175

Met Gln Lys Glu Asn Gly Lys Val Phe Asp Cys His Asp Tyr Met Ser
            180                 185                 190

Glu Cys Thr Val Glu Ile Leu Leu Glu Thr Ala Met Gly Val Ser Lys
        195                 200                 205

Lys Thr Gln Asp Gln Ser Gly Tyr Asp Tyr Ala Met Ala Val Met Lys
210                 215                 220

Met Cys Asp Ile Leu His Leu Arg His Arg Lys Met Trp Leu Tyr Pro
225                 230                 235                 240

Asp Leu Phe Phe Asn Leu Thr Gln Tyr Ala Lys Lys Gln Val Lys Leu
                245                 250                 255

Leu Asn Thr Ile His Ser Leu Thr Lys Lys Val Ile Arg Asn Lys Lys
            260                 265                 270

Ala Ala Phe Asp Thr Gly Thr Arg Gly Ser Leu Ala Thr Thr Ser Ile
        275                 280                 285

Asn Thr Val Asn Ile Glu Lys Ser Lys Ser Asp Ser Thr Lys Thr Asn
290                 295                 300

Thr Val Glu Gly Leu Ser Phe Gly Gln Ser Ser Asn Leu Lys Asp Asp
305                 310                 315                 320

Leu Asp Val Glu Glu Asn Asp Val Gly Glu Lys Lys Arg Leu Ala Phe
                325                 330                 335

Leu Asp Leu Leu Leu Glu Ser Ala Glu Asn Gly Ala Leu Ile Ser Asp
            340                 345                 350

Glu Glu Ile Lys Asn Gln Val Asp Thr Ile Met Phe Glu Gly His Asp
        355                 360                 365

Thr Thr Ala Ala Gly Ser Ser Phe Leu Ser Met Met Gly Val His
370                 375                 380

Gln Gln Ile Gln Asp Lys Val Ile Gln Glu Leu Asp Glu Ile Phe Gly
385                 390                 395                 400

Glu Ser Asp Arg Pro Ala Thr Phe Gln Asp Thr Leu Glu Met Lys Tyr
                405                 410                 415
```

Leu Glu Arg Cys Leu Met Glu Thr Leu Arg Met Tyr Pro Pro Val Pro
            420                 425                 430

Ile Ile Ala Arg Ser Leu Lys Gln Asp Leu Lys Leu Ala Ser Ser Asp
            435                 440                 445

Ile Val Val Pro Ala Gly Ala Thr Ile Thr Val Ala Thr Phe Lys Leu
450                 455                 460

His Arg Leu Glu Ser Ile Tyr Pro Asn Pro Asp Val Phe Asn Pro Asp
465                 470                 475                 480

Asn Phe Leu Pro Glu Lys Gln Ala Asn Arg His Tyr Tyr Ala Phe Val
                485                 490                 495

Pro Phe Ser Ala Gly Pro Arg Ser Cys Val Gly Arg Lys Tyr Ala Met
                500                 505                 510

Leu Lys Leu Lys Ile Ile Leu Ser Thr Ile Leu Arg Asn Phe Arg Val
            515                 520                 525

Tyr Ser Asp Leu Lys Glu Glu Phe Lys Leu Gln Ala Asp Ile Ile
530                 535                 540

Leu Lys Arg Glu Glu Gly Phe Gln Ile Arg Leu Glu Pro Arg Gln Arg
545                 550                 555                 560

Lys Ser Lys Thr Leu
                565

<210> SEQ ID NO 20
<211> LENGTH: 553
<212> TYPE: PRT
<213> ORGANISM: Tribolium castaneum

<400> SEQUENCE: 20

Met Val Val Val Glu Glu Ser Leu Asn His Ser Leu Asn Leu Gly Asn
1               5                   10                  15

Ser Val Leu Ile Ser Leu Gly Val Val Ala Val Ile Leu Ala Val Tyr
            20                  25                  30

His Phe Trp Leu Gln Ser Leu Arg Tyr Thr Lys Leu Gly Asn Lys Ile
            35                  40                  45

Pro Gly Tyr Asp Pro Leu Pro Ile Ile Gly Asn Ala His Met Val Met
        50                  55                  60

Asn Lys Asn Pro Thr Gln Val Met Glu Leu Ala Leu Arg Val Ala Ser
65                  70                  75                  80

Glu Lys Gly Ser Val Val Arg Phe Trp Phe Gly Ser Lys Leu Gly Val
                85                  90                  95

Ala Leu Leu Asp Pro Arg Asp Ile Glu Leu Ile Leu Gly Ser Asn Val
                100                 105                 110

His Leu Glu Lys Ser Ser Glu Tyr Arg Phe Phe Glu Pro Trp Leu Gly
            115                 120                 125

Asp Gly Leu Leu Ile Ser Lys Gly Asp Lys Trp Arg Ser His Arg Lys
        130                 135                 140

Met Ile Ala Pro Thr Phe His Gln Ser Ile Leu Lys Thr Phe Val Pro
145                 150                 155                 160

Val Phe Asn Lys Asn Ala Met Asp Leu Val Glu Gln Leu Arg Asn Glu
                165                 170                 175

Ala Leu Asp Gln Ile Cys Asp Val His Asp Tyr Leu Ser Gly Ala Thr
            180                 185                 190

Val Asp Val Leu Leu Glu Thr Val Met Gly Val Lys Lys Thr Lys Glu
        195                 200                 205

Ala Arg Thr Ser Tyr Lys Tyr Ala Lys Ala Val Met Asp Met Cys Thr
210                 215                 220

Ile Leu His Phe Arg His Val Lys Leu Trp Leu Arg Ser Asp Trp Ile
225                 230                 235                 240

Phe Ser Phe Thr Lys Leu Phe Lys Glu Gln Thr Ser Leu Leu Arg Ile
            245                 250                 255

Ile His Asn Leu Thr Asp Arg Val Ile Lys Gln Lys Lys Lys Ala Tyr
                260                 265                 270

Phe Glu Arg Val Lys Asp Gly Asp Val Ser Leu Tyr Asn Asn Ala Val
            275                 280                 285

Lys Glu Thr Glu Glu Glu Asn Leu Lys Ile Lys Asn Glu Gln Thr Phe
        290                 295                 300

Asn Phe Gly Ser Gly Leu Arg Asp Asp Leu Asp Glu Asn Asp Glu Asn
305                 310                 315                 320

Leu Gly Glu Lys Lys Arg Leu Ala Phe Leu Asp Phe Met Val Glu Ala
                325                 330                 335

Ser Gln Thr Glu Gly Asn Lys Leu Asn Asp Glu Glu Ile Arg Glu Glu
            340                 345                 350

Val Asn Thr Ile Met Phe Glu Gly His Asp Thr Thr Ala Ala Ala Ser
        355                 360                 365

Ser Phe Phe Ile Cys Ile Leu Gly Val Tyr Pro Glu Ile Gln Glu Lys
370                 375                 380

Val Tyr Gln Glu Leu Arg Asp Ile Phe Gln Asp Ser Asp Arg Pro Ile
385                 390                 395                 400

Thr Phe Asn Asp Thr Leu Gln Met Lys Tyr Leu Glu Arg Val Leu Leu
                405                 410                 415

Glu Thr Leu Arg Met Tyr Pro Pro Val Pro Ile Ile Thr Arg Val Ile
            420                 425                 430

Asn Glu Glu Val Lys Leu Ala Ser Gly Asp Tyr Thr Leu Pro Val Gly
            435                 440                 445

Thr Thr Val Gly Ile Gly Gln Phe Leu Val His Arg Asn Pro Lys Tyr
        450                 455                 460

Phe Pro Asn Pro Asp Lys Phe Asp Pro Asp Asn Phe Leu Pro Glu Arg
465                 470                 475                 480

Cys Gln Gln Arg His Tyr Tyr Ser Phe Ile Pro Phe Ser Ala Gly Pro
                485                 490                 495

Arg Ser Cys Val Gly Arg Lys Tyr Ala Met Leu Lys Leu Lys Ile Leu
            500                 505                 510

Leu Ala Ser Ile Val Arg Asn Phe Lys Ile Lys Ser Val Val Lys Glu
        515                 520                 525

Lys Asp Phe Gln Leu Gln Ala Asp Ile Ile Leu Lys Arg Ala Asp Gly
    530                 535                 540

Phe Arg Val Ile Leu Thr Ser Arg Thr
545                 550

<210> SEQ ID NO 21
<211> LENGTH: 560
<212> TYPE: PRT
<213> ORGANISM: Tribolium castaneum

<400> SEQUENCE: 21

Met Ser Thr Thr Val Pro Thr Pro Asp Ile Ser Thr Pro Ser Gly Ile
1               5                   10                  15

Leu Ser Ala Ser Asn Val Phe Tyr Phe Leu Leu Ile Pro Ala Leu Leu
            20                  25                  30

Leu Trp Tyr Ala Tyr Trp Arg Ile Ser Lys Arg His Met Leu Glu Leu
        35                  40                  45

```
Ala Ala Lys Ile Pro Gly Pro Pro Gly Leu Pro Ile Leu Gly Asn Ala
     50                  55                  60

Leu Asp Leu Val Gly Lys Pro His Gln Val Phe Ser His Val Tyr Gln
 65                  70                  75                  80

Lys Ser Phe Glu Tyr Lys Lys Val Val Lys Met Trp Ala Gly Pro Lys
                 85                  90                  95

Leu Leu Val Phe Leu Thr Asp Pro Ser Asp Ile Glu Leu Ile Leu Ser
                100                 105                 110

Ser Tyr Val His Ile Asp Lys Ser Ser Glu Tyr Arg Phe Phe Lys Pro
                115                 120                 125

Trp Leu Gly Asp Gly Leu Leu Ile Ser Thr Gly Gln Lys Trp Lys Ala
    130                 135                 140

His Arg Lys Leu Ile Ala Pro Thr Phe His Leu Asn Val Leu Lys Ser
145                 150                 155                 160

Phe Ile Asp Leu Phe Asn Ala Asn Ser Arg Asp Val Ile Arg Lys Leu
                165                 170                 175

Gln Lys Glu Ile Gly Lys Glu Phe Asp Cys His Asp Tyr Met Ser Glu
                180                 185                 190

Ala Thr Val Glu Met Leu Leu Glu Thr Ala Met Gly Val Ser Lys Lys
            195                 200                 205

Thr Gln Asp Gln Ser Gly Tyr Asp Tyr Ala Met Ala Val Met Lys Met
210                 215                 220

Cys Asp Ile Leu His Leu Arg His Thr Lys Phe Trp Leu Arg Pro Asp
225                 230                 235                 240

Ile Ile Phe Asn Gln Thr Lys Tyr Ala Glu Tyr Gln Lys Ser Leu Ile
                245                 250                 255

Asn Thr Ile His Ser Leu Thr Arg Lys Val Ile Lys Arg Lys Arg Ala
                260                 265                 270

Asp Phe Asp Lys Gly Ile Arg Gly Ser Thr Ala Glu Val Pro Pro Glu
                275                 280                 285

Leu Gln Thr Lys Asn Tyr Asp Lys Thr Glu Ser Lys Thr Val Val Glu
        290                 295                 300

Gly Leu Ser Tyr Gly Gln Ser Ala Gly Leu Lys Asp Asp Leu Asp Val
305                 310                 315                 320

Asp Asp Asn Asp Ile Gly Glu Lys Lys Arg Met Ala Phe Leu Asp Leu
                325                 330                 335

Met Ile Glu Ala Ser Gln Asn Gly Val Val Ile Asn Asp Glu Glu Ile
            340                 345                 350

Lys Glu Gln Val Asp Thr Ile Met Phe Glu Gly His Asp Thr Thr Ala
        355                 360                 365

Ala Gly Ser Ser Phe Phe Leu Ser Met Met Gly Val His Gln Asp Ile
    370                 375                 380

Gln Asp Lys Val Val Gln Glu Leu Tyr Asp Ile Phe Gly Asp Ser Asp
385                 390                 395                 400

Arg Pro Ala Thr Phe Ala Asp Thr Leu Glu Met Lys Tyr Leu Glu Arg
                405                 410                 415

Cys Leu Met Glu Thr Leu Arg Met Phe Pro Pro Val Pro Ile Ile Ala
            420                 425                 430

Arg Gln Leu Asn Gln Asp Leu Lys Leu Ala Ser Gly Asp Tyr Thr Val
        435                 440                 445

Pro Ala Gly Cys Thr Val Val Ile Gly Thr Phe Lys Val His Arg Leu
450                 455                 460

Glu Glu Tyr Tyr Pro Asn Pro Asp Lys Phe Asp Pro Asp Asn Phe Leu
```

```
                465                 470                 475                 480
Pro Glu Arg Thr Ala Asn Arg His Tyr Tyr Ser Phe Ile Pro Phe Ser
                    485                 490                 495

Ala Gly Pro Arg Ser Cys Val Gly Arg Lys Tyr Ala Met Leu Lys Leu
                500                 505                 510

Lys Ile Leu Leu Ser Thr Ile Leu Arg Asn Tyr Arg Ile Tyr Ser Asp
                515                 520                 525

Leu Lys Glu Lys Asp Phe Gln Leu Gln Gly Asp Ile Ile Leu Lys Arg
            530                 535                 540

Ala Glu Gly Phe Lys Val Arg Leu Glu Pro Arg Lys Met Ala Lys Ala
545                 550                 555                 560

<210> SEQ ID NO 22
<211> LENGTH: 562
<212> TYPE: PRT
<213> ORGANISM: Bombyx mori

<400> SEQUENCE: 22

Met Thr Ser Leu Val Asp Glu Thr Glu Gly Tyr His Val Asn Ser Arg
1               5                   10                  15

Val Ile Phe Tyr Pro Leu Leu Gly Leu Thr Thr Ala Ile Trp Ile Leu
                20                  25                  30

Tyr Arg Trp Gln Gln Asn Ser His Met His Lys Leu Ala Glu Leu Ile
            35                  40                  45

Pro Gly Pro Ala Pro Ile Pro Ile Phe Gly Asn Ala Leu Thr Leu Met
        50                  55                  60

Arg Lys Asp Pro His Glu Leu Val Asn Leu Ala Leu Gly Tyr Ala Gln
65                  70                  75                  80

Thr Phe Gly Asn Val Val Arg Val Trp Leu Gly Ser Lys Leu Ile Val
                85                  90                  95

Phe Leu Ala Asp Ala Asp Asp Ile Glu Ile Ile Leu Asn Ser His Val
                100                 105                 110

His Ile Asp Lys Ala Thr Glu Tyr Lys Phe Phe Lys Pro Trp Leu Gly
            115                 120                 125

Glu Gly Leu Leu Ile Ser Ser Gly Pro Lys Trp Arg Ser His Arg Lys
        130                 135                 140

Met Ile Ala Pro Thr Phe His Ile Asn Ile Leu Lys Ser Phe Val Gly
145                 150                 155                 160

Ile Phe Asn Gln Asn Ser Asn Asn Val Val Glu Lys Leu Lys Ser Glu
                165                 170                 175

Val Gly Lys Thr Phe Asp Val His Asp Tyr Met Ser Gly Thr Thr Val
                180                 185                 190

Asp Ile Leu Leu Glu Thr Ala Met Gly Ile Ser Arg Lys Thr Gln Asp
            195                 200                 205

Glu Ser Gly Phe Asp Tyr Ala Met Ala Val Met Lys Met Cys Asp Ile
        210                 215                 220

Ile His Gln Arg His Tyr Lys Phe Trp Met Arg Ser Glu Ile Val Phe
225                 230                 235                 240

Lys Leu Thr Ser Phe Phe Lys Gln Gln Thr Lys Leu Trp Gly Ile Ile
                245                 250                 255

His Gly Leu Thr Asn Lys Val Ile Lys Asn Lys Lys Glu Thr Tyr Leu
                260                 265                 270

Glu Asn Lys Ala Lys Gly Ile Ile Pro Pro Thr Leu Glu Glu Trp Thr
            275                 280                 285

His His Ser Gly Glu Ile Leu Ala Asn Asn Ala Lys Thr Leu Ser Asp
```

```
                290                 295                 300
Thr Val Phe Lys Gly Tyr Arg Asp Asp Leu Asp Phe Asn Asp Glu Asn
305                 310                 315                 320

Asp Val Gly Glu Lys Lys Arg Arg Ala Phe Trp Asp Leu Met Ile Glu
                325                 330                 335

Ser Ser Gln Asn Gly Thr Asn Lys Ile Ser Asp His Glu Ile Lys Glu
                340                 345                 350

Glu Val Asp Thr Ile Met Phe Glu Gly His Asp Thr Thr Ala Ala Gly
                355                 360                 365

Ser Ser Phe Val Leu Cys Leu Leu Gly Ile His Gln Asp Val Gln Ala
                370                 375                 380

Arg Val Tyr Asp Glu Leu Tyr Gln Ile Leu Gly Asp Ser Asp Arg Pro
385                 390                 395                 400

Ala Thr Phe Ala Asp Thr Leu Glu Met Lys Tyr Leu Glu Arg Val Ile
                        405                 410                 415

Leu Glu Ser Leu Arg Leu Tyr Pro Pro Val Pro Val Ile Ala Arg Lys
                420                 425                 430

Leu Asn Arg Asp Val Thr Ile Ser Thr Lys Asn Tyr Val Ile Pro Ala
                435                 440                 445

Gly Thr Thr Val Val Ile Gly Thr Phe Met Leu His Arg Gln Pro Lys
450                 455                 460

Tyr His Lys Asp Pro Glu Val Phe Asn Pro Asp Asn Phe Leu Pro Glu
465                 470                 475                 480

Asn Thr Gln Asn Arg His Tyr Tyr Ser Tyr Ile Pro Phe Ser Ala Gly
                        485                 490                 495

Pro Arg Ser Cys Val Gly Arg Lys Tyr Ala Leu Leu Lys Leu Lys Ile
                500                 505                 510

Leu Leu Ser Thr Ile Leu Arg Asn Phe Arg Thr Ile Ser Glu Ile Pro
                515                 520                 525

Glu Lys Glu Phe Lys Leu Gln Gly Asp Ile Ile Leu Lys Arg Ala Glu
                530                 535                 540

Gly Phe Gln Met Lys Val Glu Pro Arg Lys Arg Val Pro Thr Asn Val
545                 550                 555                 560

Ala Arg

<210> SEQ ID NO 23
<211> LENGTH: 556
<212> TYPE: PRT
<213> ORGANISM: Bombyx mori

<400> SEQUENCE: 23

Met Ser Tyr Thr Asn Ala Glu Asn Val Val Pro Thr Ser Thr Phe Ser
1               5                   10                  15

Ala Ile Asn Leu Phe Tyr Val Leu Leu Val Pro Ala Val Ile Leu Trp
                20                  25                  30

Tyr Ala Tyr Trp Arg Met Ser Arg Arg Arg Leu Tyr Glu Leu Ala Asp
                35                  40                  45

Lys Leu Asn Gly Pro Pro Gly Leu Pro Leu Leu Gly Asn Ala Leu Glu
50                  55                  60

Phe Val Gly Gly Ser Ala Asp Ile Phe Arg Asn Ile Val Gln Lys Ser
65                  70                  75                  80

Ala Asp Tyr Asp His Glu Ser Val Val Lys Ile Trp Ile Gly Pro Arg
                85                  90                  95

Leu Leu Val Phe Leu Tyr Asp Pro Arg Asp Val Glu Val Ile Leu Ser
                100                 105                 110
```

```
Ser His Val Tyr Ile Asp Lys Ala Glu Glu Tyr Arg Phe Phe Lys Pro
        115                 120                 125

Trp Leu Gly Asn Gly Leu Leu Ile Ser Thr Gly Gln Lys Trp Arg Ser
130                 135                 140

His Arg Lys Leu Ile Ala Pro Thr Phe His Leu Asn Val Leu Lys Ser
145                 150                 155                 160

Phe Ile Asp Leu Phe Asn Ala Asn Ser Arg Ala Val Val Asp Lys Leu
                165                 170                 175

Lys Lys Glu Ala Ser Asn Phe Asp Cys His Asp Tyr Met Ser Glu Cys
            180                 185                 190

Thr Val Glu Ile Leu Leu Glu Thr Ala Met Gly Val Ser Lys Ser Thr
        195                 200                 205

Gln Asp Gln Ser Gly Phe Glu Tyr Ala Met Ala Val Met Lys Met Cys
    210                 215                 220

Asp Ile Leu His Leu Arg His Thr Lys Ile Trp Leu Arg Pro Asp Leu
225                 230                 235                 240

Leu Phe Lys Phe Thr Asp Tyr Ala Lys Asn Gln Thr Lys Leu Leu Asp
                245                 250                 255

Ile Ile His Gly Leu Thr Lys Lys Val Ile Lys Arg Lys Lys Glu Glu
            260                 265                 270

Phe Ala Ser Gly Lys Lys Pro Ser Asn Leu Asn Glu Thr Ala Thr Thr
        275                 280                 285

Ser Glu Pro Ser Thr Gly Lys Leu Thr Ser Val Glu Gly Leu Ser Phe
    290                 295                 300

Gly Gln Ser Ser Gly Leu Lys Asp Asp Leu Asp Val Asp Asp Asp Val
305                 310                 315                 320

Gly Gln Lys Lys Arg Leu Ala Phe Leu Asp Leu Leu Glu Ser Ser
                325                 330                 335

Gln Ser Gly Val Ala Ile Ser Asp Glu Glu Ile Lys Glu Gln Val Asp
            340                 345                 350

Thr Ile Met Phe Glu Gly His Asp Thr Thr Ala Ala Gly Ser Ser Phe
        355                 360                 365

Phe Leu Ser Met Met Gly Ile His Gln Asp Ile Gln Asp Lys Val Ile
    370                 375                 380

Glu Glu Leu Asp Gln Ile Phe Gly Asp Ser Asp Arg Pro Val Thr Phe
385                 390                 395                 400

Gln Asp Thr Leu Glu Met Lys Tyr Leu Glu Arg Cys Leu Met Glu Thr
                405                 410                 415

Leu Arg Leu Tyr Pro Pro Val Pro Ile Ile Ala Arg Gln Val Asn Gln
            420                 425                 430

Glu Ile Thr Leu Pro Ser Asn Gly Lys Lys Ile Pro Ala Gly Thr Thr
        435                 440                 445

Leu Val Ile Ala Thr Tyr Lys Leu His Arg Arg Pro Asp Val Tyr Pro
    450                 455                 460

Asn Pro Asn Lys Phe Asp Pro Asp Asn Phe Leu Pro Glu Arg Ser Ala
465                 470                 475                 480

Asn Arg His Tyr Tyr Ala Phe Val Pro Phe Ser Ala Gly Pro Arg Ser
                485                 490                 495

Cys Val Gly Arg Lys Tyr Ala Met Leu Lys Leu Lys Val Ile Leu Ser
            500                 505                 510

Thr Ile Leu Arg Asn Phe Arg Val Ile Ser Val Leu Lys Glu Ser Asp
        515                 520                 525

Phe Lys Leu Gln Ala Asp Ile Ile Leu Lys Arg Ala Glu Gly Phe Gln
```

```
                    530                 535                 540
Val Arg Leu Gln Pro Arg Lys Arg Met Ala Lys Ala
545                 550                 555

<210> SEQ ID NO 24
<211> LENGTH: 561
<212> TYPE: PRT
<213> ORGANISM: Leptinotarsa decemlineata

<400> SEQUENCE: 24

Met Ser Ala Ala Thr Ala Ser Val Asp Leu Glu Asn Pro Thr Thr Leu
1               5                   10                  15

Leu Thr Pro Lys Asn Ile Phe Tyr Phe Leu Leu Ile Pro Ala Leu Val
                20                  25                  30

Leu Trp Tyr Ala Tyr Trp Lys Ile Ser Arg Arg His Met Val Glu Leu
            35                  40                  45

Ala Ser Lys Ile Pro Gly Pro Glu Gly Leu Pro Leu Leu Gly Ser Ala
        50                  55                  60

Leu Glu Phe Val Gly Thr Ser Ala Asp Ile Phe Lys Arg Met Tyr Ala
65                  70                  75                  80

Lys Ser Phe Glu Tyr Gly Asn Thr Val Lys Val Trp Ile Gly Pro Lys
                85                  90                  95

Leu Leu Ile Phe Leu Val Asp Pro Arg Asp Val Glu Ile Ile Leu Ser
            100                 105                 110

Ser His Val His Ile Asp Lys Ala Ser Glu Tyr Arg Phe Phe Gln Pro
        115                 120                 125

Trp Leu Gly Asp Gly Leu Leu Ile Ser Thr Gly Gln Lys Trp Arg Ala
    130                 135                 140

His Arg Lys Leu Ile Ala Pro Thr Phe His Leu Asn Val Leu Lys Ser
145                 150                 155                 160

Phe Ile Asp Leu Phe Asn Ala Asn Ser Arg Glu Val Val Gln Lys Leu
                165                 170                 175

Lys Lys Glu Val Gly Lys Glu Phe Asp Cys His Asp Tyr Met Ser Glu
            180                 185                 190

Ala Thr Val Glu Ile Leu Leu Glu Thr Ala Met Gly Val Ser Lys Lys
        195                 200                 205

Thr Gln Asp Gln Ser Gly Tyr Asp Tyr Ala Met Ala Val Met Lys Met
    210                 215                 220

Cys Asp Ile Leu His Leu Arg His Thr Lys Val Trp Leu Arg Pro Asp
225                 230                 235                 240

Phe Ile Phe Asn Leu Thr Asn Tyr Ala Lys Lys Gln Glu Gly Leu Ile
                245                 250                 255

Gly Ile Ile His Ser Leu Thr Arg Lys Val Ile Arg Lys Arg Ala
            260                 265                 270

Asp Phe Glu Lys Gly Ile Arg Gly Ser Thr Ala Glu Val Pro Glu Glu
        275                 280                 285

Leu Lys Thr Lys Asn Phe Asp Lys Asn Val Ser Ser Lys Thr Val Val
    290                 295                 300

Glu Gly Leu Ser Tyr Gly Gln Ala Ala Gly Leu Lys Asp Asp Leu Asp
305                 310                 315                 320

Val Asp Asp Val Gly Glu Lys Lys Arg Met Ala Phe Leu Asp Leu
                325                 330                 335

Met Ile Glu Ala Ser Gln Asn Gly Val Val Ile Asn Asp Glu Ile
            340                 345                 350

Lys Glu Gln Val Asp Thr Ile Met Phe Glu Gly His Asp Thr Thr Ala
```

```
                    355                 360                 365
Ala Gly Ser Ser Phe Phe Leu Ser Met Met Gly Val His Gln Asp Ile
370                 375                 380

Gln Asp Lys Val Val Gln Glu Ile Asp Glu Ile Phe Gly Asp Ser Asp
385                 390                 395                 400

Arg Pro Ala Thr Phe Ala Asp Thr Leu Glu Met Lys Tyr Leu Glu Arg
                405                 410                 415

Cys Leu Met Glu Thr Leu Arg Met Tyr Pro Pro Val Pro Ile Ile Ala
                420                 425                 430

Arg Gln Leu Arg Gln Asp Val Lys Leu Ala Ser Gly Asp Tyr Thr Leu
            435                 440                 445

Pro Ala Gly Ala Thr Ile Val Ile Gly Thr Phe Lys Ile His Arg Gln
            450                 455                 460

Glu Asp Val Tyr Pro Asn Pro Asp Lys Phe Asp Pro Asn Phe Leu
465                 470                 475                 480

Pro Glu Arg Ser Ala Asn Arg His Tyr Tyr Ser Phe Ile Pro Phe Ser
                485                 490                 495

Ala Gly Pro Arg Ser Cys Val Gly Arg Lys Tyr Ala Met Leu Lys Leu
                500                 505                 510

Lys Ile Leu Leu Ser Thr Ile Leu Arg Asn Tyr Arg Ile Tyr Ser Thr
            515                 520                 525

Val Glu Glu Lys Asp Phe Gln Leu Gln Gly Asp Ile Ile Leu Lys Arg
            530                 535                 540

Ala Asp Gly Phe Arg Ile Lys Leu Glu Pro Arg Lys Arg Val Leu Lys
545                 550                 555                 560

Ala

<210> SEQ ID NO 25
<211> LENGTH: 577
<212> TYPE: PRT
<213> ORGANISM: Drosophila sechellia

<400> SEQUENCE: 25

Met Glu Val Leu Lys Lys Asp Ala Ala Leu Gly Ser Pro Ser Asn Val
1               5                   10                  15

Phe Tyr Phe Leu Leu Pro Thr Leu Val Leu Trp Tyr Ile Tyr Trp
            20                  25                  30

Arg Leu Ser Arg Ala His Leu Tyr Arg Leu Ala Gly Arg Leu Pro Gly
            35                  40                  45

Pro Arg Gly Leu Pro Ile Val Gly His Leu Phe Asp Val Ile Gly Pro
50                  55                  60

Ala Ser Ser Val Phe Arg Thr Val Ile Arg Lys Ser Ala Pro Phe Glu
65                  70                  75                  80

His Ile Ala Lys Met Trp Ile Gly Pro Lys Leu Val Val Phe Ile Tyr
                85                  90                  95

Asp Pro Arg Asp Val Glu Leu Leu Ser Ser His Val Tyr Ile Asp
            100                 105                 110

Lys Ala Ser Glu Tyr Lys Phe Phe Lys Pro Trp Leu Gly Asp Gly Leu
        115                 120                 125

Leu Ile Ser Thr Gly Gln Lys Trp Arg Ser His Arg Lys Leu Ile Ala
130                 135                 140

Pro Thr Phe His Leu Asn Val Leu Lys Ser Phe Ile Glu Leu Phe Asn
145                 150                 155                 160

Glu Asn Ser Arg Asn Val Val Arg Lys Leu Arg Ala Glu Asp Gly Arg
                165                 170                 175
```

```
Thr Phe Asp Cys His Asp Tyr Met Ser Glu Ala Thr Val Glu Ile Leu
            180                 185                 190

Leu Glu Thr Ala Met Gly Val Ser Lys Lys Thr Gln Asp Lys Ser Gly
        195                 200                 205

Phe Glu Tyr Ala Met Ala Val Met Arg Met Cys Asp Ile Leu His Ala
    210                 215                 220

Arg His Arg Ser Ile Phe Leu Arg Asn Glu Phe Val Phe Thr Leu Thr
225                 230                 235                 240

Arg Tyr Tyr Lys Glu Gln Gly Arg Leu Leu Asn Ile Ile His Gly Leu
                245                 250                 255

Thr Thr Lys Val Ile Arg Ser Lys Lys Ala Ala Phe Glu Gln Gly Thr
            260                 265                 270

Arg Gly Ser Leu Ala Gln Cys Glu Leu Lys Ala Ala Ala Leu Glu Arg
        275                 280                 285

Glu Arg Glu Gln Asp Gly Gly Val Gly Gly Gly Asp Gln Thr Ala Ser
    290                 295                 300

Thr Ala Gly Ser Glu Glu Lys Asp Arg Glu Lys Asp Lys Glu Lys Ala
305                 310                 315                 320

Ser Pro Val Ala Gly Leu Ser Tyr Gly Gln Ser Ala Gly Leu Lys Asp
                325                 330                 335

Asp Leu Asp Val Glu Asp Asn Asp Ile Gly Glu Lys Lys Arg Leu Ala
            340                 345                 350

Phe Leu Asp Leu Met Leu Glu Ser Ala Gln Asn Gly Ala Leu Ile Thr
        355                 360                 365

Asp Thr Glu Ile Lys Glu Gln Val Asp Thr Ile Met Phe Glu Gly His
    370                 375                 380

Asp Thr Thr Ala Ala Gly Ser Ser Phe Phe Leu Ser Leu Met Gly Ile
385                 390                 395                 400

His Gln Asp Ile Gln Asp Arg Val Leu Ala Glu Leu Asp Ser Ile Phe
                405                 410                 415

Gly Asp Ser Gln Arg Pro Ala Thr Phe Gln Asp Thr Leu Glu Met Lys
            420                 425                 430

Tyr Leu Glu Arg Cys Leu Met Glu Thr Leu Arg Met Tyr Pro Pro Val
        435                 440                 445

Pro Leu Ile Ala Arg Glu Leu Gln Glu Asp Leu Lys Leu Asn Ser Gly
    450                 455                 460

Asn Tyr Val Ile Pro Arg Gly Ala Thr Val Thr Val Ala Thr Val Leu
465                 470                 475                 480

Leu His Arg Asn Pro Lys Val Tyr Ala Asn Pro Asn Val Phe Asp Pro
                485                 490                 495

Asp Asn Phe Leu Pro Glu Arg Gln Ala Asn Arg His Tyr Tyr Ala Phe
            500                 505                 510

Val Pro Phe Ser Ala Gly Pro Arg Ser Cys Val Gly Arg Lys Tyr Ala
        515                 520                 525

Met Leu Lys Leu Lys Ile Leu Leu Ser Thr Ile Leu Arg Asn Tyr Arg
530                 535                 540

Val Tyr Ser Asp Leu Thr Glu Ser Asp Phe Lys Leu Gln Ala Asp Ile
545                 550                 555                 560

Ile Leu Lys Arg Glu Glu Gly Phe Arg Val Arg Leu Gln Pro Arg Thr
                565                 570                 575

Arg

<210> SEQ ID NO 26
```

```
<211> LENGTH: 548
<212> TYPE: PRT
<213> ORGANISM: Apis mellifera

<400> SEQUENCE: 26
```

| | | | | | | | | | | | | | | | |
|---|---|---|---|---|---|---|---|---|---|---|---|---|---|---|---|
| Met | Ala | Ala | Ser | Ala | Thr | Gly | Phe | Ser | Ala | Ser | Val | Phe | Leu | | |
| 1 | | | | 5 | | | | | 10 | | | | | 15 | |
| Ser | Leu | Leu | Ile | Pro | Ala | Leu | Ile | Leu | Tyr | Phe | Ile | Tyr | Phe | Arg | Ile |
| | | | 20 | | | | | 25 | | | | | 30 | | |
| Ser | Arg | Arg | His | Leu | Leu | Glu | Leu | Ala | Glu | Lys | Ile | Pro | Gly | Pro | Pro |
| | | 35 | | | | | 40 | | | | | 45 | | | |
| Ala | Leu | Pro | Leu | Ile | Gly | Asn | Ala | Leu | Asp | Leu | Phe | Gly | Ser | Pro | Asp |
| | 50 | | | | | 55 | | | | | 60 | | | | |
| Ala | Met | Phe | Ser | Gln | Val | Leu | Lys | Lys | Ala | Glu | Asn | Phe | Lys | Asp | Val |
| 65 | | | | | 70 | | | | | 75 | | | | | 80 |
| Val | Lys | Ile | Trp | Val | Gly | Pro | Lys | Leu | Val | Ile | Cys | Leu | Ile | Asp | Pro |
| | | | | 85 | | | | | 90 | | | | | 95 | |
| Arg | Asp | Val | Glu | Ile | Ile | Leu | Ser | Ser | Asn | Val | Tyr | Ile | Asp | Lys | Ser |
| | | | 100 | | | | | 105 | | | | | 110 | | |
| Thr | Glu | Tyr | Arg | Phe | Phe | Lys | Pro | Trp | Leu | Gly | Asp | Gly | Leu | Leu | Ile |
| | | | 115 | | | | | 120 | | | | | 125 | | |
| Ser | Thr | Gly | Gln | Lys | Trp | Arg | Asn | His | Arg | Lys | Leu | Ile | Ala | Pro | Thr |
| | 130 | | | | | 135 | | | | | 140 | | | | |
| Phe | His | Leu | Asn | Val | Leu | Lys | Ser | Phe | Ile | Asp | Leu | Phe | Asn | Ala | Asn |
| 145 | | | | | 150 | | | | | 155 | | | | | 160 |
| Ala | Arg | Ser | Val | Val | Glu | Lys | Met | Arg | Lys | Glu | Asn | Gly | Lys | Glu | Phe |
| | | | | 165 | | | | | 170 | | | | | 175 | |
| Asp | Cys | His | Asn | Tyr | Met | Ser | Glu | Leu | Thr | Val | Asp | Ile | Leu | Leu | Glu |
| | | | 180 | | | | | 185 | | | | | 190 | | |
| Thr | Ala | Met | Gly | Val | Ser | Lys | Pro | Thr | Arg | Asp | His | Asn | Ala | Phe | Glu |
| | | 195 | | | | | 200 | | | | | 205 | | | |
| Tyr | Ala | Met | Ala | Val | Met | Lys | Met | Cys | Asp | Ile | Leu | His | Leu | Arg | His |
| | 210 | | | | | 215 | | | | | 220 | | | | |
| Thr | Lys | Ile | Trp | Leu | Arg | Pro | Asp | Trp | Leu | Phe | Asn | Leu | Thr | Lys | Tyr |
| 225 | | | | | 230 | | | | | 235 | | | | | 240 |
| Gly | Lys | Asn | Gln | Ile | Lys | Leu | Leu | Glu | Ile | Ile | His | Gly | Leu | Thr | Lys |
| | | | | 245 | | | | | 250 | | | | | 255 | |
| Lys | Val | Ile | Gln | Leu | Lys | Lys | Glu | Glu | Tyr | Lys | Ser | Gly | Lys | Arg | Asn |
| | | | 260 | | | | | 265 | | | | | 270 | | |
| Ile | Ile | Asp | Asn | Ser | Ala | Gln | Lys | Thr | Glu | Ser | Lys | Thr | Asn | Asn | Ile |
| | | | | 275 | | | | | 280 | | | | | 285 | |
| Val | Val | Glu | Gly | Val | Ser | Phe | Gly | Gln | Ser | Val | Gly | Leu | Lys | Asp | Asp |
| | 290 | | | | | 295 | | | | | 300 | | | | |
| Leu | Asp | Ile | Asp | Asp | Val | Gly | Glu | Lys | Lys | Arg | Gln | Ala | Phe | Leu |
| 305 | | | | | 310 | | | | | 315 | | | | | 320 |
| Asp | Leu | Leu | Ile | Glu | Ala | Gly | Gln | Asn | Gly | Val | Leu | Leu | Thr | Asp | Lys |
| | | | | 325 | | | | | 330 | | | | | 335 | |
| Glu | Val | Lys | Glu | Gln | Val | Asp | Thr | Ile | Met | Phe | Glu | Gly | His | Asp | Thr |
| | | | 340 | | | | | 345 | | | | | 350 | | |
| Thr | Ala | Ser | Gly | Ser | Ser | Phe | Phe | Leu | Ala | Val | Met | Gly | Cys | His | Pro |
| | | 355 | | | | | 360 | | | | | 365 | | | |
| Asp | Ile | Gln | Glu | Lys | Val | Ile | Gln | Glu | Leu | Asp | Glu | Ile | Phe | Gly | Asp |
| | 370 | | | | | 375 | | | | | 380 | | | | |
| Ser | Asp | Arg | Pro | Ala | Thr | Phe | Gln | Asp | Thr | Leu | Glu | Met | Lys | Tyr | Leu |
| 385 | | | | | 390 | | | | | 395 | | | | | 400 |

```
Glu Arg Cys Leu Leu Glu Thr Leu Arg Met Tyr Pro Pro Val Pro Leu
                405                 410                 415

Ile Ala Arg Glu Ile Lys Thr Asp Leu Lys Leu Ala Ser Gly Asp Tyr
            420                 425                 430

Thr Ile Pro Ala Gly Cys Thr Val Val Ile Gly Thr Phe Lys Leu His
        435                 440                 445

Arg Gln Pro His Ile Tyr Pro Asn Pro Asp Val Phe Asp Pro Asp Asn
    450                 455                 460

Phe Leu Pro Glu Lys Thr Ala Asn Arg His Tyr Tyr Ala Phe Val Pro
465                 470                 475                 480

Phe Ser Ala Gly Pro Arg Ser Cys Val Gly Arg Lys Tyr Ala Met Leu
                485                 490                 495

Lys Leu Lys Ile Val Leu Ser Thr Ile Leu Arg Asn Phe Arg Val Arg
            500                 505                 510

Ser Asp Val Lys Glu Ser Glu Phe Arg Leu Gln Ala Asp Ile Ile Leu
        515                 520                 525

Lys Arg Ala Asp Gly Phe Lys Ile Arg Leu Glu Pro Arg Lys Gln Val
    530                 535                 540

Ala Ser Thr Ala
545

<210> SEQ ID NO 27
<211> LENGTH: 546
<212> TYPE: PRT
<213> ORGANISM: Blattella germanica

<400> SEQUENCE: 27

Met Ser Val Thr Val Glu Thr Ala Thr Val Glu Ser Pro Ala Ser Ser
1               5                   10                  15

Ile Ser Thr Phe Met Val Leu Leu Val Ser Ala Val Ala Leu Phe Phe
            20                  25                  30

Ala Tyr Trp Lys Ile Ser Arg Arg Arg Phe Leu Gln Leu Ala Glu Lys
        35                  40                  45

Ile Pro Gly Pro Lys Gly Tyr Pro Ile Ile Gly Asn Ala Leu Asp Phe
    50                  55                  60

Leu Gly Ser Ser Ser Gln Val Thr Asp Arg Met Ile Gln Ile Gly Phe
65                  70                  75                  80

Gln Phe Thr Thr Ile Ala Lys Val Trp Ile Leu His Lys Leu Val Val
                85                  90                  95

Phe Ile Ala Asp Pro Arg Asp Ile Glu Leu Ile Leu Gly Asn Ser Thr
            100                 105                 110

His Leu Glu Lys Ser Glu Glu Tyr Arg Phe Phe Lys Pro Trp Leu Gly
        115                 120                 125

Asp Gly Leu Leu Ile Ser Ser Gly Gln Lys Trp Lys Ser His Arg Lys
    130                 135                 140

Leu Ile Ala Pro Thr Phe His Leu Asn Val Leu Lys Ser Phe Val Asp
145                 150                 155                 160

Leu Phe Asn Ala Asn Ser Arg Ala Val Cys Asp Lys Met Ala Lys Glu
                165                 170                 175

Asn Gly Arg Thr Phe Asp Cys His Asp Tyr Met Ser Glu Cys Thr Val
            180                 185                 190

Glu Val Leu Leu Glu Thr Ala Met Gly Val Ser Lys Lys Thr Gln Asn
        195                 200                 205

Lys Ser Gly Phe Glu Tyr Ala Met Ala Val Met Lys Met Cys Asn Ile
    210                 215                 220
```

Leu His Leu Arg His Ser Lys Val Trp Leu Arg Pro Asp Trp Leu Phe
225                 230                 235                 240

Asn Leu Thr Lys Tyr Gly Lys Glu Gln Val Asp Leu Leu Asp Val Ile
            245                 250                 255

His Gly Leu Thr Lys Lys Val Ile Lys Asn Lys Lys Glu Ile Ile Ser
        260                 265                 270

Ser Gly Thr Lys Lys Tyr Ile Glu Glu Ser Val Thr Gln Glu Glu Lys
    275                 280                 285

Ala Ile Ala Ser Thr Pro Val Lys Gly Leu Arg Asp Asp Leu Asp Glu
290                 295                 300

Gln Asp Glu Asn Asp Val Gly Gln Lys Lys Arg Leu Ala Phe Leu Asp
305                 310                 315                 320

Leu Met Ile Glu Ser Ala Gln Asn Gly Val Val Leu Thr Asp Glu Glu
            325                 330                 335

Ile Lys Glu Glu Val Gly Thr Ile Met Phe Glu Gly His Asp Thr Thr
        340                 345                 350

Ala Ala Gly Ser Ser Phe Phe Leu Cys Leu Met Gly Ile His Gln Lys
    355                 360                 365

Tyr Gln Asp Met Cys Val Gln Glu Leu Asn Gln Ile Phe Gly Asp Ser
370                 375                 380

Asp Arg Pro Ala Thr Phe Ala Asp Thr Leu Glu Met Lys Phe Leu Glu
385                 390                 395                 400

Arg Cys Leu Leu Glu Ala Leu Arg Met Tyr Pro Pro Val Pro Val Ile
            405                 410                 415

Ala Arg Lys Leu Ala Glu Asp Leu Thr Leu Ala Ser Thr Gly Val Val
        420                 425                 430

Ile Pro Gln Gly Thr Thr Ile Val Val Ser Thr Val Lys Thr His Arg
    435                 440                 445

Leu Glu Glu His Trp Pro Asn Pro Asp Val Tyr Asp Pro Asp Asn His
450                 455                 460

Leu Pro Glu Lys Ala Ala Glu Arg His Tyr Tyr Ser Phe Val Pro Phe
465                 470                 475                 480

Ser Ala Gly Pro Arg Ser Cys Val Gly Arg Lys Tyr Ala Leu Leu Lys
            485                 490                 495

Leu Lys Ile Ile Leu Ser Thr Ile Leu Arg Asn Phe Lys Val His Ser
        500                 505                 510

Asp Ile Ser Glu Asp Glu Phe Lys Leu Gln Gly Asp Ile Ile Leu Lys
    515                 520                 525

Arg Ala Asp Gly Phe Met Ile Arg Leu Glu Pro Arg Lys Lys Thr Val
530                 535                 540

Ala Ala
545

<210> SEQ ID NO 28
<211> LENGTH: 564
<212> TYPE: PRT
<213> ORGANISM: Ips paraconfusus

<400> SEQUENCE: 28

Met Ser Thr Ala Thr Leu Ser Ser Ala Ala Pro Gly Leu Leu Thr
1               5                   10                  15

Ser Thr Asn Leu Phe Leu Phe Leu Leu Ala Pro Ala Leu Ala Leu Leu
            20                  25                  30

Tyr Val Tyr Trp Lys Val Ser Arg Lys His Met Val Glu Leu Ala Glu
        35                  40                  45

```
Arg Ile Pro Gly Pro Ser Gly Leu Pro Ile Leu Gly Asn Ala Leu Glu
     50                  55                  60

Phe Ile Gly Thr Pro Asn Gln Ile Phe Asn Thr Ile Tyr Gln Lys Ser
 65                  70                  75                  80

Phe Glu Phe Gly Arg Thr Ile Lys Val Trp Val Gly Pro Arg Leu Leu
                 85                  90                  95

Ile Phe Leu Thr Asp Pro Arg Asp Val Glu Ile Ile Leu Ser Ser His
                100                 105                 110

Val His Ile Asp Lys Ser Pro Glu Tyr Arg Phe Phe Lys Pro Trp Leu
            115                 120                 125

Gly Asp Gly Leu Leu Ile Ser Thr Gly Gln Lys Trp Arg Ala His Arg
            130                 135                 140

Lys Leu Ile Ala Pro Thr Phe His Leu Asn Val Leu Lys Ser Phe Ile
145                 150                 155                 160

Asp Leu Phe Asn Lys Asn Ser Ile Glu Thr Val Asn Lys Leu Glu Lys
                165                 170                 175

Glu Leu Gly Lys Glu Phe Asp Cys His Asp Tyr Met Ser Glu Ala Thr
            180                 185                 190

Val Glu Ile Leu Leu Glu Thr Ala Met Gly Val Ser Lys Lys Thr Gln
            195                 200                 205

Asp Gln Ser Gly Tyr Asp Tyr Ala Met Ala Val Met Lys Leu Cys Asp
210                 215                 220

Ile Leu His Leu Arg His Thr Lys Leu Trp Phe Arg Pro Asp Ile Ile
225                 230                 235                 240

Phe Asn Leu Thr Ser Thr Ala Lys Tyr Gln Glu Lys Leu Ile Asn Val
                245                 250                 255

Ile His Ser Leu Thr Arg Lys Val Ile Gln Lys Lys Ala Asp Phe
            260                 265                 270

Glu Lys Gly Ile Arg Gly Ser Thr Ala Glu Val Pro Glu Glu Leu Lys
            275                 280                 285

Thr Gln Lys Tyr Glu Thr Ala Val Pro Thr Lys Thr Thr Leu Glu
                290                 295                 300

Gly Thr Ser Tyr Gly Gln Ser Val Gly Leu Lys Asp Asp Leu Asp Val
305                 310                 315                 320

Asp Asp Asp Ile Gly Glu Lys Lys Arg Met Ala Phe Leu Asp Leu Met
                325                 330                 335

Ile Glu Ala Ser Gln Asn Gly Val Val Ile Asn Asp Glu Glu Ile Lys
            340                 345                 350

Glu Gln Val Asp Thr Ile Met Phe Glu Gly His Asp Thr Thr Ala Ala
            355                 360                 365

Gly Ser Ser Phe Phe Leu Cys Gln Met Ala Ala His Pro Glu Ile Gln
370                 375                 380

Glu Lys Val Leu Gln Glu Ile Asp Glu Ile Phe Gln Gly Ser Asp Arg
385                 390                 395                 400

Pro Ala Thr Phe Ala Asp Thr Leu Glu Met Lys Tyr Leu Glu Arg Cys
                405                 410                 415

Leu Leu Glu Thr Leu Arg Leu Phe Pro Pro Val Pro Ile Ile Ala Arg
            420                 425                 430

Gln Leu Gln Gln Asp Val Lys Leu Ala Ser Asn Pro Ser Tyr Val Leu
            435                 440                 445

Pro Ser Gly Ala Thr Ile Ile Gly Thr Phe Lys Val His Arg Leu
450                 455                 460

Glu Glu Ile Tyr Gly Pro Asn Ala Asp Lys Phe Asp Pro Asp Asn Phe
```

Leu Pro Glu Arg Ala Ala Asn Arg His Tyr Tyr Ser Phe Ile Pro Phe
465                 470                 475                 480

Ser Ala Gly Pro Arg Ser Cys Val Gly Arg Lys Tyr Ala Met Leu Lys
            485                 490                 495

Leu Lys Ile Leu Leu Ser Thr Ile Leu Arg Asn Tyr Lys Ile Lys Ser
            500                 505                 510

Asn Leu Lys Glu Ser Asp Tyr Lys Leu Gln Gly Asp Ile Ile Leu Lys
    515                 520                 525

Arg Ala Asp Gly Phe Lys Ile Met Leu Glu Lys Arg Lys Pro Ile Val
530                 535                 540

Ser Val Lys Ala
545                 550                 555                 560

<210> SEQ ID NO 29
<211> LENGTH: 557
<212> TYPE: PRT
<213> ORGANISM: Antheraea yamamai

<400> SEQUENCE: 29

Met Ser Tyr Thr Thr Ala Glu Asn Val Val Pro Ser Ser Thr Phe Ser
1               5                   10                  15

Ala Ile Asn Leu Phe Tyr Val Leu Leu Val Pro Ala Ile Ile Leu Trp
            20                  25                  30

Tyr Thr Tyr Trp Arg Met Ser Arg Arg Leu Tyr Glu Leu Ala Glu
        35                  40                  45

Lys Leu Ser Gly Pro Glu Pro Leu Pro Ile Ile Gly Asn Ala Leu Glu
    50                  55                  60

Phe Val Gly Gly Ser Asn Asp Ile Phe Asn Asn Ile Ile Ala Lys Ser
65                  70                  75                  80

Leu Pro Phe Asp Asp Glu Ala Val Val Arg Leu Trp Ile Gly Pro Arg
                85                  90                  95

Leu Leu Val Phe Ile Tyr Asp Pro Arg Asp Val Glu Val Ile Leu Ser
            100                 105                 110

Ser His Val His Ile Asp Lys Ala Asp Glu Tyr Arg Phe Phe Lys Pro
        115                 120                 125

Trp Leu Gly Asn Gly Leu Leu Ile Ser Thr Gly Gln Lys Trp Arg Ser
130                 135                 140

His Arg Lys Leu Ile Ala Pro Thr Phe His Leu Asn Val Leu Lys Ser
145                 150                 155                 160

Phe Ile Asp Leu Phe Asn Ala Asn Ser Arg Ala Val Val Asp Lys Leu
                165                 170                 175

Lys Lys Glu Ser Gly Thr Phe Asp Cys His Asp Tyr Met Ser Glu Cys
            180                 185                 190

Thr Val Glu Ile Leu Leu Glu Thr Ala Met Gly Val Ser Lys Ser Thr
        195                 200                 205

Gln Asp Gln Ser Gly Phe Glu Tyr Ala Met Ala Val Met Lys Met Cys
210                 215                 220

Asp Ile Leu His Leu Arg His Thr Lys Ile Trp Leu Arg Pro Asp Leu
225                 230                 235                 240

Leu Phe Lys Leu Thr Asp Tyr Ala Lys Asn Gln Thr Arg Leu Leu Asp
                245                 250                 255

Val Ile His Gly Leu Thr Lys Lys Val Ile Lys Arg Lys Lys Glu Glu
            260                 265                 270

Phe Gln Ser Gly Lys Lys Ala Thr Ile Met Pro Glu Gly Asn Asp Val
        275                 280                 285

```
Thr Asn Glu Val Pro Ser Ser Lys Leu Thr Ser Val Glu Gly Leu Ser
    290                 295                 300

Phe Gly Gln Ser Ser Gly Leu Lys Asp Asp Leu Asp Val Asp Asp Asp
305                 310                 315                 320

Val Gly Gln Lys Lys Arg Leu Ala Phe Leu Asp Leu Leu Leu Glu Ser
                325                 330                 335

Ser Gln Ser Gly Val Val Ile Thr Asp Glu Glu Ile Lys Glu Gln Val
                340                 345                 350

Asp Thr Ile Met Phe Glu Gly His Asp Thr Thr Ala Ala Gly Ser Ser
                355                 360                 365

Phe Phe Leu Ser Met Met Gly Ile His Gln His Ile Gln Asp Lys Val
    370                 375                 380

Ile Glu Glu Leu Asp His Ile Phe Gly Asp Ser Asp Arg Pro Ala Thr
385                 390                 395                 400

Phe Gln Asp Thr Leu Glu Met Lys Tyr Leu Glu Arg Cys Leu Met Glu
                405                 410                 415

Thr Leu Arg Leu Tyr Pro Pro Val Pro Ile Ile Ala Arg His Leu Lys
                420                 425                 430

Glu Glu Ile Thr Leu Pro Ser Asn Gly Lys Lys Val Pro Ile Gly Thr
                435                 440                 445

Thr Leu Ile Val Gly Thr Tyr Lys Leu His Arg Arg Pro Asp Val Tyr
    450                 455                 460

Pro Asn Pro His Lys Phe Asp Pro Asp Asn Phe Leu Pro Glu Arg Ser
465                 470                 475                 480

Ala Asn Arg His Tyr Tyr Ala Phe Val Pro Phe Ser Ala Gly Pro Arg
                485                 490                 495

Ser Cys Val Gly Arg Lys Tyr Ala Met Leu Lys Leu Lys Ile Ile Leu
                500                 505                 510

Ser Thr Ile Leu Arg Asn Phe Arg Val Tyr Ser Asp Leu Asn Glu Ser
    515                 520                 525

Asp Phe Lys Leu Gln Ala Asp Ile Ile Leu Lys Arg Ala Glu Gly Phe
530                 535                 540

Lys Val Arg Leu Gln Pro Arg Lys Lys Gln Ala Lys Val
545                 550                 555

<210> SEQ ID NO 30
<211> LENGTH: 557
<212> TYPE: PRT
<213> ORGANISM: Mamestra brassicae

<400> SEQUENCE: 30

Met Ser Tyr Ala Ala Ala Glu Ser Val Val Pro Thr Ser Thr Trp Ala
1               5                   10                  15

Ala Thr Ser Leu Phe Tyr Val Leu Leu Val Pro Ala Leu Ile Leu Trp
                20                  25                  30

Tyr Ala Tyr Trp Arg Met Ser Arg Arg His Met Tyr Glu Leu Ala Ala
            35                  40                  45

Lys Leu His Gly Pro Pro Gly Leu Pro Leu Leu Gly Asn Ala Leu Glu
    50                  55                  60

Phe Thr Gly Gly Ser His Asp Ile Phe Arg Asn Val Ile Glu Lys Ser
65                  70                  75                  80

Ile Pro Tyr Asp Gly Glu Ser Val Val Lys Ile Trp Ile Gly Pro Arg
                85                  90                  95

Phe Trp Cys Ser Cys Thr Ile Leu Val Thr Trp Ser Leu Ile Leu Ser
                100                 105                 110
```

```
Ser His Thr His Ile Asp Lys Ala Asp Glu Tyr Arg Phe Phe Lys Pro
        115                 120                 125

Trp Leu Gly Asp Gly Leu Leu Ile Ser Thr Gly Gln Lys Trp Arg Ser
    130                 135                 140

His Arg Lys Leu Ile Ala Pro Thr Phe His Leu Asn Val Leu Lys Ser
145                 150                 155                 160

Phe Ile Asp Leu Phe Asn Ala Asn Ser Arg Ala Val Val Ser Lys Leu
                165                 170                 175

Lys Lys Glu Ala Gly Glu Phe Asp Cys His Asp Tyr Met Ser Glu Cys
            180                 185                 190

Thr Val Glu Ile Leu Leu Glu Thr Ala Met Gly Val Ser Lys Ser Thr
        195                 200                 205

Gln Asp Gln Ser Gly Phe Glu Tyr Ala Met Ala Val Met Lys Met Cys
    210                 215                 220

Asp Ile Leu His Leu Arg His Thr Lys Ile Trp Leu Arg Pro Asn Leu
225                 230                 235                 240

Leu Phe Lys Leu Thr Asp Tyr Ala Lys Lys Gln Thr Lys Leu Leu Asp
                245                 250                 255

Val Ile His Gly Leu Thr Lys Lys Val Ile Arg Arg Lys Lys Glu Glu
            260                 265                 270

Phe Asn Ser Gly Lys Arg Pro Thr Ile Leu Gln Asp Cys Thr Thr Thr
        275                 280                 285

Thr Thr Glu Glu Ala Asn Lys Thr Thr Ser Val Glu Gly Leu Ser Phe
    290                 295                 300

Gly Gln Ser Ala Gly Leu Lys Asp Asp Leu Asp Val Asp Asp Ala Asp
305                 310                 315                 320

Val Gly Gln Lys Lys Arg Leu Ala Phe Leu Asp Leu Leu Leu Glu Ser
                325                 330                 335

Ser Gln Ser Gly Val Val Ile Ser Asp Glu Glu Ile Lys Glu Gln Val
            340                 345                 350

Asp Thr Ile Met Phe Glu Gly His Asp Thr Thr Ala Ala Gly Ser Ser
        355                 360                 365

Phe Phe Leu Ser Met Met Gly Ile His Gln Asp Ile Gln Asp Lys Val
    370                 375                 380

Ile Asp Glu Leu Asp Lys Ile Phe Gly Asp Ser Asp Arg Pro Ala Thr
385                 390                 395                 400

Phe Gln Asp Thr Leu Glu Met Lys Tyr Leu Glu Arg Cys Leu Met Glu
                405                 410                 415

Thr Leu Arg Met Phe Pro Pro Val Pro Ile Ile Ala Arg His Leu Lys
            420                 425                 430

Gln Asp Ile Thr Leu Pro Ser Cys Gly Lys Gln Val Pro Ala Gly Thr
        435                 440                 445

Thr Val Val Val Ala Thr Tyr Lys Leu His Arg Arg Pro Asp Val Tyr
    450                 455                 460

Pro Asn Pro Thr Glu Phe Asp Pro Asp Asn Phe Leu Pro Glu Lys Ser
465                 470                 475                 480

Ala Asn Arg His Tyr Tyr Ala Phe Val Pro Phe Ser Ala Gly Pro Arg
                485                 490                 495

Ser Cys Val Gly Arg Lys Tyr Ala Met Leu Lys Leu Lys Ile Ile Leu
            500                 505                 510

Ser Thr Ile Leu Arg Ser Phe Arg Val His Ser Asp Leu Lys Glu Ser
        515                 520                 525

Asp Phe Lys Leu Gln Ala Asp Ile Ile Leu Lys Arg Ala Glu Gly Phe
```

```
            530                 535                 540
Lys Val Arg Leu Glu Pro Arg Lys Thr Thr Lys Ala Tyr
545                 550                 555

<210> SEQ ID NO 31
<211> LENGTH: 565
<212> TYPE: PRT
<213> ORGANISM: Acyrthosiphon pisum

<400> SEQUENCE: 31

Met Val Thr Asn Val Gln Gly Val Asn Pro Leu Phe Ala Leu Ser Ala
1               5                   10                  15

Phe Asn Leu Phe Phe Tyr Leu Leu Thr Pro Ala Ile Val Leu Trp Tyr
                20                  25                  30

Ile Tyr Phe Arg Met Ser Arg Lys Gln Leu Tyr Asp Leu Ala Ser Lys
            35                  40                  45

Ile Pro Gly Ser Glu Gly Leu Pro Leu Leu Gly Asn Ala Leu Asp Phe
        50                  55                  60

Met Gln Asp Pro His Thr Ile Phe Glu Lys Ile Tyr Glu Arg Ser Phe
65                  70                  75                  80

Glu Phe Glu Lys Asn Ser Pro Ile Lys Met Trp Ile Gly Pro Arg Leu
                85                  90                  95

Leu Val Phe Leu Thr Asp Pro Arg Asp Val Glu Val Ile Leu Ser Ser
            100                 105                 110

Asn Val Tyr Ile Asp Lys Ser Pro Glu Tyr Arg Leu Phe Glu Pro Trp
        115                 120                 125

Leu Gly Asn Gly Leu Leu Ile Ser Thr Gly Asp Lys Trp Arg Ala His
130                 135                 140

Arg Lys Leu Ile Ala Pro Thr Phe His Leu Asn Val Leu Lys Ser Phe
145                 150                 155                 160

Val Thr Leu Phe Asn Val Asn Ser Arg Asp Thr Val Ser Lys Leu Arg
                165                 170                 175

Lys Met Gly Ser Ser Thr Phe Asp Ile His Asp Phe Met Ser Glu Cys
            180                 185                 190

Thr Val Glu Ile Leu Leu Glu Thr Ala Met Gly Val Ser Lys Lys Thr
        195                 200                 205

Gln Lys Lys Ser Gly Phe Glu Tyr Ala Ala Ala Val Met Lys Met Cys
210                 215                 220

Asp Ile Leu His Met Arg His Thr Asn Leu Trp Leu Lys Pro Asp Phe
225                 230                 235                 240

Ile Phe Asn Phe Thr Lys Tyr Ala Lys Glu Gln Val Gly Leu Leu Asp
                245                 250                 255

Leu Ile His Gly Leu Thr Asn Asn Val Leu Ala Lys Lys Lys Glu Glu
            260                 265                 270

Phe Leu Lys Lys Lys Ser Leu Met Lys Glu Val Ser Asp Ile Pro Ala
        275                 280                 285

Ala Ser Glu Glu Ile Val Glu Thr Ser Ser Thr Leu Glu Val Glu Glu
290                 295                 300

Val Pro Tyr Gly Asn Ser Phe Gly Gln Ser Ala Gly Leu Lys Asp Asp
305                 310                 315                 320

Leu Asp Val Glu Asp Gly Ile Gly Glu Lys Lys Arg Val Ala Phe
                325                 330                 335

Leu Asp Leu Leu Ile Glu Cys Ser Glu Asn Gly Val Val Leu Ser Asp
            340                 345                 350

Glu Glu Val Arg Glu Gln Val Asp Thr Ile Met Phe Glu Gly His Asp
```

```
                    355                 360                 365
Thr Thr Ala Ala Gly Ser Ser Phe Phe Leu Cys Leu Met Gly Ala His
    370                 375                 380

Gln Asp Val Gln Lys Val Val Asp Glu Leu Tyr Ser Ile Phe Gly
385                 390                 395                 400

Asp Ser Asp Arg Pro Val Thr Phe Gln Asp Thr Leu Gln Met Lys Tyr
                405                 410                 415

Met Glu Arg Cys Ile Met Glu Thr Leu Arg Met Tyr Pro Pro Val Pro
            420                 425                 430

Ile Ile Ser Arg Gln Ile Lys Glu Lys Val Lys Leu Gly Glu Asp Ile
            435                 440                 445

Thr Leu Pro Val Gly Ala Thr Ile Val Ile Ala Thr Phe Lys Ile His
    450                 455                 460

Arg Asn Glu Asp Val Phe Pro Asn Pro Glu Val Phe Asn Pro Asp Asn
465                 470                 475                 480

Phe Leu Pro Glu Lys Ser Ala Ser Arg His Tyr Tyr Ala Tyr Val Pro
                485                 490                 495

Phe Ser Ala Gly Pro Arg Ser Cys Val Gly Arg Lys Tyr Ala Met Leu
            500                 505                 510

Lys Leu Lys Ile Ile Leu Ser Thr Ile Leu Arg Asn Phe Lys Ile Asn
            515                 520                 525

Ser Asn Leu Thr Glu Lys Asp Trp Lys Leu Gln Ala Asp Ile Ile Leu
    530                 535                 540

Lys Arg Thr Asp Gly Phe Lys Leu Ser Leu Glu Pro Arg Lys Ser Leu
545                 550                 555                 560

Ala Lys Thr Ala Ala
                565

<210> SEQ ID NO 32
<211> LENGTH: 817
<212> TYPE: PRT
<213> ORGANISM: Drosophila persimilis

<400> SEQUENCE: 32

Met Ser Thr Val Glu Val Leu Leu His Glu Phe Tyr Gln Pro Thr Thr
1               5                   10                  15

Ser Asn Ala Arg Lys Arg Glu Ile Glu Thr Asn Leu Leu Ala Phe Lys
            20                  25                  30

Ser Gln Pro Glu Ala Trp Gln Leu Cys Leu Arg Val Ala Thr Ala Gly
        35                  40                  45

Asn Ser Phe Thr Asp Asn Gln Phe Leu Trp Phe Ser Thr Ser Thr
    50                  55                  60

Leu Glu His Thr Ile Thr Arg Arg Trp Ala Gln Leu Thr Pro Ser Asp
65                  70                  75                  80

Arg Ala Gln Leu Arg Glu Thr Leu Trp Asn Thr Tyr Ala Gln Leu Gly
                85                  90                  95

Met Leu Asn Gly Ala Arg Arg His Arg Asp Thr Leu Ala Gln Leu Ile
            100                 105                 110

Ala Leu Met Gly Lys Arg Glu Phe Pro Glu Gln Asp Pro Asn Tyr Met
            115                 120                 125

Gln His Cys Met Glu Leu Thr Lys Thr Arg Phe Ala Leu Gly Ile Asn
        130                 135                 140

Leu Leu Arg Val Thr Ser Glu Glu Val Ser Asn Arg Gly Asp Leu
145                 150                 155                 160

Thr Thr Glu Trp Lys Gln Tyr Phe Tyr Ser Cys Ile Ser Met Cys Ile
```

-continued

```
                165                 170                 175
Pro Asp Val Met Asp Leu Val Thr Lys Tyr Leu Leu Ile Ala Val Cys
                    180                 185                 190
His Ile Asn Gly Lys Asp Ile Gln Ser Thr Ile Pro Asn Thr Leu Met
                    195                 200                 205
Asp Phe Ser Leu Thr Ser Ala Leu Pro Asn Asp Asn Gln Leu Ser Ser
                    210                 215                 220
Ser Ile Leu Glu Leu Leu Gly Cys Val Gln His Leu Val Ser Trp Ile
225                 230                 235                 240
Arg Thr Glu Leu Ile Ser Glu Tyr Phe Leu Met Ser Ile Leu Asp Leu
                    245                 250                 255
Ser Gln Trp Arg Pro Ala Asn Glu Pro Ile Ser Leu Ala Ala Leu Ser
                    260                 265                 270
Val Leu Asn Glu Leu Leu Tyr Leu Gln Lys Pro Leu Pro Tyr Ala Gly
                    275                 280                 285
Thr Leu Met Gly Gly Val Ser Ser Leu Leu Glu Gln His Asn Val Asn
                    290                 295                 300
Lys Gln Gln Ser Glu Met Tyr Ser Asp Lys Leu Arg Glu Leu Leu Arg
305                 310                 315                 320
Leu Tyr Thr Thr Lys Tyr Ala Gly Lys Leu Met Gln Glu Pro Glu Val
                    325                 330                 335
Leu Glu Thr Phe Leu Asn Gln Leu Tyr Gly Cys Thr Thr Glu Leu His
                    340                 345                 350
Gly Ala Leu Asp Phe Thr Glu Lys Leu Asp Ile Trp Ser Pro Ile Ile
                    355                 360                 365
Lys Ala Ile Ala Gln Gln Pro Ala Lys Ile Thr Arg Phe Asn Gln Val
                    370                 375                 380
Phe Thr Gln Leu Val Asp Glu Ile Met Arg Arg Thr Gln Phe Glu Ala
385                 390                 395                 400
Asn Lys Pro Glu Leu Glu Val Leu Asp Asn Glu Leu Met Glu Asp Asp
                    405                 410                 415
Thr Pro Thr Thr Glu Trp Gln Gln Phe Leu Asp Gln Cys Phe Glu Cys
                    420                 425                 430
Leu Ala Leu Leu Ala Ser Thr Arg Gly Ala His Ile Val Phe Ala Gln
                    435                 440                 445
Val Phe Ala His Trp Ser Arg Pro Gln Met Tyr Leu Met Ser Leu Glu
                    450                 455                 460
His Ala Leu Asp His Gly Ser Ser Arg Ser Tyr Glu Ala Ala Arg Lys
465                 470                 475                 480
Leu Lys His Ala Asn Val Gly Glu Ile Leu Arg Asp Phe Ala Thr Val
                    485                 490                 495
Cys Gln Ala Val Val Arg Leu Ala Pro Leu Met Asp Thr Ser Thr Ala
                    500                 505                 510
Ala Pro Gly Val Ala Asp Glu Met Glu Ala Gln Leu Gln Met Leu Ser
                    515                 520                 525
Asp Ser Leu Cys Arg Arg Cys Ser Phe Trp Pro Ala Ile Ala Ser Glu
                    530                 535                 540
Glu Gln Ile Trp Thr Arg Pro Pro Phe Arg Leu Ile Trp Ile Thr Ser
545                 550                 555                 560
Ala Thr Lys Lys Glu Gly Leu Arg Asp Asp Leu Asp Asp Ile Asp Glu
                    565                 570                 575
Asn Asp Val Gly Ala Lys Arg Arg Leu Ala Leu Leu Asp Ala Met Val
                    580                 585                 590
```

```
Glu Met Ala Lys Asn Pro Asp Ile Glu Trp Asn Glu Lys Asp Ile Ile
            595                 600                 605
Asp Glu Val Asn Thr Ile Met Phe Glu Gly His Asp Thr Thr Ser Ala
            610                 615                 620
Gly Ser Ser Phe Ala Leu Cys Met Met Gly Ile His Lys Asp Ile Gln
625                 630                 635                 640
Glu Lys Val Phe Ala Glu Gln Lys Ala Ile Phe Gly Asp Asn Met Leu
            645                 650                 655
Arg Asp Cys Thr Phe Ala Asp Thr Asn Glu Met Lys Tyr Leu Glu Arg
            660                 665                 670
Val Ile Leu Glu Thr Leu Arg Leu Tyr Pro Val Pro Leu Ile Ala
            675                 680                 685
Arg Arg Leu Asp Tyr Asp Leu Lys Leu Ala Ser Gly Pro Tyr Thr Val
            690                 695                 700
Pro Lys Gly Thr Thr Val Ile Val Leu Gln Tyr Cys Val His Arg Arg
705                 710                 715                 720
Ala Asp Ile Tyr Pro Asn Pro Thr Lys Phe Asp Pro Asn Phe Leu
            725                 730                 735
Pro Glu Arg Met Ala Asn Arg His Tyr Tyr Ser Phe Ile Pro Phe Ser
            740                 745                 750
Ala Gly Pro Arg Ser Cys Val Gly Arg Lys Tyr Ala Met Leu Lys Leu
            755                 760                 765
Lys Val Leu Leu Ser Thr Ile Val Arg Asn Tyr Ile Val His Ser Thr
            770                 775                 780
Asp Thr Glu Ala Asp Phe Lys Leu Gln Ala Asp Ile Ile Leu Lys Leu
785                 790                 795                 800
Glu Asn Gly Phe Asn Ile Ser Leu Glu Lys Arg Lys Tyr Ala Thr Val
            805                 810                 815
Ala

<210> SEQ ID NO 33
<211> LENGTH: 511
<212> TYPE: PRT
<213> ORGANISM: Blaberus discoidalis

<400> SEQUENCE: 33

Met Glu Phe Ile Thr Ile Leu Leu Ser Thr Ala Leu Phe Ile Val Thr
1               5                   10                  15
Phe Leu Phe Leu Phe Arg Gln Gly Ala Lys Arg Ala Arg Phe Val Tyr
            20                  25                  30
Leu Val Asn Lys Leu Pro Gly Pro Thr Ala Tyr Pro Val Val Gly Asn
            35                  40                  45
Ala Ile Glu Ala Ile Val Pro Arg Asn Lys Leu Phe Gln Val Phe Asp
        50                  55                  60
Arg Arg Ala Lys Leu Tyr Gly Pro Leu Tyr Arg Ile Trp Ala Gly Pro
65                  70                  75                  80
Ile Ala Gln Val Gly Leu Thr Arg Pro Glu His Val Glu Leu Ile Leu
                85                  90                  95
Arg Asp Thr Lys His Ile Asp Lys Ser Leu Val Tyr Ser Phe Ile Arg
            100                 105                 110
Pro Trp Leu Gly Glu Gly Leu Leu Thr Gly Thr Gly Ala Lys Trp His
            115                 120                 125
Ser His Arg Lys Met Ile Thr Pro Thr Phe His Phe Lys Ile Leu Asp
        130                 135                 140
Ile Phe Val Asp Val Phe Val Glu Lys Ser Glu Ile Leu Val Lys Lys
```

```
                145                 150                 155                 160
Leu Gln Ser Lys Val Gly Gly Lys Asp Phe Asp Ile Tyr Pro Phe Ile
                    165                 170                 175

Thr His Cys Ala Leu Asp Ile Ile Cys Glu Thr Ala Met Gly Ile Gln
                180                 185                 190

Met Asn Ala Gln Glu Glu Ser Glu Ser Glu Tyr Val Lys Ala Val Tyr
            195                 200                 205

Glu Ile Ser Glu Leu Thr Met Gln Arg Ser Val Arg Pro Trp Leu His
        210                 215                 220

Pro Lys Val Ile Phe Asp Leu Thr Thr Met Gly Lys Arg Tyr Ala Glu
225                 230                 235                 240

Cys Leu Arg Ile Leu His Gly Phe Thr Asn Lys Val Ile Gln Glu Arg
                245                 250                 255

Lys Ser Leu Arg Gln Met Thr Gly Met Lys Pro Thr Ile Ser Asn Glu
                260                 265                 270

Glu Asp Glu Leu Leu Gly Lys Lys Lys Arg Leu Ala Phe Leu Asp Leu
            275                 280                 285

Leu Leu Glu Ala Ser Glu Asn Gly Thr Lys Met Ser Asp Thr Asp Ile
        290                 295                 300

Arg Glu Glu Val Asp Thr Phe Met Phe Glu Gly His Asp Thr Thr Ser
305                 310                 315                 320

Ala Gly Ile Cys Trp Ala Leu Phe Leu Leu Gly Ser His Pro Glu Ile
                325                 330                 335

Gln Asp Lys Val Tyr Glu Glu Leu Asp His Ile Phe Gln Gly Ser Asp
                340                 345                 350

Arg Ser Thr Thr Met Arg Asp Leu Ala Asp Met Lys Tyr Leu Glu Arg
            355                 360                 365

Val Ile Lys Glu Ser Leu Arg Leu Phe Pro Ser Val Pro Phe Ile Gly
        370                 375                 380

Arg Val Leu Lys Glu Asp Thr Lys Ile Gly Asp Tyr Leu Val Pro Ala
385                 390                 395                 400

Gly Cys Met Met Asn Leu Gln Ile Tyr His Val His Arg Asn Gln Asp
                405                 410                 415

Gln Tyr Pro Asn Pro Glu Ala Phe Asn Pro Asp Asn Phe Leu Pro Glu
                420                 425                 430

Arg Val Ala Lys Arg His Pro Tyr Ala Tyr Val Pro Phe Ser Ala Gly
            435                 440                 445

Pro Arg Asn Cys Ile Gly Gln Lys Phe Ala Thr Leu Glu Glu Lys Thr
        450                 455                 460

Val Leu Ser Ser Ile Leu Arg Asn Phe Lys Val Arg Ser Ile Glu Lys
465                 470                 475                 480

Arg Glu Asp Leu Thr Leu Met Asn Glu Leu Ile Leu Arg Pro Glu Ser
                485                 490                 495

Gly Ile Lys Val Glu Leu Ile Pro Arg Leu Pro Ala Asp Ala Cys
                500                 505                 510

<210> SEQ ID NO 34
<211> LENGTH: 515
<212> TYPE: PRT
<213> ORGANISM: Carcinus maenas

<400> SEQUENCE: 34

Met Ala Leu Leu Leu Gly Arg Glu Phe Val Trp Trp Ser Ser Val Ala
1               5                   10                  15

Ser Tyr Ser Leu Gly Thr Ala Cys Leu Ala Leu Leu Leu Thr Trp Phe
```

```
                  20                  25                  30
Ile Arg Arg Gln Gln Thr Val Trp Leu Ile Glu Lys Leu Pro Gly Pro
            35                  40                  45

Arg Ser Leu Pro Ile Leu Gly Asn Ala Leu Asp Val Asn Val Ala Pro
        50                  55                  60

Arg Glu Leu Phe Leu Lys Ile Met Glu Phe Cys Glu Tyr Gly Asn Thr
65                  70                  75                  80

Val Lys Ile Trp Leu Gly Met Tyr Pro Tyr Cys Leu Val Ser Glu Ala
                85                  90                  95

Lys Ser Ala Glu Val Leu Leu Ser Ser Asn Lys His Leu Asp Lys Ser
            100                 105                 110

Arg Asp Tyr Asn Phe Leu His Pro Trp Leu Gly Thr Gly Leu Leu Thr
        115                 120                 125

Ser Thr Gly Lys Lys Trp His Ser Arg Arg Lys Ile Leu Thr Pro Ala
130                 135                 140

Phe His Phe Lys Ile Leu Glu Asp Phe Val Glu Val Phe Asn Ser Gln
145                 150                 155                 160

Ser Asn Lys Met Leu Asp Lys Leu Thr Pro Lys Ala Asp Gly Lys Ala
                165                 170                 175

Phe Asp Ile Phe Pro Tyr Ile Thr Leu Cys Thr Leu Asp Ile Ile Cys
            180                 185                 190

Glu Thr Ala Met Gly Ile Asn Ile Asn Ala Gln Gly Asn Ser Asn Ser
        195                 200                 205

Glu Tyr Val Asn Ala Val Tyr Arg Ile Gly Ala Leu Val Gln His Arg
210                 215                 220

Gln Thr Arg Pro Trp Ile Gln Pro Asp Phe Leu Phe Arg Leu Phe Gly
225                 230                 235                 240

Tyr Ala Lys Leu His Asp Glu Tyr Leu Arg Val Leu His His Phe Ser
                245                 250                 255

Asn Ser Ala Ile Glu Asn Arg Arg Lys Glu Tyr Gln Leu Glu Lys Leu
            260                 265                 270

Asn Ala Lys Glu Asn Ile Asp Asp Val Ile Gly Lys Lys Arg Arg
        275                 280                 285

Leu Ala Phe Leu Asp Leu Leu Leu Asn Tyr Ser Glu Thr Gln Met Pro
290                 295                 300

Leu Ser Asn Glu Asp Ile Arg Glu Glu Val Asp Thr Phe Met Phe Glu
305                 310                 315                 320

Gly His Asp Thr Thr Ala Ala Ala Leu Asn Trp Ser Val Tyr Leu Leu
                325                 330                 335

Gly Cys His Pro Glu Ile Gln Ala Lys Val His Glu Glu Leu Asp Ala
            340                 345                 350

Leu Phe Gly Asp Ser Asp Arg Pro Val Thr Met Ala Asp Leu Arg Glu
        355                 360                 365

Met Lys Tyr Thr Glu Asn Cys Ile Lys Glu Ala Leu Arg Leu Phe Pro
370                 375                 380

Ser Val Pro Phe Leu Ala Arg Glu Leu Arg Glu Glu Ala Val Ile Asn
385                 390                 395                 400

Asn Tyr Arg Ile Pro Val Gly Thr Thr Val Met Val Ile Thr Tyr Arg
                405                 410                 415

Leu His Arg Asp Pro Glu Gln Phe Pro Asn Pro Glu Thr Phe Asp Pro
            420                 425                 430

Asp Arg Phe Leu Pro Glu Asn Val Ala Lys Arg His Pro Tyr Ser Tyr
        435                 440                 445
```

-continued

```
Val Pro Phe Ser Ala Gly Pro Arg Asn Cys Ile Gly Gln Lys Phe Ala
            450                 455                 460

Ile Met Glu Glu Lys Ile Val Leu Ser Ser Ile Met Arg Arg Phe Arg
465                 470                 475                 480

Val Glu Ser Thr Thr Arg Arg Glu Glu Leu Lys Leu Leu Gly Glu Leu
                    485                 490                 495

Ile Leu Arg Pro Glu Asn Gly Asn Thr Val Lys Leu Ile Pro Arg Thr
                500                 505                 510

Pro Lys Val
        515

<210> SEQ ID NO 35
<211> LENGTH: 516
<212> TYPE: PRT
<213> ORGANISM: Branchiostoma floridae

<400> SEQUENCE: 35

Met Ala Ala Val Leu Trp Thr Ala Ala Val Ala Val Ala Ser Val
1               5                   10                  15

Thr Ile Trp Ala Ile Phe Ala Phe Ala Arg Trp Trp Lys Leu Trp Lys
                20                  25                  30

Thr Ile Asn Lys Ile Pro Gly Pro Ala Tyr Pro Leu Val Gly Asn
                35                  40                  45

Ala Leu Glu Phe Lys Pro Gly Ala Val Glu Phe Ala Gln Leu Phe
    50                  55                  60

Gly Trp Gly Lys Ala Tyr Ala Ser Ala Pro Val Leu Arg Trp Trp Ile
65                  70                  75                  80

Gly Pro His Pro Met Val Ala Leu His Pro Glu Met Leu Gln Val
                85                  90                  95

Leu Phe Ser Ser Lys His Ile Glu Lys Ser Phe Val Tyr Asp Phe
                100                 105                 110

Leu His Pro Trp Leu Gly Thr Gly Leu Leu Thr Ser Ala Gly Asp Lys
                115                 120                 125

Trp Lys Thr Arg Arg Arg Leu Ile Thr Pro Thr Phe His Phe Lys Ile
    130                 135                 140

Leu Gly Asp Phe Leu His Glu Phe Asn Asp Gln Ser Glu Ile Met Val
145                 150                 155                 160

Arg Lys Leu Glu Glu Met Ala Gly Thr Gly Glu Glu Phe Asp Val Phe
                165                 170                 175

Pro Phe Ile Thr Leu Cys Ala Leu Asp Ile Ile Cys Gly Thr Ala Met
                180                 185                 190

Gly Gln Ser Leu Asn Ala Gln Glu Asn Thr Asp Ser Asp Tyr Val Arg
                195                 200                 205

Ala Ile Tyr Arg Ile Ser Asp Leu Ile Gln Val Arg Gln Lys Ser Pro
    210                 215                 220

Trp Tyr Trp Ser Asp Pro Ile Tyr Lys Gly Phe Gly Pro Gly Arg Glu
225                 230                 235                 240

Phe Glu Glu Thr Leu Arg Ile Leu His Asp Phe Thr Arg Ser Val Ile
                245                 250                 255

Lys Glu Arg Ser Glu Gln Phe Gln Lys Gln Leu Glu Ser Gln Ser Gln
                260                 265                 270

Asp Ala Phe Asp Ile Val Glu Asp Pro Asp Lys Pro Ile Ala Ile Gly
    275                 280                 285

Gly Arg Lys Arg Leu Ala Phe Leu Asp Met Leu Leu Tyr Ala Ser Val
    290                 295                 300
```

```
Gly Glu Thr Lys Leu Thr Asn Glu Asp Ile Gln Glu Val Asp Thr
305                 310                 315                 320

Phe Met Phe Glu Gly His Asp Thr Thr Ala Ala Ala Asn Trp Ala
                325                 330                 335

Ile Phe Leu Ile Gly Ser His Pro Asp Val Gln Arg Lys Val His Glu
            340                 345                 350

Glu Met Asp Arg Val Met Ser Asp Pro Asp Glu Lys Pro Thr Met Asp
                355                 360                 365

Asp Leu Arg Glu Met Lys Tyr Leu Glu Cys Cys Ile Lys Glu Ala Leu
            370                 375                 380

Arg Leu Tyr Pro Ser Val Pro Phe Phe Ala Arg Thr Leu Ser Glu Asp
385                 390                 395                 400

Cys Val Ile Gly Gly Tyr Glu Val Pro Lys Gly Val Thr Ala Ile Val
                405                 410                 415

Pro Thr Tyr Asn Val His Arg Asp Pro Asn His Trp Pro Asp Ala Glu
            420                 425                 430

Lys Phe Asp Pro Glu Arg Phe Phe Pro Glu Asn Cys Ala Gly Arg His
            435                 440                 445

Pro Tyr Ala Tyr Ile Pro Phe Ser Ala Gly Ser Arg Asn Cys Ile Gly
            450                 455                 460

Gln Arg Phe Ala Leu Met Glu Glu Lys Ala Ile Leu Ser Ser Ile Phe
465                 470                 475                 480

Arg Arg Phe Arg Ile Glu Thr Met Gln Asn Arg Glu Asp Leu Lys Pro
                485                 490                 495

Leu Gly Glu Leu Ile Leu Arg Pro Glu Ser Gly Val Arg Ile Lys Leu
            500                 505                 510

Phe Arg Arg Glu
        515

<210> SEQ ID NO 36
<211> LENGTH: 525
<212> TYPE: PRT
<213> ORGANISM: Balaenoptera acutorostrata

<400> SEQUENCE: 36

Met Leu Ala Leu Trp Leu Leu Ser Val Gly Gln Lys Leu Leu Leu Trp
1               5                   10                  15

Gly Gly Leu Cys Ala Val Ser Leu Ala Gly Ala Ile Leu Thr Leu Asn
            20                  25                  30

Leu Leu Arg Met Ala Ala Ser Tyr Ala Trp Thr Trp Gln Arg Met Arg
        35                  40                  45

Ala Val Pro Thr Leu Glu Gly Ala Tyr Pro Phe Leu Gly His Ala Leu
    50                  55                  60

Leu Leu Lys Pro Asp Ala Arg Asp Phe Phe Gln Gln Met Ile Gln Tyr
65                  70                  75                  80

Thr Glu Glu His Arg His Leu Pro Leu Leu Lys Leu Trp Leu Gly Pro
                85                  90                  95

Ile Pro Val Val Phe Leu Tyr Asn Ala Glu Asn Val Glu Val Ile Leu
            100                 105                 110

Thr Ser Ser Lys His Ile Asp Lys Ser Tyr Met Tyr Lys Phe Leu Glu
        115                 120                 125

Pro Trp Leu Gly Leu Gly Leu Leu Thr Ser Thr Gly Asn Lys Trp Arg
    130                 135                 140

Ser Arg Arg Lys Met Leu Thr Pro Thr Phe His Phe Thr Ile Leu Glu
145                 150                 155                 160
```

Asp Phe Leu Asp Val Met Asn Glu Gln Ala Asn Ile Leu Val Asn Lys
              165                 170                 175

Leu Glu Lys Tyr Val Asn Gln Glu Ala Phe Asn Cys Phe Ser Tyr Ile
            180                 185                 190

Thr Leu Cys Ala Leu Asp Ile Ile Cys Glu Thr Ala Met Gly Lys Asn
        195                 200                 205

Ile Gly Ala Gln Ser Asn Asn Asp Ser Glu Tyr Val Gln Ala Val Tyr
    210                 215                 220

Arg Met Ser Asp Ser Ile His Gln Arg Met Lys Met Pro Trp Leu Trp
225                 230                 235                 240

Leu Asp Leu Leu Phe Phe Ile Phe Lys Asp Gly Trp Glu His Lys Arg
                245                 250                 255

Ser Leu Lys Ile Leu His Asn Phe Thr Lys Asn Val Ile Thr Glu Arg
            260                 265                 270

Ala Asn Glu Met Lys Arg His Glu Glu Gly Arg Ser Asn Asp Lys Asp
        275                 280                 285

Phe Pro Pro His Asn Asn Lys Arg Arg Gly Phe Leu Asp Leu Leu
    290                 295                 300

Asn Val Thr Asp Asp Gln Gly Asn Lys Leu Ser Tyr Glu Glu Ile Arg
305                 310                 315                 320

Glu Glu Val Asp Thr Phe Met Phe Glu Gly His Asp Thr Thr Ala Ala
                325                 330                 335

Ala Ile Asn Leu Ser Leu Tyr Leu Leu Gly Ser Tyr Pro Glu Val Gln
            340                 345                 350

Gln Lys Val Asp Asn Glu Leu Glu Val Phe Gly Arg Ser Asp Arg
        355                 360                 365

Pro Ala Thr Leu Asp Asp Leu Lys Lys Leu Lys Tyr Leu Glu Cys Val
    370                 375                 380

Val Lys Glu Ser Leu Arg Leu Phe Pro Ser Val Pro Phe Phe Ala Arg
385                 390                 395                 400

Asn Leu Asn Glu Asp Cys Glu Val Ala Gly Tyr Lys Ile Val Lys Gly
                405                 410                 415

Ser Gln Val Ile Ile Met Pro Tyr Ala Leu His Arg Asp Gln Arg Tyr
            420                 425                 430

Phe Pro Asn Pro Glu Glu Phe Lys Pro Glu Arg Phe Phe Pro Glu Asn
        435                 440                 445

Ser Lys Gly Arg His Ser Tyr Ala Tyr Val Pro Phe Ser Ala Gly Pro
    450                 455                 460

Arg Asn Cys Ile Gly Gln Lys Phe Ala Met Met Glu Glu Lys Thr Ile
465                 470                 475                 480

Leu Ser Cys Ile Leu Arg His Phe Trp Val Glu Ser Asn Gln Lys Arg
                485                 490                 495

Glu Glu Leu Gly Leu Ala Gly Glu Leu Ile Leu Arg Pro Ser Asn Gly
            500                 505                 510

Ile Trp Ile Lys Leu Lys Arg Arg Asn Thr Asn Glu Ser
    515                 520                 525

<210> SEQ ID NO 37
<211> LENGTH: 501
<212> TYPE: PRT
<213> ORGANISM: Helicoverpa zea

<400> SEQUENCE: 37

Met Phe Trp Phe Leu Leu Phe Phe Val Gly Phe Leu Cys Leu Leu His
1               5                   10                  15

```
Leu Leu Leu Asn Tyr Asn Glu Arg Ala Arg Leu Ile Arg Lys Leu Pro
            20                  25                  30

Gly Pro Glu Asp Ser Phe Ile Leu Gly Asn Gly Pro Ala Val Met Leu
        35                  40                  45

Ser Ser Val Glu Val Met Lys Leu Ala Arg Lys Leu Ala Gln Glu Asn
 50                  55                  60

Ser Gly Ile Tyr Arg Leu Trp Met Tyr Pro Val Ala Ala Val Ser Ile
 65                  70                  75                  80

Tyr Asn Pro Glu Asp Ile Glu Thr Ile Val Ser Ser Met Lys Tyr Asn
                85                  90                  95

Glu Lys Ser Gln Val Tyr Arg Phe Leu Lys Pro Trp Leu Gly Asp Gly
            100                 105                 110

Leu Leu Leu Ser Lys Gly Gln Lys Trp Gln Gln Arg Arg Lys Ile Leu
            115                 120                 125

Thr Pro Thr Phe His Phe Asn Ile Leu Lys Gln Phe Cys Glu Val Ile
            130                 135                 140

Ser Glu Asn Thr Gln Arg Phe Val Glu Asn Leu Lys Glu Val Ser Gly
145                 150                 155                 160

Arg Pro Ile Asp Val Val Pro Val Ile Ser Glu Phe Thr Leu Asn Ser
                165                 170                 175

Ile Cys Glu Thr Ala Met Gly Thr Asn Leu Thr Glu Tyr Asp Lys Thr
            180                 185                 190

Ala Ala Ser Ala Tyr Lys Glu Ala Ile His Asn Leu Gly Tyr Ile Phe
            195                 200                 205

Tyr Gln Arg Phe Ile Lys Val Tyr Tyr Phe Phe Asp Phe Ile Phe Asn
            210                 215                 220

Leu Ser Ser Leu Ser Lys Lys Gln Asp Gly Tyr Leu Lys Thr Val His
225                 230                 235                 240

Ser Phe Thr Lys Lys Val Ile Asp Glu Arg Ser Ala Tyr Ile Glu Lys
                245                 250                 255

His Gly Ile Lys Ile Pro Asp Glu Asn Asp Asp Asp Thr Tyr Val
            260                 265                 270

Tyr Lys Ser Lys Lys Lys Thr Ala Met Leu Asp Val Leu Ile Ser Ala
            275                 280                 285

Arg Lys Glu Gly His Ile Ser Asp Thr Gly Val Gln Glu Glu Val Asp
290                 295                 300

Thr Phe Met Phe Glu Gly His Asp Thr Thr Ala Gly Gly Leu Thr Tyr
305                 310                 315                 320

Cys Phe Met Leu Leu Ala Asn His Lys Glu Ala Gln Asp Lys Ile Leu
                325                 330                 335

Glu Glu Leu Lys Glu Ile Leu Gly Asp Asp Lys Arg Pro Ile Thr Met
            340                 345                 350

Glu Asp Leu Pro Lys Met Lys Tyr Leu Glu Arg Cys Ile Lys Glu Ser
            355                 360                 365

Leu Arg Leu Phe Pro Pro Val His Phe Ile Ser Arg Ser Leu Asn Glu
            370                 375                 380

Thr Val Thr Leu Ser Asn Tyr Lys Ile Pro Ala Gly Thr Leu Cys His
385                 390                 395                 400

Ile Gln Ile Tyr Asp Leu His Arg Arg Ala Asp Leu Phe Lys Asn Pro
                405                 410                 415

Thr Ser Phe Asp Pro Asp Arg Phe Leu Pro Glu Asn Ser Val Gly Arg
            420                 425                 430

His Pro Tyr Ala Tyr Ile Pro Phe Ser Ala Gly Pro Arg Asn Cys Ile
            435                 440                 445
```

-continued

Gly Gln Lys Phe Ala Met Met Glu Met Lys Ile Ala Val Ala Glu Val
    450                 455                 460

Leu Arg Glu Phe Glu Leu Gln Pro Val Thr Arg Pro Ser Asp Ile Arg
465                 470                 475                 480

Met Ile Ala Asp Ala Val Phe Arg Asn Asp Gly Pro Val Glu Val Thr
                485                 490                 495

Phe Val Lys Arg Gln
            500

<210> SEQ ID NO 38
<211> LENGTH: 526
<212> TYPE: PRT
<213> ORGANISM: Daphnia magna

<400> SEQUENCE: 38

Met Asp Val Thr Ser Gly Gly Glu Ser Ser Val Trp Ile Ser Ser Phe
1               5                   10                  15

Ser Val Tyr Thr Val Thr Thr Ile Leu Val Thr Leu Val Val Leu Ala
            20                  25                  30

Val Val Lys Arg Tyr Asn Phe Met Gln Arg Cys Asn Lys Val Leu Gly
        35                  40                  45

Ser Pro Thr Asp Ile Pro Leu Phe Gly Gly Gly Ser Leu Ile Phe Val
    50                  55                  60

Pro Pro Glu Glu Ile Met Asn Leu Leu Leu Leu His Val Val Phe
65                  70                  75                  80

Gly Arg Leu Ser Pro Ser Gly Ile Ile Arg Ala Trp Ile Gly Pro Leu
                85                  90                  95

Pro Met Phe Phe Ala Thr Thr Ala Glu Ala Val Glu Ala Val Leu Ser
            100                 105                 110

Ser Asn Lys Ile Ile Thr Lys Ser Arg Glu Tyr Asp Phe Leu His Pro
        115                 120                 125

Trp Leu Asn Thr Gly Leu Leu Thr Ser Thr Gly Ser Lys Trp Gln Thr
    130                 135                 140

Arg Arg Lys Leu Leu Thr Pro Ala Phe His Phe Lys Ile Leu Glu Asp
145                 150                 155                 160

Phe Val His Val Phe Asn Glu Gln Ser Leu Ile Leu Val Asn Lys Leu
                165                 170                 175

Asn Gln Ala Val Ala Lys Asp Lys Asp Leu Asn Ile Phe Pro Phe Val
            180                 185                 190

Thr Leu Cys Thr Leu Asp Ile Ile Cys Glu Thr Ala Met Gly Arg Asn
        195                 200                 205

Val Glu Ala Gln Ser Lys Thr Asp Ser Ala Tyr Val Gln Ala Val Tyr
    210                 215                 220

Asn Met Ser Gln Leu Ile Gln His Arg Gln Val Arg Phe Tyr Leu Trp
225                 230                 235                 240

Leu Asp Trp Met Phe Lys Leu Ser Ser His Trp Pro Glu Gln Arg Lys
                245                 250                 255

Thr Leu Gly Ile Leu His Gly Phe Thr Asn Lys Val Ile Gln Glu Arg
            260                 265                 270

Lys Ala Glu His Gln Gln Arg Ser Ser Asp Ile Ala Glu Pro Ser Lys
        275                 280                 285

Asp Val Thr Glu Asp Ala Val Phe Ser Lys Arg Arg Leu Ala Phe Leu
    290                 295                 300

Asp Leu Leu Ile Glu Phe Ser Gln Gly Gly Thr Val Leu Ser Ala Ser
305                 310                 315                 320

```
Asp Ile Arg Glu Glu Val Asp Thr Phe Met Phe Glu Gly His Asp Thr
            325                 330                 335

Thr Ser Ala Ala Ile Thr Trp Ser Ile Phe Leu Ile Gly Ser His Pro
            340                 345                 350

Glu Val Gln Glu Met Val Asn Glu Leu Asp Arg Val Phe Gly Asp
            355                 360                 365

Ser Asp Arg Pro Ala Thr Met Ala Asp Leu Ser Glu Leu Lys Tyr Leu
            370                 375                 380

Glu Cys Cys Val Lys Glu Ala Leu Arg Leu Tyr Pro Ser Val Pro Ile
385                 390                 395                 400

Ile Ser Arg Thr Cys Val Glu Asp Thr Val Ile Gly Gly Asp Glu Ile
            405                 410                 415

Pro Ala Gly Thr Ser Val Ser Ile Cys Ser Tyr Tyr Leu His Arg Asp
            420                 425                 430

Pro Lys Tyr Phe Pro Asp Pro Glu Leu Tyr Gln Pro Lys Arg Phe Leu
            435                 440                 445

Ala Glu His Ala Glu Arg Arg His Pro Tyr Ser Tyr Val Pro Phe Ser
            450                 455                 460

Ala Gly Pro Arg Asn Cys Ile Gly Gln Arg Phe Ala Leu Met Glu Glu
465                 470                 475                 480

Lys Ala Val Leu Ser Ala Ile Leu Arg Asn Phe His Val Gln Ser Leu
            485                 490                 495

Asp Lys Arg Glu Glu Ile Ile Leu Leu Ala Glu Leu Ile Leu Arg Pro
            500                 505                 510

Arg Asp Gly Ile Arg Val Arg Leu Glu Pro Lys Lys Gln
            515                 520                 525

<210> SEQ ID NO 39
<211> LENGTH: 520
<212> TYPE: PRT
<213> ORGANISM: Nilaparvata lugens

<400> SEQUENCE: 39

Met Ala Lys Thr Ala Asn Gly Ser Ile Lys Met Asp Tyr Thr Thr Thr
1               5                   10                  15

Ile Leu Ser Leu Val Leu Phe Ile Phe Ser Ala Leu Tyr Leu Leu Arg
            20                  25                  30

Gln Ala Phe Arg Arg Ile Lys Ile Ile Asn Met Val Asp Gln Leu Pro
            35                  40                  45

Gly Pro Arg Ala Tyr Pro Ile Ile Gly Asn Ala Leu Asp Phe Met Val
        50                  55                  60

Pro Arg Ser Glu Leu Met Asn Val Phe Asp Ser Arg Thr Lys Lys Tyr
65                  70                  75                  80

Gly Pro Leu Phe Arg Thr Trp Ala Gly Pro Val Pro Gln Ile His Ile
            85                  90                  95

Thr Arg Pro Glu His Met Glu Ile Val Met Ser Ser Leu Lys His Ile
            100                 105                 110

Asp Lys Ser Lys Ala Tyr Thr Phe Leu Gln Pro Gly Leu Gly Thr Gly
            115                 120                 125

Leu Leu Thr Gly Thr Gly Ala Lys Trp His Ser His Arg Lys Met Ile
            130                 135                 140

Thr Pro Thr Leu His Phe Lys Ile Leu Asp Val Phe Val Glu Val Phe
145                 150                 155                 160

Gly Glu Lys Cys Gln Thr Leu Ile Glu Asn Leu Leu Lys Lys Ala Asp
            165                 170                 175
```

```
Gly Gln Glu Phe Asp Ile Tyr Pro Phe Ile Thr His Cys Ala Leu Asp
            180                 185                 190

Ile Ile Cys Glu Thr Ala Met Gly Thr Gln Ile Asn Ala Gln Asn Glu
            195                 200                 205

Ser Asp Ser Asp Tyr Val Arg Ala Ile Tyr Asp Ile Ser Glu Leu Thr
210                 215                 220

Thr Glu Arg Thr Thr Lys Pro Trp Leu His Ser Asp Leu Ile Trp Lys
225                 230                 235                 240

Ser Ser Lys Arg Gly Ala Arg Tyr Ala His Asp Leu Ser Ile Leu His
            245                 250                 255

Gly Phe Thr Asn Arg Val Ile Ser Glu Arg Lys Val Ala Arg Leu Ala
            260                 265                 270

Asp Lys Glu Arg Ile Lys Asn His Glu Asp Asp Glu Phe Leu Gly
            275                 280                 285

Lys Lys Lys Arg Met Ala Phe Leu Asp Leu Leu Glu Ala Ser Glu
290                 295                 300

Leu Gly Gln Lys Leu Thr Asp Asp Glu Ile Arg Glu Glu Val Asp Thr
305                 310                 315                 320

Phe Met Phe Glu Gly His Asp Thr Thr Thr Ala Gly Ile Cys Trp Ser
            325                 330                 335

Leu Phe Met Leu Gly Asn His Pro Glu Tyr Gln Asp Gln Val Ala Gln
            340                 345                 350

Glu Leu Asp Gln Ile Phe Gly Asp Ser Asn Leu Pro Pro Thr Met Lys
            355                 360                 365

Asp Leu Asn Glu Met Lys Tyr Leu Glu Arg Val Ile Lys Glu Ser Leu
370                 375                 380

Arg Leu Phe Pro Ser Val Pro Phe Ile Gly Arg Tyr Leu Gly Glu Asp
385                 390                 395                 400

Thr Lys Phe Asp Asn Tyr Ile Val Pro Ala Gly Cys Val Met Asn Leu
            405                 410                 415

Gln Ile Phe His Val His Arg Cys Pro Asp Gln Phe Pro Asp Pro Glu
            420                 425                 430

Lys Phe Asn Pro Asp Asn Phe Leu Pro Glu Arg Thr Gln Gly Arg His
            435                 440                 445

Pro Tyr Ala Tyr Ile Pro Phe Ser Ala Gly Pro Arg Asn Cys Ile Gly
            450                 455                 460

Gln Lys Phe Ala Val Leu Glu Glu Lys Thr Val Leu Ser Ser Ile Leu
465                 470                 475                 480

Arg Asn Tyr Arg Val Glu Ser Val Glu Lys Leu Glu Asp Leu Asn Leu
            485                 490                 495

Met Asn Glu Leu Ile Leu Arg Pro Glu Ser Gly Ile Arg Met Arg Ile
            500                 505                 510

Tyr Pro Arg Lys Lys Thr Gln Ser
            515                 520

<210> SEQ ID NO 40
<211> LENGTH: 510
<212> TYPE: PRT
<213> ORGANISM: Danio rerio

<400> SEQUENCE: 40

Met Gly Ile Leu Phe Gly Leu Tyr Ile Leu Gly Ile Leu Phe Thr Ala
1               5                   10                  15

Val Leu Leu Leu Leu Leu Ala Ser Thr Ala Tyr Asn Pro Leu Lys Asn
            20                  25                  30
```

Tyr Ile Gly Lys Trp Asn Glu Met Arg Pro Ile Pro Gly Met Ala Gly
           35                  40                  45

Ala Tyr Pro Ile Ile Gly Asn Ala Leu Gln Phe Lys Thr Asn Ala Gly
 50                  55                  60

Asp Phe Phe Asn Gln Ile Ile Glu Gly Thr Asn Glu Asn Arg His Leu
 65                  70                  75                  80

Pro Leu Ala Lys Val Trp Val Gly Pro Val Pro Phe Leu Ile Leu Tyr
                 85                  90                  95

His Ala Glu Asn Ile Glu Val Val Leu Ser Asn Ser Arg His Leu Asp
             100                 105                 110

Lys Ser Tyr Ser Tyr Arg Phe Leu His Pro Trp Leu Gly Thr Gly Leu
             115                 120                 125

Leu Thr Ser Thr Gly Glu Lys Trp Arg Asn Arg Arg Lys Met Leu Thr
     130                 135                 140

Pro Thr Phe His Phe Ser Ile Leu Ser Asp Phe Leu Glu Val Met Asn
145                 150                 155                 160

Glu Gln Thr Asp Ile Leu Ile Gln Lys Met Gln Lys Leu Glu Asp Gly
                 165                 170                 175

Glu Pro Phe Asn Cys Phe Asn Phe Ile Thr Leu Cys Ala Leu Asp Ile
             180                 185                 190

Ile Cys Glu Thr Ala Met Gly Lys Lys Ile Tyr Ala Gln Ser Asn Ala
     195                 200                 205

Asp Ser Glu Tyr Val Gln Ser Val Tyr Lys Met Ser Asp Ile Ile Thr
     210                 215                 220

Lys Arg Gln Arg Ala Pro Trp Leu Trp Pro Asp Trp Ile Tyr Asn Lys
225                 230                 235                 240

Leu Lys Glu Gly Lys Glu His Ala Lys Arg Leu Lys Ile Leu His Ser
                 245                 250                 255

Phe Thr Ala Asn Val Ile Arg Glu Arg Ala Glu Phe Met Ser Ser Glu
             260                 265                 270

Pro Asp Ser Asp Ser Asp Gln Gly Glu Arg Lys Arg Gln Ala Phe Leu
     275                 280                 285

Asp Met Leu Leu Lys Thr Thr Tyr Glu Asn Gly Gln Lys Leu Ser His
     290                 295                 300

Glu Asp Ile Gln Glu Glu Val Asp Thr Phe Met Phe Glu Gly His Asp
305                 310                 315                 320

Thr Thr Ala Ala Ser Met Asn Trp Ala Leu His Leu Ile Gly Ser His
                 325                 330                 335

Pro Glu Val Gln Lys Ala Val Gln Ala Glu Leu Gln Glu Val Phe Gly
             340                 345                 350

Ser Ser Glu Arg His Val Gly Val Glu Asp Leu Lys Lys Leu Arg Tyr
     355                 360                 365

Leu Glu Cys Val Ile Lys Glu Ser Leu Arg Ile Phe Pro Ser Val Pro
     370                 375                 380

Leu Phe Ala Arg Ser Ile Cys Glu Ala Cys His Ile Asn Gly Phe Lys
385                 390                 395                 400

Val Pro Lys Gly Val Asn Ala Val Ile Ile Pro Tyr Ala Leu His Arg
                 405                 410                 415

Asp Pro Arg Tyr Phe Pro Glu Pro Glu Glu Phe Gln Pro Glu Arg Phe
             420                 425                 430

Met Pro Glu Asn Ser Lys Gly Arg His Pro Tyr Ala Tyr Ile Pro Phe
             435                 440                 445

Ser Ala Gly Pro Arg Asn Cys Ile Gly Gln Arg Phe Ala Met Met Glu

-continued

```
                450                 455                 460
Glu Lys Val Val Leu Ala Thr Ile Leu Arg His Phe Asp Val Glu Ala
465                 470                 475                 480

Cys Gln Ser Arg Glu Glu Leu Arg Pro Leu Gly Glu Leu Ile Leu Arg
                485                 490                 495

Pro Glu Lys Gly Ile Trp Ile Lys Leu Gln Arg Arg Ser Lys
                500                 505                 510

<210> SEQ ID NO 41
<211> LENGTH: 518
<212> TYPE: PRT
<213> ORGANISM: Arabidopsis thaliana

<400> SEQUENCE: 41

Met Leu Leu Thr Ile Leu Lys Ser Leu Leu Val Ile Phe Val Thr Thr
1               5                   10                  15

Ile Leu Arg Val Leu Tyr Asp Thr Ile Ser Cys Tyr Trp Leu Thr Pro
                20                  25                  30

Arg Arg Ile Lys Lys Ile Met Glu Gln Gln Gly Val Thr Gly Pro Lys
            35                  40                  45

Pro Arg Pro Leu Thr Gly Asn Ile Leu Glu Ile Ser Ala Met Val Ser
        50                  55                  60

Gln Ser Ala Ser Lys Asp Cys Asp Ser Ile His His Asp Ile Val Gly
65                  70                  75                  80

Arg Leu Leu Pro His Tyr Val Ala Trp Ser Lys Gln Tyr Gly Lys Arg
                85                  90                  95

Phe Ile Val Trp Asn Gly Thr Asp Pro Arg Leu Cys Leu Thr Glu Thr
            100                 105                 110

Glu Leu Ile Lys Glu Leu Leu Met Lys His Asn Gly Val Ser Gly Arg
        115                 120                 125

Ser Trp Leu Gln Gln Gln Gly Thr Lys Asn Phe Ile Gly Arg Gly Leu
130                 135                 140

Leu Met Ala Asn Gly Gln Asp Trp His His Gln Arg His Leu Ala Ala
145                 150                 155                 160

Pro Ala Phe Thr Gly Glu Arg Leu Lys Gly Tyr Ala Arg His Met Val
                165                 170                 175

Glu Cys Thr Ser Lys Leu Val Glu Arg Leu Arg Lys Glu Val Gly Glu
            180                 185                 190

Gly Ala Asn Glu Val Glu Ile Gly Glu Glu Met His Lys Leu Thr Ala
        195                 200                 205

Asp Ile Ile Ser Arg Thr Lys Phe Gly Ser Ser Phe Glu Lys Gly Lys
210                 215                 220

Glu Leu Phe Asn His Leu Thr Val Leu Gln Arg Arg Cys Ala Gln Ala
225                 230                 235                 240

Thr Arg His Leu Cys Phe Pro Gly Ser Arg Phe Leu Pro Ser Lys Tyr
                245                 250                 255

Asn Arg Glu Ile Lys Ser Leu Lys Lys Glu Val Glu Arg Leu Leu Ile
            260                 265                 270

Glu Ile Ile Gln Ser Arg Arg Asp Cys Ala Glu Met Gly Arg Ser Ser
        275                 280                 285

Thr His Gly Asp Asp Leu Leu Gly Leu Leu Leu Asn Glu Met Asp Ile
        290                 295                 300

Asp Lys Asn Asn Asn Asn Asn Asn Asn Leu Gln Leu Ile Met Asp
305                 310                 315                 320

Glu Cys Lys Thr Phe Phe Phe Ala Gly His Glu Thr Thr Ala Leu Leu
```

```
                325                 330                 335
Leu Thr Trp Thr Thr Met Leu Leu Ala Asp Asn Pro Thr Trp Gln Glu
            340                 345                 350

Lys Val Arg Glu Glu Val Arg Glu Val Phe Gly Arg Asn Gly Leu Pro
        355                 360                 365

Ser Val Asp Gln Leu Ser Lys Leu Thr Ser Leu Ser Lys Val Ile Asn
    370                 375                 380

Glu Ser Leu Arg Leu Tyr Pro Pro Ala Thr Leu Leu Pro Arg Met Ala
385                 390                 395                 400

Phe Glu Asp Leu Lys Leu Gly Asp Leu Thr Ile Pro Lys Gly Leu Ser
                405                 410                 415

Ile Trp Ile Pro Val Leu Ala Ile His His Ser Glu Glu Leu Trp Gly
            420                 425                 430

Lys Asp Ala Asn Gln Phe Asn Pro Glu Arg Phe Gly Arg Pro Arg Phe
        435                 440                 445

Ala Ser Gly Arg His Phe Ile Pro Phe Ala Ala Gly Pro Arg Asn Cys
    450                 455                 460

Ile Gly Gln Gln Phe Ala Leu Met Glu Ala Lys Ile Ile Leu Ala Thr
465                 470                 475                 480

Leu Ile Ser Lys Phe Asn Phe Thr Ile Ser Lys Asn Tyr Arg His Ala
                485                 490                 495

Pro Ile Val Val Leu Thr Ile Lys Pro Lys Tyr Gly Val Gln Val Ile
            500                 505                 510

Leu Lys Pro Leu Val Ser
        515

<210> SEQ ID NO 42
<211> LENGTH: 576
<212> TYPE: PRT
<213> ORGANISM: Arabidopsis thaliana

<400> SEQUENCE: 42

Met Ala Phe Pro Ala Ala Ala Thr Tyr Pro Thr His Phe Gln Gly Gly
1               5                   10                  15

Ala Leu His Leu Gly Arg Thr Asp His Cys Leu Phe Gly Phe Tyr Pro
                20                  25                  30

Gln Thr Ile Ser Ser Val Asn Ser Arg Arg Ala Ser Val Ser Ile Lys
            35                  40                  45

Cys Gln Ser Thr Glu Pro Lys Thr Asn Gly Asn Ile Leu Asp Asn Ala
    50                  55                  60

Ser Asn Leu Leu Thr Asn Phe Leu Ser Gly Gly Ser Leu Gly Ser Met
65                  70                  75                  80

Pro Thr Ala Glu Gly Ser Val Ser Asp Leu Phe Gly Lys Pro Leu Phe
                85                  90                  95

Leu Ser Leu Tyr Asp Trp Phe Leu Glu His Gly Gly Ile Tyr Lys Leu
                100                 105                 110

Ala Phe Gly Pro Lys Ala Phe Val Val Ile Ser Asp Pro Ile Ile Ala
            115                 120                 125

Arg His Val Leu Arg Glu Asn Ala Phe Ser Tyr Asp Lys Gly Val Leu
    130                 135                 140

Ala Glu Ile Leu Glu Pro Ile Met Gly Lys Gly Leu Ile Pro Ala Asp
145                 150                 155                 160

Leu Asp Thr Trp Lys Leu Arg Arg Arg Ala Ile Thr Pro Ala Phe His
                165                 170                 175

Lys Leu Tyr Leu Glu Ala Met Val Lys Val Phe Ser Asp Cys Ser Glu
```

```
                180              185              190
Lys Met Ile Leu Lys Ser Glu Lys Leu Ile Arg Glu Lys Glu Thr Ser
            195              200              205
Ser Gly Glu Asp Thr Ile Glu Leu Asp Leu Glu Ala Glu Phe Ser Ser
210              215              220
Leu Ala Leu Asp Ile Ile Gly Leu Ser Val Phe Asn Tyr Asp Phe Gly
225              230              235              240
Ser Val Thr Lys Glu Ser Pro Val Ile Lys Ala Val Tyr Gly Thr Leu
            245              250              255
Phe Glu Ala Glu His Arg Ser Thr Phe Tyr Phe Pro Tyr Trp Asn Phe
            260              265              270
Pro Pro Ala Arg Trp Ile Val Pro Arg Gln Arg Lys Phe Gln Ser Asp
            275              280              285
Leu Lys Ile Ile Asn Asp Cys Leu Asp Gly Leu Ile Gln Asn Ala Lys
            290              295              300
Glu Thr Arg Gln Glu Thr Asp Val Glu Lys Leu Gln Glu Arg Asp Tyr
305              310              315              320
Thr Asn Leu Lys Asp Ala Ser Leu Leu Arg Phe Leu Val Asp Met Arg
                325              330              335
Gly Val Asp Ile Asp Asp Arg Gln Leu Arg Asp Asp Leu Met Thr Met
                340              345              350
Leu Ile Ala Gly His Glu Thr Thr Ala Ala Val Leu Thr Trp Ala Val
                355              360              365
Phe Leu Leu Ser Gln Asn Pro Glu Lys Ile Arg Lys Ala Gln Ala Glu
            370              375              380
Ile Asp Ala Val Leu Gly Gln Gly Pro Pro Thr Tyr Glu Ser Met Lys
385              390              395              400
Lys Leu Glu Tyr Ile Arg Leu Ile Val Val Glu Val Leu Arg Leu Phe
                405              410              415
Pro Gln Pro Pro Leu Leu Ile Arg Arg Thr Leu Lys Pro Glu Thr Leu
            420              425              430
Pro Gly Gly His Lys Gly Glu Lys Glu Gly His Lys Val Pro Lys Gly
            435              440              445
Thr Asp Ile Phe Ile Ser Val Tyr Asn Leu His Arg Ser Pro Tyr Phe
            450              455              460
Trp Asp Asn Pro His Asp Phe Glu Pro Glu Arg Phe Leu Arg Thr Lys
465              470              475              480
Glu Ser Asn Gly Ile Glu Gly Trp Ala Gly Phe Asp Pro Ser Arg Ser
            485              490              495
Pro Gly Ala Leu Tyr Pro Asn Glu Ile Ile Ala Asp Phe Ala Phe Leu
            500              505              510
Pro Phe Gly Gly Gly Pro Arg Lys Cys Ile Gly Asp Gln Phe Ala Leu
            515              520              525
Met Glu Ser Thr Val Ala Leu Ala Met Leu Phe Gln Lys Phe Asp Val
            530              535              540
Glu Leu Arg Gly Thr Pro Glu Ser Val Glu Leu Val Ser Gly Ala Thr
545              550              555              560
Ile His Ala Lys Asn Gly Met Trp Cys Lys Leu Lys Arg Arg Ser Lys
                565              570              575

<210> SEQ ID NO 43
<211> LENGTH: 534
<212> TYPE: PRT
<213> ORGANISM: Oryza sativa
```

<400> SEQUENCE: 43

```
Met Ala Ala Ala Val Leu Val Ala Ile Ala Leu Pro Val Ser Leu Ala
1               5                   10                  15
Leu Leu Leu Val Ala Lys Ala Val Trp Val Thr Val Ser Cys Tyr Tyr
            20                  25                  30
Leu Thr Pro Ala Arg Ile Arg Arg Val Leu Ala Ser Gln Gly Val Arg
        35                  40                  45
Gly Pro Pro Arg Pro Leu Val Gly Asn Leu Arg Asp Val Ser Ala
    50                  55                  60
Leu Val Ala Glu Ser Thr Ala Ala Asp Met Ala Ser Leu Ser His Asp
65                  70                  75                  80
Ile Val Ala Arg Leu Leu Pro His Tyr Val Leu Trp Ser Asn Thr Tyr
                85                  90                  95
Gly Arg Arg Phe Val Tyr Trp Tyr Gly Ser Glu Pro Arg Val Cys Val
            100                 105                 110
Thr Glu Ala Gly Met Val Arg Glu Leu Leu Ser Ser Arg His Ala His
        115                 120                 125
Val Thr Gly Lys Ser Trp Leu Gln Arg Gln Gly Ala Lys His Phe Ile
130                 135                 140
Gly Arg Gly Leu Leu Met Ala Asn Gly Ala Thr Trp Ser His Gln Arg
145                 150                 155                 160
His Val Val Ala Pro Ala Phe Met Ala Asp Arg Leu Lys Gly Arg Val
                165                 170                 175
Gly His Met Val Glu Cys Thr Arg Gln Thr Val Arg Ala Leu Arg Glu
            180                 185                 190
Ala Val Ala Arg Ser Gly Asn Glu Val Glu Ile Gly Ala His Met Ala
        195                 200                 205
Arg Leu Ala Gly Asp Val Ile Ala Arg Thr Glu Phe Asp Thr Ser Tyr
210                 215                 220
Glu Thr Gly Lys Arg Ile Phe Leu Leu Ile Glu Glu Leu Gln Arg Leu
225                 230                 235                 240
Thr Ala Arg Ser Ser Arg Tyr Leu Trp Val Pro Gly Ser Gln Tyr Phe
                245                 250                 255
Pro Ser Lys Tyr Arg Arg Glu Ile Lys Arg Leu Asn Gly Glu Leu Glu
            260                 265                 270
Arg Leu Leu Lys Glu Ser Ile Asp Arg Ser Arg Glu Ile Ala Asp Glu
        275                 280                 285
Gly Arg Thr Pro Ser Ala Ser Pro Cys Gly Arg Gly Leu Leu Gly Met
290                 295                 300
Leu Leu Ala Glu Met Glu Lys Lys Glu Ala Gly Gly Asn Gly Gly Gly
305                 310                 315                 320
Glu Val Gly Tyr Asp Ala Gln Met Met Ile Asp Glu Cys Lys Thr Phe
                325                 330                 335
Phe Phe Ala Gly His Glu Thr Ser Ala Leu Leu Leu Thr Trp Ala Ile
            340                 345                 350
Met Leu Leu Ala Thr His Pro Ala Trp Gln Asp Lys Ala Arg Ala Glu
        355                 360                 365
Val Ala Ala Val Cys Gly Gly Gly Ala Pro Ser Pro Asp Ser Leu Pro
370                 375                 380
Lys Leu Ala Val Leu Gln Met Val Ile Asn Glu Thr Leu Arg Leu Tyr
385                 390                 395                 400
Pro Pro Ala Thr Leu Leu Pro Arg Met Ala Phe Glu Asp Ile Glu Leu
                405                 410                 415
```

```
Gly Gly Gly Ala Leu Arg Val Pro Ser Gly Ala Ser Val Trp Ile Pro
            420                 425                 430

Val Leu Ala Ile His His Asp Glu Gly Ala Trp Gly Arg Asp Ala His
            435                 440                 445

Glu Phe Arg Pro Asp Arg Phe Ala Pro Gly Arg Pro Arg Pro Pro Ala
450                 455                 460

Gly Ala Phe Leu Pro Phe Ala Ala Gly Pro Arg Asn Cys Val Gly Gln
465                 470                 475                 480

Ala Tyr Ala Met Val Glu Ala Lys Val Ala Leu Ala Met Leu Leu Ser
                485                 490                 495

Ser Phe Arg Phe Ala Ile Ser Asp Glu Tyr Arg His Ala Pro Val Asn
            500                 505                 510

Val Leu Thr Leu Arg Pro Arg His Gly Val Pro Val Arg Leu Leu Pro
            515                 520                 525

Leu Pro Pro Pro Arg Pro
    530

<210> SEQ ID NO 44
<211> LENGTH: 519
<212> TYPE: PRT
<213> ORGANISM: Oryza sativa

<400> SEQUENCE: 44

Met Ala Val Gly Leu Leu Val Val Ala Tyr Leu Tyr Glu Pro Tyr Arg
1               5                   10                  15

Lys Val Trp His Val Pro Gly Pro Val Pro Val Pro Leu Ile Gly His
            20                  25                  30

Leu His Leu Leu Ala Met His Gly Pro Asp Val Phe Ser Val Leu Ala
            35                  40                  45

Arg Lys His Gly Pro Val Phe Arg Phe His Met Gly Arg Gln Pro Leu
        50                  55                  60

Ile Ile Val Ala Asp Ala Glu Leu Cys Lys Glu Val Gly Val Lys Lys
65                  70                  75                  80

Phe Lys Ser Ile Pro Asn Arg Ser Met Pro Ser Pro Ile Ala Asn Ser
                85                  90                  95

Pro Ile His Lys Lys Gly Leu Phe Phe Ile Arg Gly Pro Arg Trp Thr
            100                 105                 110

Ser Met Arg Asn Met Ile Ile Ser Ile Tyr Gln Pro Ser His Leu Ala
        115                 120                 125

Ser Leu Ile Pro Thr Met Glu Ser Cys Ile Gln Arg Ala Ser Lys Asn
    130                 135                 140

Leu Asp Gly Gln Lys Glu Ile Thr Phe Ser Asp Leu Ser Leu Ser Leu
145                 150                 155                 160

Ala Thr Asp Val Ile Gly Leu Ala Ala Phe Gly Thr Asp Phe Gly Leu
                165                 170                 175

Ser Lys Val Pro Val Thr Pro Asp Asp Ser Asn Ile Asp Lys Ile Ala
            180                 185                 190

Ala Asp Thr Ser Val Glu Ala Lys Ala Ser Ser Glu Phe Ile Lys Met
        195                 200                 205

His Met His Ala Thr Thr Ser Leu Lys Met Asp Leu Ser Gly Ser Leu
    210                 215                 220

Ser Ile Leu Val Gly Met Leu Leu Pro Phe Leu Gln Glu Pro Phe Arg
225                 230                 235                 240

Gln Val Leu Lys Arg Ile Pro Gly Met Gly Asp Tyr Lys Ile Asp Arg
                245                 250                 255
```

Val Asn Arg Ala Leu Lys Thr His Met Asp Ser Ile Val Ala Glu Arg
            260                 265                 270

Glu Ala Ala Met Glu His Asp Leu Ala Ser Gln Gln Arg Lys Asp
        275                 280                 285

Phe Leu Ser Val Val Leu Thr Ala Arg Glu Ser Asn Lys Ser Ser Arg
290                 295                 300

Glu Leu Leu Thr Pro Asp Tyr Ile Ser Ala Leu Thr Tyr Glu His Leu
305                 310                 315                 320

Leu Ala Gly Ser Thr Thr Ala Phe Thr Leu Ser Thr Val Leu Tyr
                325                 330                 335

Leu Val Ala Lys His Pro Glu Val Glu Lys Leu Leu Lys Glu Ile
            340                 345                 350

Asp Ala Phe Gly Pro Arg Asp Arg Val Pro Met Ala Asp Asp Leu Gln
            355                 360                 365

Thr Lys Phe Pro Tyr Leu Asp Gln Val Val Lys Glu Ser Met Arg Phe
    370                 375                 380

Tyr Met Met Ser Pro Leu Leu Ala Arg Glu Thr Leu Glu Gln Val Glu
385                 390                 395                 400

Ile Gly Gly Tyr Val Leu Pro Lys Gly Thr Trp Val Trp Leu Ala Pro
                405                 410                 415

Gly Val Leu Ala Lys Asp Pro Lys Asn Phe Pro Glu Pro Glu Ile Phe
            420                 425                 430

Arg Pro Glu Arg Phe Asp Pro Asn Gly Glu Glu Arg Arg His
            435                 440                 445

Leu Tyr Ala Phe Ile Pro Phe Gly Ile Gly Pro Arg Val Cys Ile Gly
    450                 455                 460

Gln Lys Phe Ser Ile Gln Glu Ile Lys Leu Ser Val Ile His Leu Tyr
465                 470                 475                 480

Arg His Tyr Val Phe Arg His Ser Pro Ser Met Glu Ser Pro Leu Glu
                485                 490                 495

Phe Gln Phe Ala Ile Ile Cys Asp Phe Lys Tyr Gly Val Lys Leu Gln
            500                 505                 510

Ala Ile Lys Arg His His Ala
            515

<210> SEQ ID NO 45
<211> LENGTH: 571
<212> TYPE: PRT
<213> ORGANISM: Oryza sativa

<400> SEQUENCE: 45

Met Ala Ile Thr Ala Ala Thr Ala Ala Ala Ala Thr Pro His Pro
1               5                   10                  15

Trp Gln Ala Asp Ala Ser Pro Arg Arg His Ala Ala Cys Pro Ala Leu
                20                  25                  30

Arg Gly Arg Arg Arg Leu Pro Val Val Arg Cys Gln Ser Ser Ser Val
            35                  40                  45

Asp Asp Lys Pro Lys Ser Lys Arg Gly Leu Leu Asp Asn Ala Ser Asn
    50                  55                  60

Leu Leu Thr Asn Leu Leu Ser Gly Gly Ser Leu Gly Ala Met Pro Val
65                  70                  75                  80

Ala Glu Gly Ala Val Thr Asp Leu Phe Gly Arg Pro Leu Phe Phe Ser
                85                  90                  95

Leu Tyr Asp Trp Phe Leu Glu His Gly Ser Val Tyr Lys Leu Ala Phe
            100                 105                 110

```
Gly Pro Lys Ala Phe Val Val Ser Asp Pro Ile Val Ala Arg His
        115                 120                 125

Ile Leu Arg Glu Asn Ala Phe Cys Tyr Asp Lys Gly Val Leu Ala Glu
145     130                 135                 140

Ile Leu Lys Pro Ile Met Gly Lys Gly Leu Ile Pro Ala Asp Leu Asp
145                 150                 155                 160

Thr Trp Lys Gln Arg Arg Lys Val Ile Thr Pro Gly Phe His Ala Leu
                165                 170                 175

Phe Ile Glu Ala Met Val Gly Val Phe Thr Lys Cys Ser Glu Arg Thr
                180                 185                 190

Ile Phe Lys Leu Glu Glu Leu Ile Glu Arg Gly Glu His Gly Glu Lys
                195                 200                 205

Tyr Thr Ile Val Asp Leu Glu Ala Glu Phe Ser Asn Leu Ala Leu Asp
    210                 215                 220

Ile Ile Gly Leu Gly Val Phe Asn Phe Asp Phe Asp Ser Val Thr Lys
225                 230                 235                 240

Glu Ser Pro Val Ile Lys Ala Val Tyr Gly Thr Leu Phe Glu Ala Glu
                245                 250                 255

His Arg Ser Thr Phe Tyr Ile Pro Tyr Trp Asn Leu Pro Leu Thr Arg
                260                 265                 270

Trp Ile Val Pro Arg Gln Arg Lys Phe His Ser Asp Leu Lys Val Ile
            275                 280                 285

Asn Asp Cys Leu Asp Ser Leu Ile Lys Asn Ala Lys Glu Thr Arg Gln
            290                 295                 300

Glu Ala Asp Val Glu Lys Leu Gln Gln Arg Asp Tyr Ser Ser Leu Lys
305                 310                 315                 320

Asp Ala Ser Leu Leu Arg Phe Leu Val Asp Met Arg Gly Ala Asp Val
                325                 330                 335

Asp Asp Arg Gln Leu Arg Asp Asp Leu Met Thr Met Leu Ile Ala Gly
            340                 345                 350

His Glu Thr Thr Ala Ala Val Leu Thr Trp Ser Val Phe Leu Leu Ala
            355                 360                 365

Gln Asn Pro Ser Lys Met Arg Lys Ala Gln Ala Glu Val Asp Ser Val
    370                 375                 380

Leu Ser Asn Glu Thr Ile Asn Val Asp Gln Leu Lys Lys Leu Glu Tyr
385                 390                 395                 400

Ile Arg Leu Ile Ile Val Glu Ala Leu Arg Leu Tyr Pro Gln Pro Pro
                405                 410                 415

Leu Leu Ile Arg Arg Ala Leu Arg Pro Asp Lys Leu Pro Gly Gly Tyr
                420                 425                 430

Asn Gly Ala Lys Glu Gly Tyr Glu Ile Pro Ala Gly Thr Asp Ile Phe
            435                 440                 445

Leu Ser Ile Tyr Asn Leu His Arg Ser Pro Tyr Phe Trp Asp Arg Pro
    450                 455                 460

Asp Glu Phe Glu Pro Glu Arg Phe Ser Val Pro Lys Lys Asp Glu Ser
465                 470                 475                 480

Ile Glu Gly Trp Ala Gly Phe Asp Pro Asp Arg Ser Pro Gly Ala Met
                485                 490                 495

Tyr Pro Asn Glu Ile Leu Ala Asp Phe Ala Phe Leu Pro Phe Gly Gly
                500                 505                 510

Gly Pro Arg Lys Cys Val Gly Asp Gln Phe Ala Leu Leu Glu Ser Thr
            515                 520                 525

Val Ala Leu Ala Leu Leu Leu Gln Lys Phe Asp Val Glu Leu Arg Gly
530                 535                 540
```

Ser Pro Asp Glu Val Glu Met Val Thr Gly Ala Thr Ile His Thr Lys
545                 550                 555                 560

Ser Gly Leu Trp Cys Arg Val Arg Arg Arg Thr
            565                 570

<210> SEQ ID NO 46
<211> LENGTH: 2108
<212> TYPE: DNA
<213> ORGANISM: Drosophila melanogaster

<400> SEQUENCE: 46

```
cttcggataa gctgttcacg cgattgagag gatccgttcg gtgaaaaaaa caaaaattta      60
aacaaagcaa atcaaatcga aaagaattat aaattaaatt aaagaaaaaa aaataataga     120
ataaaaatga cagcggatac attggtgctg gaaacaatgg atagtgcaaa aaattcaact     180
gcgggacccg caaccgtatt gaacccaatt tggactgctc ttttgggtat tgcagtggtt     240
gtgagtttgt acgaaatatg gctaaggaat accaggaaat ataaattaac ggcaaatatg     300
ccaaacccac ctatgctgcc actcatcgga aatggccatt tggtggccca tttgacaaat     360
gccgaaatcc ttgcccgtgg cattggttac atgcaaacct atggtggtgc catgcgtggc     420
ttttgggtc ccatgttggt tgtgttcctc tggaacgctc ccgatattga attgattctc     480
agtacccaca cccatttgga gaagtcaatt gaatatcgtt tcttcaaacc ctggtttggt     540
gatggtctac ttatttcgaa tggtcaccat ggcaacatc atcgcaaaat gattgctcca     600
acattccatc aaagcatttt gaagagtttc gtgccagcct ttgtgcaaca ctccaagaag     660
gtggtggaac gtatggccaa ggaattgggc aaggaattcg atgtccatga ctatatgtca     720
cagaccactg tggaaatttt gctctccact gccatgggtg ttaagaaggt gcccgaggac     780
aacaagagtt ggaatatgc caaggctgtg gtggacatgt gcgacatcat tcacaagcgc     840
caattgaaat tcttctatcg catggatgcc ctctacaatt tgagcagcat gagtgagaag     900
ggcaagaaga tgatggacat tattttgggc atgacccgta aagtggtgac ggaacgtcaa     960
cagaatttca atgccgaatc gcgtgccatt gtcgaggagg atgatgaaat tagcaagcag    1020
aagcaacagg ccaagaagaa ggagggtttg cgtgatgatt tggatgacat tgatgaaaat    1080
gatgtgggtg ccaagaaacg tttggctctg ctggatgcca tgatggccat gtccaagaac    1140
cccgatgttg agtggaccga caaggatgtc atggatgaag tcaacaccat tatgtttgag    1200
ggccacgata ccacctcagc tggttccagt tttgtcctct gcatgttggg catctacaag    1260
gatatccaag agaaagtcct ggccgaacaa aaggccatct ttggtgacaa cttcctgcgc    1320
gactgtacct tgccgatac atggaaatg aaatacctgg aacgtgtgat tatggagact    1380
ttgcgtttgt atccaccagt accccttatt gcccgtcgtg ctgagttcga tgtaaaattg    1440
gcttccggtc cctacacaat tcccaagggc acaacagtgg tgattgccca atttgctgtg    1500
catcgcaatc cccaatactt ccccaatccc gagaaattcg atcctgacaa tttcctaccc    1560
gaacgtatgg ccaatcgtca ttactacagt ttcattccct tcagtgccgg ccccagaagt    1620
tgcgttggcc gcaaatatgc catgctgaaa ttaaggtcc tgctctccac cattattcgt    1680
aactattcgg tgcagagcaa ccaacaggag aaggacttta agttgcaggc cgatattatc    1740
ctaaagattg aaaatggttt caatatcatg ttgaaccgac gacccgaagc catgaaagct    1800
atgtaaagta aagtagagat gagtgtgtaa agaagttttt tgtcccaact atcctaagaa    1860
tgacccgtat cctgtatgt ggtttccatt ttattgataa gtaaagaag aaagaaacta    1920
acccccgca ttataccaaa taataagaaa taacgaaact actaaccgac gtgagagtgt    1980
```

| | |
|---|---:|
| taagtttat cctattgtta ttgactaaaa tgtatgttaa gattttttt ttataaattt | 2040 |
| tattgttttt gaagaaaaca caaaaatttt aaaaaaaaat aataaagagc atgccagttt | 2100 |
| aaaactgt | 2108 |

<210> SEQ ID NO 47
<211> LENGTH: 1680
<212> TYPE: DNA
<213> ORGANISM: Musca domestica

<400> SEQUENCE: 47

| | |
|---|---:|
| atgacagcgg atacattggt gctggaaaca atggatagtg caaaaaattc aactgcggga | 60 |
| cccgcaaccg tattgaaccc aatttggact gctcttttgg gtattgcagt ggttgtgagt | 120 |
| ttgtacgaaa tatggctaag gaataccagg aaatataaat taacggcaaa tatgccaaac | 180 |
| ccacctatgc tgccactcat cggaaatggc catttggtgg cccatttgac aaatgccgaa | 240 |
| atccttgccc gtggcattgg ttacatgcaa acctatggtg gtgccatgcg tggcttttg | 300 |
| ggtcccatgt tggttgtgtt cctctggaac gctcccgata ttgaattgat tctcagtacc | 360 |
| cacacccatt tggagaagtc aattgaatat cgtttcttca aaccctggtt tggtgatggt | 420 |
| ctacttattt cgaatggtca ccattggcaa catcatcgca aaatgattgc tccaacattc | 480 |
| catcaaagca ttttgaagag tttcgtgcca gcctttgtgc aacactccaa gaaggtggtg | 540 |
| gaacgtatgg ccaaggaatt gggcaaggaa ttcgatgtcc atgactatat gtcacagacc | 600 |
| actgtggaaa ttttgctctc cactgccatg ggtgttaaga aggtgcccga ggacaacaag | 660 |
| agtttggaat atgccaaggc tgtggtggac atgtgcgaca tcattcacaa gcgccaattg | 720 |
| aaattcttct atcgcatgga tgccctctac aatttgagca gcatgagtga aagggcaag | 780 |
| aagatgatgg acattatttt gggcatgacc cgtaaagtgg tgacggaacg tcaacagaat | 840 |
| ttcaatgccg aatcgcgtgc cattgtcgag gaggatgatg aaattagcaa gcagaagcaa | 900 |
| caggccaaga agaaggaggg tttgcgtgat gatttggatg acattgatga aaatgatgtg | 960 |
| ggtgccaaga acgtttggc tctgctggat gccatgatgg ccatgtccaa gaaccccgat | 1020 |
| gttgagtgga ccgacaagga tgtcatggat gaagtcaaca ccattatgtt tgagggccac | 1080 |
| gataccacct cagctggttc cagttttgtc ctctgcatgt tgggcatcta caaggatatc | 1140 |
| caagagaaag tcctggccga acaaaaggcc atctttggtg acaacttcct gcgcgactgt | 1200 |
| acctttgccg ataccatgga aatgaaatac ctggaacgtg tgattatgga gactttgcgt | 1260 |
| ttgtatccac cagtaccct tattgcccgt cgtgctgagt tcgatgtaaa attggcttcc | 1320 |
| ggtccctaca caattcccaa gggcacaaca gtggtgattg cccaatttgc tgtgcatcgc | 1380 |
| aatccccaat acttccccaa tcccgagaaa ttcgatcctg acaatttcct acccgaacgt | 1440 |
| atggccaatc gtcattacta cagtttcatt cccttcagtg ccggcccag aagttgcgtt | 1500 |
| ggccgcaaat atgccatgct gaaattaaag gtcctgctct ccaccattat tcgtaactat | 1560 |
| tcggtgcaga gcaaccaaca ggagaaggac tttaagttgc aggccgatat tatcctaaag | 1620 |
| attgaaaatg gtttcaatat catgttgaac cgacgacccg aagccatgaa agctatgtaa | 1680 |

<210> SEQ ID NO 48
<211> LENGTH: 2285
<212> TYPE: DNA
<213> ORGANISM: Musca domestica

<400> SEQUENCE: 48

| | |
|---|---:|
| acagttgagc actggcggct gatatagcaa cagtgccatc ttcagaagac aaaaaggatt | 60 |

```
tgcaccagag gaccagggat caggagcaaa gaagcaacag caaccatggc agtggaagta    120
gttcaggaga cgctgcaaca agcggcgtcc agttcgtcga cgacggtcct gggattcagt    180
cctatgttaa ccaccttagt gggcaccctg gtggccatgg cattgtacga gtattggcgc    240
aggaatagcc gggaataccg catggttgcc aatataccat ccccaccgga gttgcctatt    300
ttgggacagg ctcatgtggc cgccggcttg agcaatgccg agatcctggc cgttggcttg    360
ggttacctca acaagtacgg agaaaccatg aaggcctggt tgggcaacgt cctgttggtg    420
tttctaacca atcccagtga catcgagttg atcctgagtg ggcaccagca cttgaccaag    480
gcggaggagt atcgctactt caagccctgg ttcggtgatg gtctactgat cagcaatgga    540
catcattggc gtcatcatcg taagatgatt gcccccacct tccaccagag catcttgaag    600
agcttcgtgc ctacatttgt ggatcactca aaggcggtag ttgccaggat gggcttagaa    660
gcgggcaaat cctttgatgt tcatgactat atgtcgcaga ccacggttga catcctgttg    720
tctaccgcca tgggtgtgaa gaagcttccg gagggtaaca agagtttcga atacgcccaa    780
gccgtcgtcg acatgtgtga tatcatacat aagaggcagg ttaaattact gtaccgcctg    840
gattccatct acaagtttac taagcttcgc gagaagggcg atcgcatgat gaacatcatc    900
ttgggtatga ccagcaaggt ggtcaaggat cgtaaggaga acttccaaga ggagtcacgt    960
gcgattgttg aggagatttc tacacctgtt gccagcactc ccgcttccaa gaaggagggt   1020
cttcgcgatg atctggatga tatcgatgaa aatgatgtgg gcgccaagag gcgattggct   1080
cttctagatg ccatggtgga aatggctaag aaccccgata tcgagtggaa cgagaaggac   1140
atcatggatg aggtgaatac aattatgttt gagggccacg ataccacctc ggcgggatct   1200
agtttcgccc tctgcatgat gggaatccac aaggacatcc aggctaaagt cttcgccgaa   1260
cagaaggcca tcttcgggga taatatgctg agggattgca cctttgccga taccatggag   1320
atgaaatatt tggagcgcgt aattttagag actttgaggt tgtacccacc agtaccactt   1380
atcgccaggc gtctggacta cgacctgaag ttggccagtg gtccgtacac ggttcccaag   1440
ggcactacgg tcatcgtgct gcagtactgc gtgcacagac gtccagacat ctaccccaat   1500
cccaccaaat tcgatccgga caacttccta cccgagagga tggccaacag gcattactac   1560
tccttcattc cctttagcgc tggacccaga agctgtgtgg gccgcaagta cgccatgctg   1620
aagctaaagg tcctgctatc caccatcgtg aggaactata ttgtccactc caccgacacg   1680
gaggcagatt tcaagctgca ggctgacatc atcctaaagc ttgagaatgg attcaatgtc   1740
tcgttggaga agcgtcagta cgccacggtg gcctagaatc cagaaatcta ggaccccgac   1800
tacacacacg caaccccgaa cccgaaaccg gaatccagcc ctgtatatag atgatgaata   1860
ccgatgaata tcccaaaccg aaaacttgat gacgaactta taaatctaaa acaccgaata   1920
agaacccaac gcacaagcca gccagagagt caattaattt ttctttcgtt ttttaactcg   1980 ttactttttat atttgattaa tacctttttg tttgttggtc tttagcgagt ggtgccccta   2040
tataatgtat acgtatatac tatatatcct tttaaccaac tattcaacgc aactgtttgt   2100
gctcttcacc tttttagtac tcctactttt accactatct atactttttt ttcgtagcca   2160
tgtagtgtga tttttttttct ttattctagt atttattaag tcaaatggtt taaacgaaac   2220
ccaaaaaata tgaaaaatac acgtatgcga ggcacgtagc cgatagagct gcaaaacaat   2280
tgtaa                                                               2285
```

<210> SEQ ID NO 49
<211> LENGTH: 503

<212> TYPE: PRT
<213> ORGANISM: Homo sapiens

<400> SEQUENCE: 49

```
Met Ala Leu Ile Pro Asp Leu Ala Met Glu Thr Trp Leu Leu Leu Ala
1               5                   10                  15

Val Ser Leu Val Leu Leu Tyr Leu Tyr Gly Thr His Ser His Gly Leu
            20                  25                  30

Phe Lys Lys Leu Gly Ile Pro Gly Pro Thr Pro Leu Pro Phe Leu Gly
        35                  40                  45

Asn Ile Leu Ser Tyr His Lys Gly Phe Cys Met Phe Asp Met Glu Cys
    50                  55                  60

His Lys Lys Tyr Gly Lys Val Trp Gly Phe Tyr Asp Gly Gln Gln Pro
65                  70                  75                  80

Val Leu Ala Ile Thr Asp Pro Asp Met Ile Lys Thr Val Leu Val Lys
                85                  90                  95

Glu Cys Tyr Ser Val Phe Thr Asn Arg Arg Pro Phe Gly Pro Val Gly
            100                 105                 110

Phe Met Lys Ser Ala Ile Ser Ile Ala Glu Asp Glu Glu Trp Lys Arg
        115                 120                 125

Leu Arg Ser Leu Leu Ser Pro Thr Phe Thr Ser Gly Lys Leu Lys Glu
130                 135                 140

Met Val Pro Ile Ile Ala Gln Tyr Gly Asp Val Leu Val Arg Asn Leu
145                 150                 155                 160

Arg Arg Glu Ala Glu Thr Gly Lys Pro Val Thr Leu Lys Asp Val Phe
                165                 170                 175

Gly Ala Tyr Ser Met Asp Val Ile Thr Ser Thr Ser Phe Gly Val Asn
            180                 185                 190

Ile Asp Ser Leu Asn Asn Pro Gln Asp Pro Phe Val Glu Asn Thr Lys
        195                 200                 205

Lys Leu Leu Arg Phe Asp Phe Leu Asp Pro Phe Phe Leu Ser Ile Thr
210                 215                 220

Val Phe Pro Phe Leu Ile Pro Ile Leu Glu Val Leu Asn Ile Cys Val
225                 230                 235                 240

Phe Pro Arg Glu Val Thr Asn Phe Leu Arg Lys Ser Val Lys Arg Met
                245                 250                 255

Lys Glu Ser Arg Leu Glu Asp Thr Gln Lys His Arg Val Asp Phe Leu
            260                 265                 270

Gln Leu Met Ile Asp Ser Gln Asn Ser Lys Glu Thr Glu Ser His Lys
        275                 280                 285

Ala Leu Ser Asp Leu Glu Leu Val Ala Gln Ser Ile Ile Phe Ile Phe
290                 295                 300

Ala Gly Tyr Glu Thr Thr Ser Ser Val Leu Ser Phe Ile Met Tyr Glu
305                 310                 315                 320

Leu Ala Thr His Pro Asp Val Gln Gln Lys Leu Gln Glu Glu Ile Asp
                325                 330                 335

Ala Val Leu Pro Asn Lys Ala Pro Pro Thr Tyr Asp Thr Val Leu Gln
            340                 345                 350

Met Glu Tyr Leu Asp Met Val Val Asn Glu Thr Leu Arg Leu Phe Pro
        355                 360                 365

Ile Ala Met Arg Leu Glu Arg Val Cys Lys Lys Asp Val Glu Ile Asn
370                 375                 380

Gly Met Phe Ile Pro Lys Gly Val Val Val Met Ile Pro Ser Tyr Ala
385                 390                 395                 400
```

```
Leu His Arg Asp Pro Lys Tyr Trp Thr Glu Pro Glu Lys Phe Leu Pro
            405                 410                 415

Glu Arg Phe Ser Lys Lys Asn Lys Asp Asn Ile Asp Pro Tyr Ile Tyr
            420                 425                 430

Thr Pro Phe Gly Ser Gly Pro Arg Asn Cys Ile Gly Met Arg Phe Ala
            435                 440                 445

Leu Met Asn Met Lys Leu Ala Leu Ile Arg Val Leu Gln Asn Phe Ser
            450                 455                 460

Phe Lys Pro Cys Lys Glu Thr Gln Ile Pro Leu Lys Leu Ser Leu Gly
465                 470                 475                 480

Gly Leu Leu Gln Pro Glu Lys Pro Val Val Leu Lys Val Glu Ser Arg
            485                 490                 495

Asp Gly Thr Val Ser Gly Ala
            500

<210> SEQ ID NO 50
<211> LENGTH: 451
<212> TYPE: PRT
<213> ORGANISM: Mycobacterium tuberculosis

<400> SEQUENCE: 50

Met Ser Ala Val Ala Leu Pro Arg Val Ser Gly Gly His Asp Glu His
1               5                   10                  15

Gly His Leu Glu Glu Phe Arg Thr Asp Pro Ile Gly Leu Met Gln Arg
            20                  25                  30

Val Arg Asp Glu Cys Gly Asp Val Gly Thr Phe Gln Leu Ala Gly Lys
            35                  40                  45

Gln Val Val Leu Leu Ser Gly Ser His Ala Asn Glu Phe Phe Phe Arg
        50                  55                  60

Ala Gly Asp Asp Asp Leu Asp Gln Ala Lys Ala Tyr Pro Phe Met Thr
65                  70                  75                  80

Pro Ile Phe Gly Glu Gly Val Val Phe Asp Ala Ser Pro Glu Arg Arg
                85                  90                  95

Lys Glu Met Leu His Asn Ala Ala Leu Arg Gly Glu Gln Met Lys Gly
            100                 105                 110

His Ala Ala Thr Ile Glu Asp Gln Val Arg Arg Met Ile Ala Asp Trp
        115                 120                 125

Gly Glu Ala Gly Glu Ile Asp Leu Leu Asp Phe Phe Ala Glu Leu Thr
130                 135                 140

Ile Tyr Thr Ser Ser Ala Cys Leu Ile Gly Lys Lys Phe Arg Asp Gln
145                 150                 155                 160

Leu Asp Gly Arg Phe Ala Lys Leu Tyr His Glu Leu Glu Arg Gly Thr
                165                 170                 175

Asp Pro Leu Ala Tyr Val Asp Pro Tyr Leu Pro Ile Glu Ser Phe Arg
            180                 185                 190

Arg Arg Asp Glu Ala Arg Asn Gly Leu Val Ala Leu Val Ala Asp Ile
        195                 200                 205

Met Asn Gly Arg Ile Ala Asn Pro Pro Thr Asp Lys Ser Asp Arg Asp
210                 215                 220

Met Leu Asp Val Leu Ile Ala Val Lys Ala Glu Thr Gly Thr Pro Arg
225                 230                 235                 240

Phe Ser Ala Asp Glu Ile Thr Gly Met Phe Ile Ser Met Met Phe Ala
                245                 250                 255

Gly His His Thr Ser Ser Gly Thr Ala Ser Trp Thr Leu Ile Glu Leu
            260                 265                 270
```

```
Met Arg His Arg Asp Ala Tyr Ala Ala Val Ile Asp Glu Leu Asp Glu
        275                 280                 285
Leu Tyr Gly Asp Gly Arg Ser Val Ser Phe His Ala Leu Arg Gln Ile
    290                 295                 300
Pro Gln Leu Glu Asn Val Leu Lys Glu Thr Leu Arg Leu His Pro Pro
305                 310                 315                 320
Leu Ile Ile Leu Met Arg Val Ala Lys Gly Glu Phe Glu Val Gln Gly
                325                 330                 335
His Arg Ile His Glu Gly Asp Leu Val Ala Ala Ser Pro Ala Ile Ser
            340                 345                 350
Asn Arg Ile Pro Glu Asp Phe Pro Asp Pro His Asp Phe Val Pro Ala
        355                 360                 365
Arg Tyr Glu Gln Pro Arg Gln Glu Asp Leu Leu Asn Arg Trp Thr Trp
    370                 375                 380
Ile Pro Phe Gly Ala Gly Arg His Arg Cys Val Gly Ala Ala Phe Ala
385                 390                 395                 400
Ile Met Gln Ile Lys Ala Ile Phe Ser Val Leu Leu Arg Glu Tyr Glu
                405                 410                 415
Phe Glu Met Ala Gln Pro Pro Glu Ser Tyr Arg Asn Asp His Ser Lys
            420                 425                 430
Met Val Val Gln Leu Ala Gln Pro Ala Cys Val Arg Tyr Arg Arg Arg
        435                 440                 445
Thr Gly Val
    450

<210> SEQ ID NO 51
<211> LENGTH: 1948
<212> TYPE: DNA
<213> ORGANISM: Artificial Sequence
<220> FEATURE:
<223> OTHER INFORMATION: nucleic acid sequence of recombinant variant of
      cytochrome p450 (chimera 9T2/4G2)

<400> SEQUENCE: 51
atgttggtcg agttggtatt ggtcgccatt ttggcgttgt tgttttacta ccagttcgtg      60
agaccgctag gtaccagttt gtacgaaata tggctaagga ataccaggaa atataaatta     120
acggcaaata tgccaaaccc acctatgctg ccactcatcg gaaatggcca tttggtggcc     180
catttgacaa atgccgaaat ccttgcccgt ggcattggtt acatgcaaac ctatggtggt     240
gccatgcgtg gcttttttggg tcccatgttg gttgtgttcc tctggaacgc tcccgatatt     300
gaattgattc tcagtaccca cacccatttg agaagtcaa ttgaatatcg tttcttcaaa     360
ccctggtttg gtgatggtct acttatttcg aatggtcacc attggcaaca tcatcgcaaa     420
atgattgctc caacattcca tcaaagcatt ttgaagagtt tcgtgccagc ctttgtgcaa     480
cactccaaga aggtggtgga acgtatggcc aaggaattgg gcaaggaatt cgatgtccat     540
gactatatgt cacagaccac tgtggaaatt ttgctctcca ctgccatggg tgttaagaag     600
gtgcccgagg acaacaagag tttggaatat gccaaggctg tggtggacat gtgcgacatc     660
attcacaagc gccaattgaa attcttctat cgcatggatg ccctctacaa tttgagcagc     720
atgagtgaga agggcaagaa gatgatggac attattttgg gcatgacccg taaagtggtg     780
acggaacgtc aacagaattt caatgccgaa tcgcgtgcca ttgtcgagga ggatgatgaa     840
attagcaagc agaagcaaca ggccaagaag aaggagggtt tgcgtgatga tttggatgac     900
attgatgaaa atgatgtggg tgccaagaaa cgtttggctc tgctggatgc catgatggcc     960
atgtccaaga accccgatgt tgagtggacc gacaaggatg tcatggatga agtcaacacc     1020
```

-continued

```
attatgtttg agggccacga taccacctca gctggttcca gttttgtcct ctgcatgttg    1080
ggcatctaca aggatatcca agagaaagtc ctggccgaac aaaaggccat ctttggtgac   1140
aacttcctgc gcgactgtac ctttgccgat accatggaaa tgaaatacct ggaacgtgtg   1200
attatggaga ctttgcgttt gtatccacca gtaccccttta ttgcccgtcg tgctgagttc   1260
gatgtaaaat tggcttccgg tccctacaca attcccaagg gcacaacagt ggtgattgcc   1320
caatttgctg tgcatcgcaa tccccaatac ttccccaatc ccgagaaatt cgatcctgac   1380
aatttcctac ccgaacgtat ggccaatcgt cattactaca gtttcattcc cttcagtgcc   1440
ggccccagaa gttgcgttgg ccgcaaatat gccatgctga aattaaaggt cctgctctcc   1500
accattattc gtaactattc ggtgcagagc aaccaacagg agaaggactt taagttgcag   1560
gccgatatta tcctaaagat tgaaaatggt ttcaatatca tgttgaaccg acgacccgaa   1620
gccatgaaag ctatgtaaag taaagtagag atgagtgtgt aaagaagttt tttgtcccaa   1680
ctatcctaag aatgacccgt atccttgtat gtggtttcca tttttattgat aagtaaaaga   1740 agaaagaaac taaccccccg cattataccaa ataataaga aataacgaaa ctactaaccg   1800
acgtgagagt gttaagtttt atcctattgt tattgactaa aatgtatgtt aagatttttt   1860
ttttataaat tttattgttt ttgaagaaaa cacaaaaatt ttaaaaaaaa ataataaaga   1920
gcatgccagt ttaaaactgt aaaaaaaa                                       1948
```

<210> SEQ ID NO 52
<211> LENGTH: 545
<212> TYPE: PRT
<213> ORGANISM: Artificial Sequence
<220> FEATURE:
<223> OTHER INFORMATION: amino acid sequence of recombinant variant of cytochrome p450 (chimera 9T2/4G2)

<400> SEQUENCE: 52

```
Met Leu Val Glu Leu Val Leu Val Ala Ile Leu Ala Leu Leu Phe Tyr
1               5                   10                  15

Tyr Gln Phe Val Arg Pro Leu Gly Thr Ser Leu Tyr Glu Ile Trp Leu
            20                  25                  30

Arg Asn Thr Arg Lys Tyr Lys Leu Thr Ala Asn Met Pro Asn Pro Pro
        35                  40                  45

Met Leu Pro Leu Ile Gly Asn Gly His Leu Val Ala His Leu Thr Asn
    50                  55                  60

Ala Glu Ile Leu Ala Arg Gly Ile Gly Tyr Met Gln Thr Tyr Gly Gly
65                  70                  75                  80

Ala Met Arg Gly Phe Leu Gly Pro Met Leu Val Val Phe Leu Trp Asn
                85                  90                  95

Ala Pro Asp Ile Glu Leu Ile Leu Ser Thr His Thr His Leu Glu Lys
            100                 105                 110

Ser Ile Glu Tyr Arg Phe Phe Lys Pro Trp Phe Gly Asp Gly Leu Leu
        115                 120                 125

Ile Ser Asn Gly His His Trp Gln His His Arg Lys Met Ile Ala Pro
    130                 135                 140

Thr Phe His Gln Ser Ile Leu Lys Ser Phe Val Pro Ala Phe Val Gln
145                 150                 155                 160

His Ser Lys Lys Val Val Glu Arg Met Ala Lys Glu Leu Gly Lys Glu
                165                 170                 175

Phe Asp Val His Asp Tyr Met Ser Gln Thr Thr Val Gly Ile Leu Leu
            180                 185                 190
```

-continued

```
Ser Thr Ala Met Gly Val Lys Lys Val Pro Glu Asp Asn Lys Ser Leu
        195                 200                 205
Glu Tyr Ala Lys Ala Val Val Asp Met Cys Asp Ile Ile His Lys Arg
    210                 215                 220
Gln Leu Lys Phe Phe Tyr Arg Met Asp Ala Leu Tyr Asn Leu Ser Ser
225                 230                 235                 240
Met Ser Glu Lys Gly Lys Lys Met Met Asp Ile Ile Leu Gly Met Thr
                245                 250                 255
Arg Lys Val Val Thr Glu Arg Gln Gln Asn Phe Asn Ala Glu Ser Arg
            260                 265                 270
Ala Ile Val Glu Glu Asp Glu Ile Ser Lys Gln Lys Gln Gln Ala
        275                 280                 285
Lys Lys Lys Glu Gly Leu Arg Asp Asp Leu Asp Asp Ile Asp Glu Asn
    290                 295                 300
Asp Val Gly Ala Lys Lys Arg Leu Ala Leu Leu Asp Ala Met Met Ala
305                 310                 315                 320
Met Ser Lys Asn Pro Asp Val Glu Trp Thr Asp Lys Asp Val Met Asp
                325                 330                 335
Glu Val Asn Thr Ile Met Phe Gly His Asp Thr Thr Ser Ala Gly
            340                 345                 350
Ser Ser Phe Val Leu Cys Met Leu Gly Ile Tyr Lys Asp Ile Gln Glu
            355                 360                 365
Lys Val Leu Ala Glu Gln Lys Ala Ile Phe Gly Asp Asn Phe Leu Arg
    370                 375                 380
Asp Cys Thr Phe Ala Asp Thr Met Glu Met Lys Tyr Leu Glu Arg Val
385                 390                 395                 400
Ile Met Glu Thr Leu Arg Leu Tyr Pro Pro Val Pro Leu Ile Ala Arg
                405                 410                 415
Arg Ala Glu Phe Asp Val Lys Leu Ala Ser Gly Pro Tyr Thr Ile Pro
            420                 425                 430
Lys Gly Thr Thr Val Val Ile Ala Gln Phe Ala Val His Arg Asn Pro
            435                 440                 445
Gln Tyr Phe Pro Asn Pro Glu Lys Phe Asp Pro Asp Asn Phe Leu Pro
    450                 455                 460
Glu Arg Met Ala Asn Arg His Tyr Tyr Ser Phe Ile Pro Phe Ser Ala
465                 470                 475                 480
Gly Pro Arg Ser Cys Val Gly Arg Lys Tyr Ala Met Leu Lys Leu Lys
                485                 490                 495
Val Leu Leu Ser Thr Ile Ile Arg Asn Tyr Ser Val Gln Ser Asn Gln
            500                 505                 510
Gln Glu Lys Asp Phe Lys Leu Gln Ala Asp Ile Ile Leu Lys Ile Glu
    515                 520                 525
Asn Gly Phe Asn Ile Met Leu Asn Arg Arg Pro Glu Ala Met Lys Ala
    530                 535                 540
Met
545
```